(12) United States Patent
Lord et al.

(10) Patent No.: US 12,233,060 B2
(45) Date of Patent: Feb. 25, 2025

(54) INHIBITORS OF ATAXIA-TELANGIECTASIA MUTATED AND RAD3-RELATED PROTEIN KINASE (ATR) FOR USE IN METHODS OF TREATING CANCER

(71) Applicants: THE INSTITUTE OF CANCER RESEARCH: ROYAL CANCER HOSPITAL, London (GB); BREAST CANCER NOW, London (GB)

(72) Inventors: Christopher James Lord, London (GB); Chris Williamson, London (GB); Samuel Jones, London (GB)

(73) Assignees: THE INSTITUTE OF CANCER RESEARCH: ROYAL CANCER HOSPITAL, London (GB); BREAST CANCER NOW, London (GB)

( * ) Notice: Subject to any disclaimer, the term of this patent is extended or adjusted under 35 U.S.C. 154(b) by 0 days.

(21) Appl. No.: 16/067,994

(22) PCT Filed: Jan. 6, 2017

(86) PCT No.: PCT/EP2017/050270
§ 371 (c)(1),
(2) Date: Jul. 3, 2018

(87) PCT Pub. No.: WO2017/118734
PCT Pub. Date: Jul. 13, 2017

(65) Prior Publication Data
US 2019/0008856 A1 Jan. 10, 2019

(30) Foreign Application Priority Data

Jan. 8, 2016 (GB) .................................... 1600388
Dec. 16, 2016 (GB) .................................... 1621472

(51) Int. Cl.
| A61K 31/4965 | (2006.01) |
| A61K 31/497 | (2006.01) |
| A61K 31/506 | (2006.01) |
| A61K 31/519 | (2006.01) |
| A61K 31/7105 | (2006.01) |
| A61P 35/00 | (2006.01) |

(52) U.S. Cl.
CPC ........ *A61K 31/497* (2013.01); *A61K 31/4965* (2013.01); *A61K 31/519* (2013.01); *A61K 31/7105* (2013.01); *A61P 35/00* (2018.01)

(58) Field of Classification Search
CPC .............. A61K 31/4965; A61K 31/497; A61K 31/506; A61K 31/519; A61P 35/00
See application file for complete search history.

(56) References Cited

U.S. PATENT DOCUMENTS

| 2013/0115313 A1 | 5/2013 | Charrier et al. |
| 2014/0044802 A1* | 2/2014 | Pollard .............. A61K 31/4965 |
| | | 424/649 |
| 2014/0249157 A1* | 9/2014 | Ahmad .................. A61P 17/00 |
| | | 514/252.16 |
| 2015/0359797 A1 | 12/2015 | Helleday et al. |

FOREIGN PATENT DOCUMENTS

| JP | 2015-515478 A | 5/2015 |
| WO | 2012071096 A2 | 5/2012 |
| WO | 2013152298 A1 | 10/2013 |
| WO | 2015095329 A1 | 6/2015 |
| WO | 2015/195740 A1 | 12/2015 |
| WO | 2015187451 A9 | 12/2015 |
| WO | 2016112374 A2 | 7/2016 |
| WO | 2016130581 A2 | 8/2016 |

OTHER PUBLICATIONS

Caumanns et al. BBA—Reviews on Cancer 2018, 1870, 176-184.*
Wu et al. Cancer Biology & Therapy 2014, 15 (6), 655-664.*
Arnaud et al Cancer Letters 2018, 419, 266-279.*
Lucking et al. J. Med. Chem. 2020, 63, 7293-7325.*
Brandsma, I. et al., "Exploiting synthetic lethal interactions in DNA repair deficient tumour cells using ATR inhibition", DNA Repair Modulation, Poster Abstracts 365, Dec. 2016.
Lim, Stephanie Hui-Su et al., "Systemic therapy in neurofibromatosis type 2", Cancer Treatment Reviews, 40: 857-861 (2014).
O'Connor, Mark J. et al., "Targeting the DNA Damage Response in Cancer", Molecular Cell 60: 547-560 (2015).
Shen, Jianfeng et al., "ARID1A Deficiency Impairs the DNA Damage Checkpoint and Sensitizes Cells to PARP Inhibitors", Cancer Discov., 5(7): 752-67 (2015).
Sultana, Rebeka et al., "Ataxia Telangiectasia Mutated and Rad3 Related (ATR) Protein Kinase Inhibition is Synthetically Lethal in XRCC1 Deficient Ovarian Cancer Cells", PLoS ONE, 8(2): e57098 (2013).
Weber, Anika Maria et al., "ATM and ATR as therapeutic targets in cancer", Pharmacology & Therapeutics, 149 (124-138 (2015).
Williamson, Chris et al., "Defects in ARIDIA and other BAF complex tumour supressor genes sensitise tumour cells to clinical inhibitors of the DNA damage checkpoint kinase, ATR", Breast Cancer Res. Treat, 159: 177-197 (2016).
Williamson, Chris T. et al., "ATR inhibitors as a synthetic lethal therapy for tumours deficient in ARID1A", Nature Communications, 7: 13837, doi: 10.1038/ncomms13837 (2016).
Yoon, Heejei et al., Abstract 4364: Copy number gain of PTK2 and PIK3CA mutations are common genetic alterations in ovarian clear cell carcinoma, In: Proceedings of the 104th Annual Meeting of the American Association for Cancer Research, Apr. 6-10, Washington DC Philadelphia, PA: AACR; Cancer Research, 73(8 Suppl): Abstract nr 4364. doi: 10.1158/1538-7445.AM2013-4364 (2013.

(Continued)

*Primary Examiner* — Irina Neagu
(74) *Attorney, Agent, or Firm* — Kathleen D. Rigaut; Howson & Howson LLP

(57) ABSTRACT

The present invention relates to Ataxia-Telangiectasia Mutated and Rad3-related protein kinase (ATR) inhibitors for use in methods of treating BAF-complex deficient cancer. The present invention further provides methods for identifying ATR inhibitors for use in the treatment of BAF complex gene mutant or deficient cancers. Medical uses and methods relating to the treatment of synovial sarcoma using ATR inhibitors are also provided.

9 Claims, 29 Drawing Sheets

(56) References Cited

OTHER PUBLICATIONS

International Search Report and Written Opinion, dated May 24, 2017, issued in corresponding International Application No. PCT/EP2017/050270.

Middleton, F.K. et al., "Common cancer-associated imbalances in the DNA damage response confer sensitivity to single agent ATR inhibition," Oncotarget, vol. 6, No. 32, pp. 32396-32409, Oct. 15, 2015, doi: 10.18632/oncotarget.6136.

Watanabe, R. et al., "SWI/SNF Factors Required for Cellular Resistance to DNA Damage Include ARID1A and ARID1B and Show Interdependent Protein Stability," Cancer Research, vol. 74, No. 9, pp. 2465-2475, May 1, 2014, doi:10.1158/0008-5472.CAN-13-3608.

Notice of Reasons for Rejection issued in corresponding Japanese Application No. 2018-535894, dated Feb. 2, 2021.

Chabanon, Roman M. et al., "PBRM1 Deficiency Confers Synthetic Lethality to DNA Repair Inhibitors in Cancer," Cancer Research, vol. 81, No. 11, Jun. 2021, pp. 2888-2902. (with supplementary materials).

Chory, Emma J. et al., "Chemical Inhibitors of a Selective SWI/SNF Function Synergize with ATR Inhibition in Cancer Cell Killing," ACS Chemical Biology, vol. 15, No. 6, Jun. 2020, pp. 1685-1696.

Gupta, Manav et al., "BRG1 Loss Predisposes Lung Cancers to Replicative Stress and ATR Dependency," Cancer Research, vol. 80, No. 18, Sep. 2020, pp. 3841-3854.

Jones, Samuel E. et al, "ATR Is a Therapeutic Target in Synovial Sarcoma," Cancer Research, vol. 77, No. 24, Dec. 2017, pp. 7014-7026.

Kurashima, Kiminori et al., "SMARCA4 deficiency-associated heterochromatin induces intrinsic DNA replication stress and susceptibility to ATR inhibition in lung adenocarcinoma," NAR Cancer, vol. 2, No. 2, Jun. 2020, pp. 1-19.

Kurz, Lukas et al., "ARID1A Regulates Transcription and the Epigenetic Landscape via POLE and DMAP1 While ARID1A Deficiency or Pharmacological Inhibition Sensitizes Germ Cell Tumor Cells to ATR Inhibition," Cancers, vol. 12, No. 4, Apr. 2020, 905 pp. 1-19.

Marian, Christine A. et al., "Small Molecule Targeting of Specific BAF (mSWI/SNF) Complexes for HIV Latency Reversal," Cell Chemical Biology, vol. 25, No. 12, Dec. 2018, pp. 1443-1455.

Viol, Fabrice et al., "Novel preclinical gastroenteropancreatic neuroendocrine neoplasia models demonstrate the feasibility of mutation-based targeted therapy," Cellular Oncology, vol. 45, No. 6, Dec. 2022, pp. 1401-1419.

Williamson, Chris T et al., "ATR inhibitors as a synthetic lethal therapy for tumours deficient in ARID1A," Nature Communications, vol. 7, No. 1, Dec. 2016, 13837 pp. 1-13.

Xu, Shan et al., "Selective vulnerability of ARID1A deficient colon cancer cells to combined radiation and ATR-inhibitor therapy," Frontiers in Oncology, vol. 12, Sep. 2022, 999626 pp. 1-14.

* cited by examiner

C.

—○— SYO1
··○·· HS-SY-II
—○— HCT116 *ARID1A+/+*
··○·· HCT116 *ARID1A+/+*

E

ANOVA
p< 0.0001

G

Empty
SS18-SSX1
SS18-SSX2
d71-78
SS18-SSX
SS18
SMARCB1
Tubulin

ANOVA
p< 0.0001

FIG. 8 (Continued)

B image# INHIBITORS OF ATAXIA-TELANGIECTASIA MUTATED AND RAD3-RELATED PROTEIN KINASE (ATR) FOR USE IN METHODS OF TREATING CANCER

CROSS-REFERENCE TO RELATED APPLICATIONS

This application is a § 371 of International Application No. PCT/EP2017/050270, filed Jan. 6, 2017, which claims priority from Great Britain Applications Nos. 1600388.1, filed Jan. 8, 2016 and 1621472.8, filed Dec. 16, 2016, respectively. The entire disclosure of each of the aforesaid applications is incorporated by reference in the present application.

FIELD OF THE INVENTION

The present invention relates to Ataxia-Telangiectasia Mutated and Rad3-related protein kinase (ATR) inhibitors for use in methods of treating BAF-complex deficient cancer, and in particular to materials and methods for exploiting synthetic lethality in the treatment of cancer, such as ARID1A deficient cancer, using ATR inhibitors. The present invention further provides methods for identifying ATR inhibitors for use in the treatment of BAF complex gene mutant or deficient cancers. Medical uses and methods relating to the treatment of synovial sarcoma using ATR inhibitors are also provided.

BACKGROUND OF THE INVENTION

Each year, the majority of new cancer drug approvals are directed against existing targets, whereas only two or three compounds are licensed against novel molecules. Rather than suggesting a limiting number of targets, this reflects the difficulty, time and cost involved in the identification and validation of proteins that are crucial to disease pathogenesis. The result is that many key proteins remain undrugged, and consequently opportunities to develop novel therapies are lost. This situation could be improved by using approaches that identify the key molecular targets that underlie the pathways that are associated with disease development. For example, techniques such as gene targeting, in which a gene can be selectively inactivated or knocked-out, can be powerful. However, such approaches are limited by their cost and low throughput. Moreover, it is often the case that the current approaches to cancer treatment group together similar clinical phenotypes regardless of the differing molecular pathologies that underlie them. A consequence of this molecular heterogeneity is that individuals frequently exhibit vast differences to drug treatments. As such, therapies that target the underlying molecular biology of individual cancers are increasingly becoming an attractive approach. ATR (Ataxia-Telangiectasia Mutated (ATM) and Rad3-related protein kinase) is a critical component of the cellular DNA damage response (DDR) (1). ATR is activated by regions of single-stranded DNA, which frequently occur as a result of replication stress (2-4). Oncogene activation can induce replication stress and a reliance upon on ATR checkpoint function, providing one rationale for the use of small molecule ATR inhibitors (ATRi) as cancer therapeutics (5). Recently, potent and specific ATRi have been discovered including VE-821 and VX-970 (aka VE-822) (Vertex) currently in Phase I clinical trial (5). However, to date, only defects in canonical DNA repair genes ERCC1 (10), XRCC1 (11) and ATM (12) have been proposed as predictive biomarkers of single agent ATRi sensitivity. It is also not clear whether process beyond canonical DDR might impact upon ATRi sensitivity and whether other commonly occurring cancer driver genes might alter the response to these agents.

There remains a need in the art for new therapeutic strategies, in particular those which target genetic dependencies of different forms of cancer.

SUMMARY OF THE INVENTION

Broadly, the present invention is based on work that attempts to identify synthetic lethal genetic factors as biomarkers for ATR-inhibitor sensitivity. These results are based on exemplary evidence using the ATR-inhibitors VE-821 and VX-970. In preclinical studies, VE-821 has been shown to potentiate the cytotoxic effects of a number of DNA damaging agents (6-9), suggesting that ATR-inhibitors (ATRi) might have clinical utility as chemosensitising agents. However, the context in which ATRi might be used, for example as single agents, for the treatment of cancers is less clear.

Drugs that inhibit the kinase activity of ATR (ATRi) have recently entered Phase 1 clinical trials for the treatment of cancer, primarily as chemosensitising agents. To uncover genetic determinants of single-agent ATRi response, the work leading to the present invention performed a series of synthetic lethal genetic screens, finding that defects in the BAF complex tumour suppressor gene, ARID1A, profoundly sensitised tumour cells to ATRi both in vitro and in vivo. ATRi elicited premature mitotic entry, genomic instability and apoptosis in ARID1A mutant cells, effects likely caused by pre-existing topoisomerase and DNA decatenation defects. BAF complex defects are present in ≈20% of human tumours. The work described herein found that inhibition of other BAF tumour suppressor genes also caused ATRi sensitivity, suggesting that this synthetic lethal approach could have wider utility. This data therefore provides the preclinical and mechanistic rationale for BAF defects being assessed as biomarkers of ATRi response.

In the study described below, we aimed to identify clinically actionable determinants of single agent ATRi sensitivity. Using large-scale genetic screens we identified the BAF component ARID1A as a synthetic lethal target of ATRi. Based on this data, the present invention proposes that ARID1A and BAF defects could serve as a clinically useful biomarkers of ATRi sensitivity.

SWItch/Sucrose Non-Fermentable (SWI/SNF) chromatin-remodelling complexes are composed of multiple components, including proteins such as ARID1A, SMARCA4 and SMARCB1 that have tumour suppressor roles (13). Although the protein composition of SWI/SNF complexes varies greatly, two primary versions of SWI/SNF exist, BAF and PBAF (14). When taken as a group, SWI/SNF components are estimated to be mutated in nearly 20% of all human tumours making loss of this complex one of the most common alterations in cancer (13).

In addition, as translocations in genes associated with synovial sarcomas are known to also cause BAF-complex defects, the present invention extends to the treatment of synovial sarcomas with ATR inhibitors, as demonstrated by experiments in which cells lines containing such gene translocation defects are sensitive to ATR inhibitors. The experiments demonstrate that this effect is generic as the cell lines are sensitive to ssRNAi molecules that target Ataxia-Telangiectasia Mutated and Rad3-related protein kinase (ATR).

In the present invention, references to ATR denote Ataxia-Telangiectasia Mutated (ATM) and Rad3-related protein kinase. In the present invention, references to ATR denote Ataxia-Telangiectasia Mutated (ATM) and Rad3-related protein kinase, having the HGNC ID: 882. The HUGO Gene Symbol report for ATR can be found at: http://www.genenames.org/cgi-bin/gene symbol report?hgnc id=HGNC:882 which provides links to the ATR nucleic acid and amino acid sequences, as well as reference to the homologous murine and rat proteins.

Inhibitors of ATR (ATRi) are disclosed for use in the treatment of cancer mutated or deficient in one or more BAF-complex genes selected from ARID1A, ARID1B, ARID2, SMARCA2, SMARCA4, SMARCB1, SMARCC2, SMARCC1, SMARCD1, SMARCD2, SMARCD3, SMARCE1, ACTL6A, ACTL6B, and/or PBRM1, and especially for the treatment of cancer mutated or deficient in the BAF-complex gene, ARID1A.

Accordingly, in a first aspect, the present invention provides an Ataxia-Telangiectasia Mutated and Rad3-related protein kinase inhibitor (ATRi) for use in a method of treating an individual having cancer, wherein the cancer is mutated or deficient in one or more BAF-complex genes.

In a further aspect, the present invention provides an Ataxia-Telangiectasia Mutated and Rad3-related protein kinase inhibitor (ATRi) for use in a method of treating an individual having cancer which is mutated or deficient in one or more BAF-complex gene, the method comprising:
(a) determining in a sample obtained from the individual whether the cancer is mutated or deficient in one or more BAF-complex genes, and
(b) administering a therapeutically effective amount of an ATR inhibitor to the individual where the cancer has one or more BAF-complex gene mutations or deficiencies.

By way of example, the mutated or deficient BAF-complex gene is selected from one or more of ARID1A, ARID1B, ARID2, SMARCA2, SMARCA4, SMARCB1, SMARCC2, SMARCC1, SMARCD1, SMARCD2, SMARCD3, SMARCE1, ACTL6A, ACTL6B, and/or PBRM1. More preferably, the mutated or deficient BAF-complex gene is selected from one or more of ARID1A, ARID1B, ARID2, SMARCA2, SMARCA4 and SMARCB1, and more preferably, the mutated or deficient BAF-complex gene is ARID1A.

In a further aspect, the present invention provides an Ataxia-Telangiectasia Mutated and Rad3-related protein kinase inhibitor (ATRi) for use in a method of treating an individual having synovial sarcoma.

In a further aspect, the present invention provides an Ataxia-Telangiectasia Mutated and Rad3-related protein kinase inhibitor (ATRi) for use in a method of treating an individual having synovial sarcoma which is mutated or deficient in one or more genes selected from SSX1, SSX2 or SS18, the method comprising:
(a) determining in a sample obtained from the individual whether the cancer is mutated or deficient in one or more BAF-complex genes, and
(b) administering a therapeutically effective amount of an ATR inhibitor to the individual where the cancer has a mutation or deficiency in one or more genes selected from SSX1, SSX2 and/or SS18.

The mutation or deficiency may be a translocation encoding an SS18-SSX1 or SS18-SSX2 fusion protein.

In a further aspect, the present invention provides a method of selecting an individual having cancer for treatment with an Ataxia-Telangiectasia Mutated and Rad3-related protein kinase inhibitor (ATRi), the method comprising:
(a) determining in a sample obtained from the individual whether the cancer is mutated or deficient in one or more BAF-complex genes, and
(b) selecting the individual for treatment with the ATR inhibitor where the cancer has one or more BAF-complex gene mutations or deficiencies; and
(c) providing an inhibitor of ATR suitable for administration to the individual.

Optionally, the method may further comprises administering a therapeutically effective amount of an inhibitor of ATR to the individual.

In a further aspect, the present invention provides a method for treating an individual having cancer with an Ataxia-Telangiectasia Mutated and Rad3-related protein kinase inhibitor (ATRi), the method comprising:
(a) determining in a sample obtained from the individual whether the cancer is mutated or deficient in one or more BAF-complex genes, and
(b) selecting the individual for treatment with the ATR inhibitor where the cancer has one or more BAF-complex gene mutations or deficiencies; and
(c) providing an inhibitor of ATR suitable for administration to the individual; and
(d) administering a therapeutically effective amount of an inhibitor of ATR to the individual.

In a further aspect, the present invention provides a method of selecting an individual having synovial sarcoma for treatment with an Ataxia-Telangiectasia Mutated and Rad3-related protein kinase inhibitor (ATRi), the method comprising:
(a) determining in a sample obtained from the individual whether the synovial sarcoma is mutated or deficient in one or more genes selected from SSX1, SSX2 and/or SS18; and
(b) selecting the individual for treatment with the ATR inhibitor where the synovial sarcoma has one or more mutations or deficiencies in said one or more genes selected from SSX1, SSX2 and/or SS18; and
(c) providing an inhibitor of ATR suitable for administration to the individual.

The mutation or deficiency may be a translocation encoding an SS18-SSX1 or SS18-SSX2 fusion protein.

Optionally, the method further comprises administering a therapeutically effective amount of an inhibitor of ATR to the individual.

In a further aspect, the present invention provides a method for treating an individual having synovial sarcoma with an Ataxia-Telangiectasia Mutated and Rad3-related protein kinase inhibitor (ATRi), the method comprising:
(a) determining in a sample obtained from the individual whether the synovial sarcoma is mutated or deficient in one or more genes selected from SSX1, SSX2 and/or SS18, and
(b) selecting the individual for treatment with the ATR inhibitor where the synovial sarcoma has one or more mutations or deficiencies in said one or more genes selected from SSX1, SSX2 and/or SS18; and
(c) providing an inhibitor of ATR suitable for administration to the individual; and
(d) administering a therapeutically effective amount of an inhibitor of ATR to the individual.

The mutation or deficiency may be a translocation encoding an SS18-SSX1 or SS18-SSX2 fusion protein. Accordingly, the method may comprise the step of determining whether the synovial sarcoma has a translocation encoding an SS18-SSX1 or SS18-SSX2 fusion protein.

In a further aspect, the step of testing the sample to determine whether the cancer is mutated or deficient in one or more BAF-complex gene is performed on nucleic acid sequences obtained from an individual's cancerous or non-cancerous cells. Suitable techniques are well known in the art and include the use of direct sequencing, hybridisation to a probe, restriction fragment length polymorphism (RFLP) analysis, single-stranded conformation polymorphism (SSCP), PCR amplification of specific alleles, amplification of DNA target by PCR followed by a mini-sequencing assay, allelic discrimination during PCR, Genetic Bit Analysis, pyrosequencing, oligonucleotide ligation assay, analysis of melting curves, testing for a loss of heterozygosity (LOH) or next generation sequencing (NGS) techniques.

In other embodiments, the test is performed on RNA sequences obtained from an individual's cancerous or non-cancerous cells. In yet further embodiments, the test is performed on proteins obtained from an individual's cancerous or non-cancerous cells.

Embodiments of the present invention will now be described by way of example and not limitation with reference to the accompanying figures. However various further aspects and embodiments of the present invention will be apparent to those skilled in the art in view of the present disclosure.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

DETAILED DESCRIPTION

Figure 1:
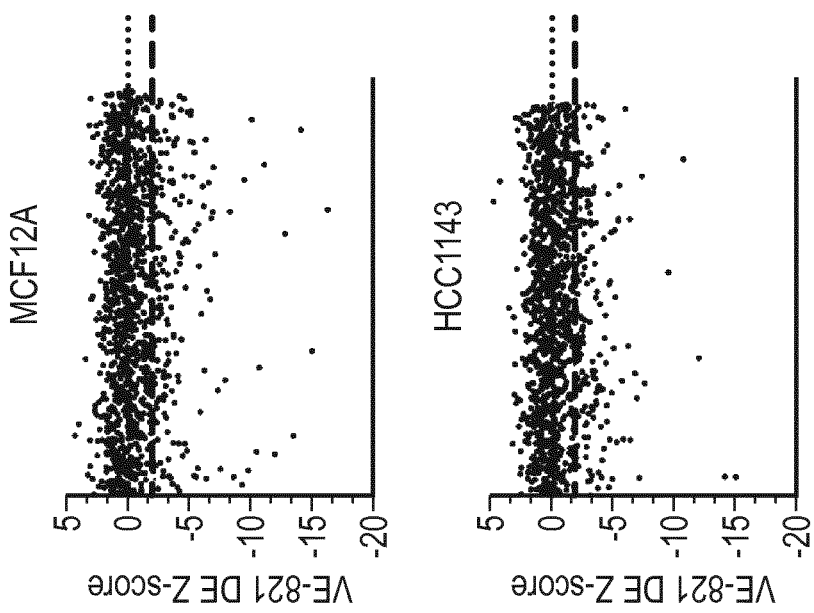
FIG. 1. RNAi screen reveals genetic determinants of ATRi sensitivity. A. Structure of VE-821 and schematic describing workflow for parallel VE-821 chemosensitisation screens in MCF12A and HCC1143 cells. B. Scatter plots of VE-821 Drug Effect (DE) Z-scores from all 1280 siRNAs used in the in the chemosensitisation screens. The DE Z-score threshold of −2 (red line) was used for defining candidate synthetic lethal interactions is shown. C. Venn diagram of DE<−2 VE-821 sensitisation hits in MCF12A and HCC1143 cells. Numbers shown indicate number of sensitisation genes. Amongst the 30 genes with DE Z-scores <−2 in both cell lines, seven well-established tumour suppressor genes were identified. D. Bar charts illustrating DE Z-scores for control, non-targeting, siRNAs (siALLSTAR, siCON1, siCON2) and ARID1A siRNAs in the chemosensitisation screens. Values shown are median from triplicate screens and error bars represent SD. E. 384 well plate cell survival data from HCC1143 cells transfected with siRNA targeting ARID1A (red) or siCon1 (blue). Twenty-four hours after transfection, cells were exposed to VE-821 for five continuous days. Error bars represent SD from triplicate experiments. Survival curve siARID1A vs. siCON1 p-value <0.0001, ANOVA. F. Western blot illustrating ARID1A protein silencing from experiment (E).
Figure 1:
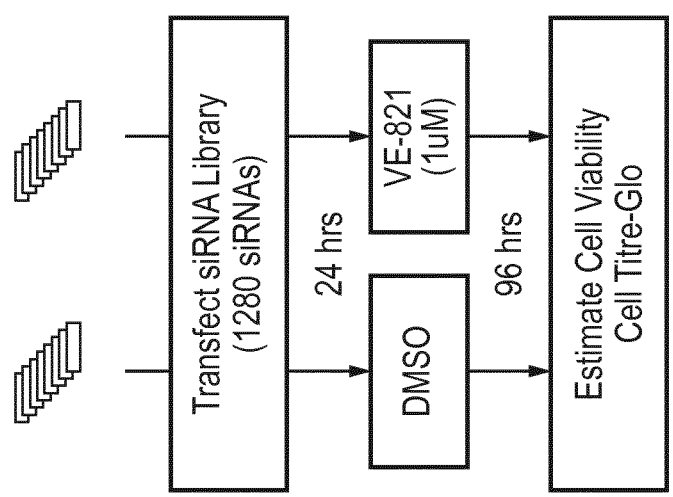
Figure 1:
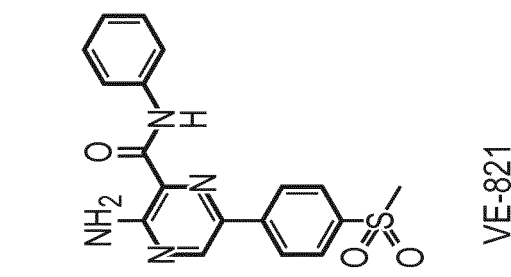
Figure 1:
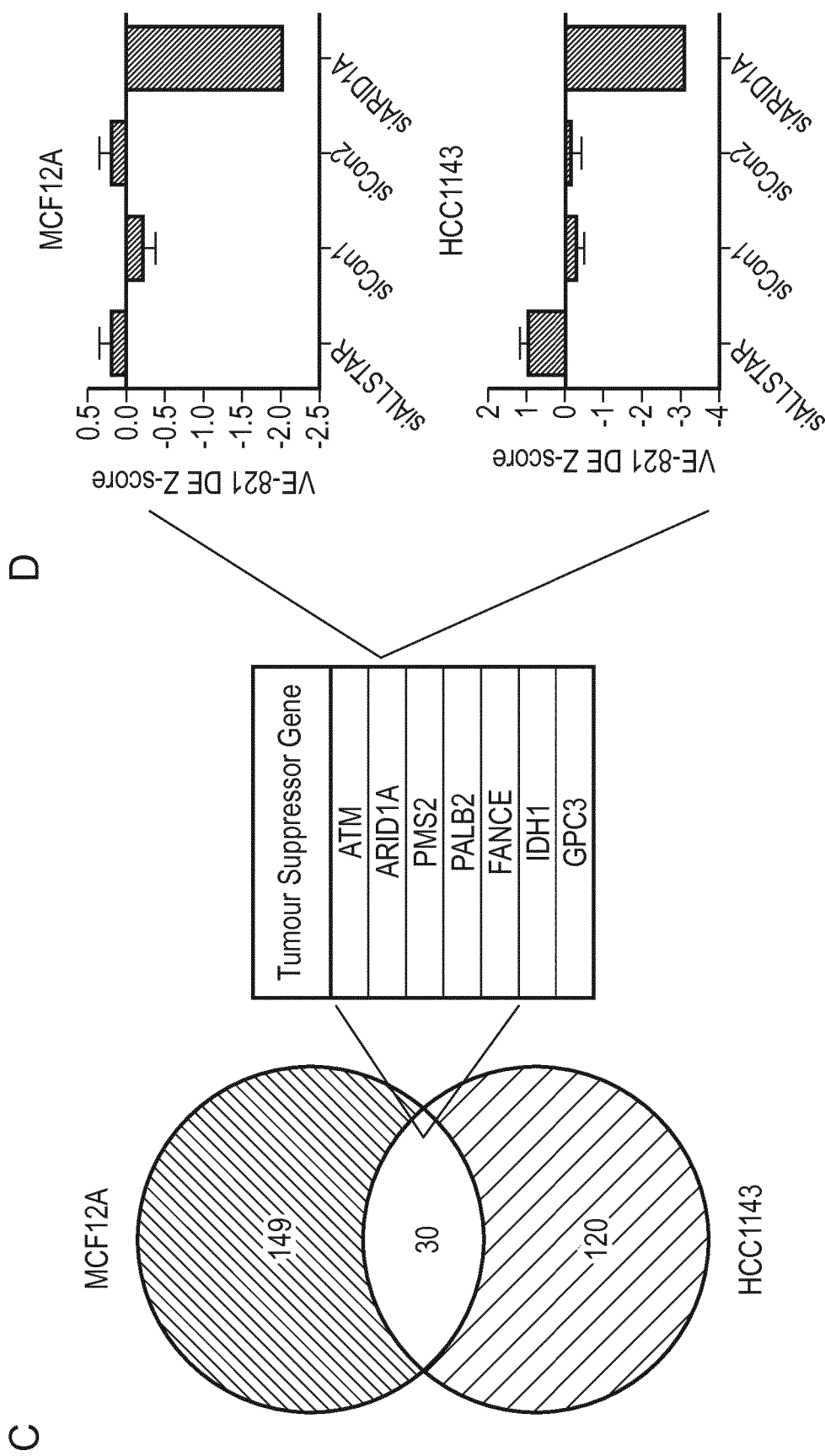
Figure 1:
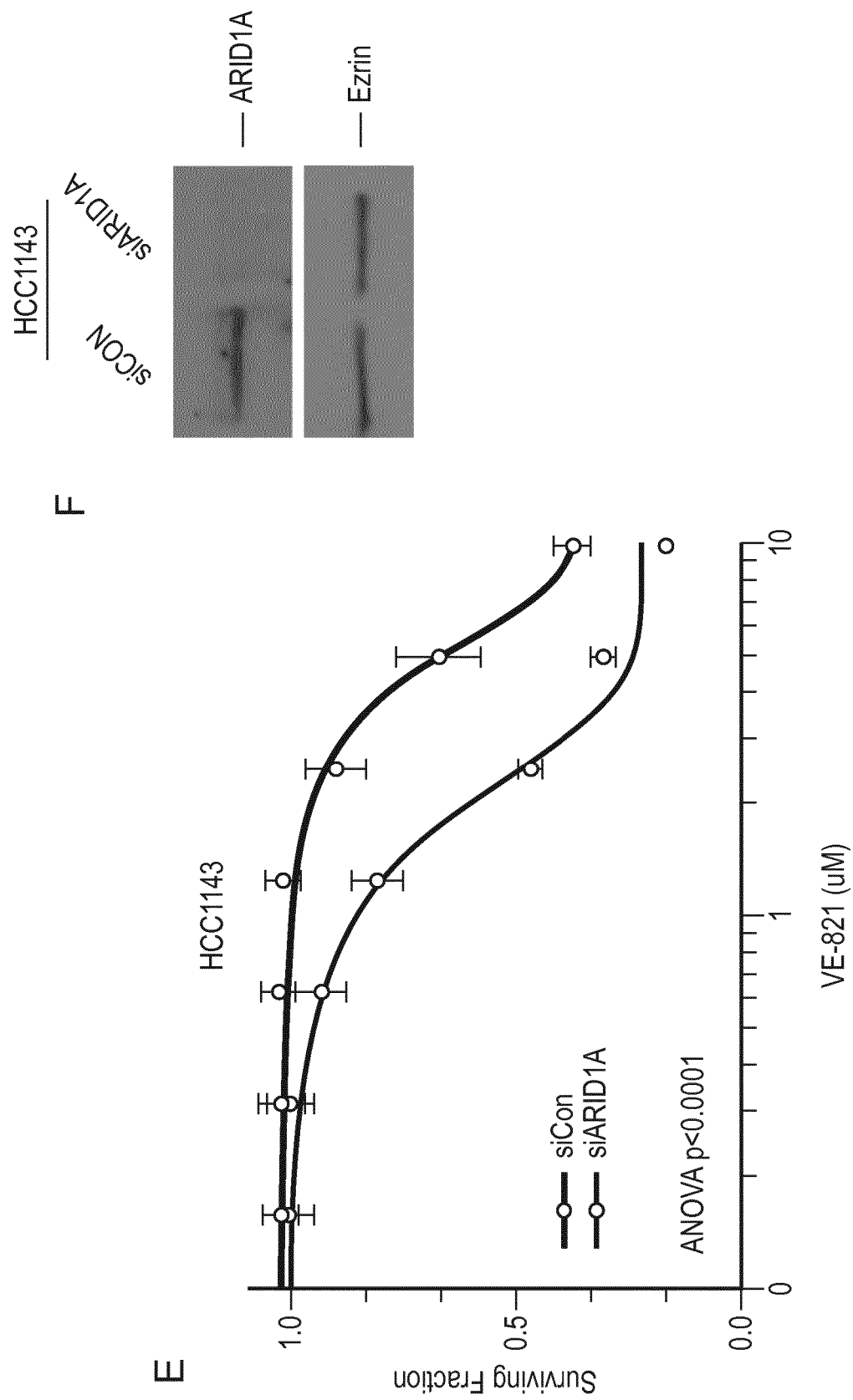

Cancers with Defects (Mutations, Loss of Expression) in the Following Genes Associated with SWI/SNF BAF Defects In the present invention, references to cancers which are mutated or deficient in one or more BAF-complex genes denote members whose protein products comprise the multi-subunit SWI/SNF chromatin-remodelling complexes "BRG1- or HRBM-associated factors" (BAF) and poly-bromo-associated BAF (PBAF). They mediate ATP-dependent chromatin remodelling processes during transcription, replication, and DNA repair and are critical for differentiation and proliferation. Several components of the complexes function as tumour suppressors (see Reisman, Oncogene 28: 1653-1668, 2009, hereby incorporated by reference). BAF complex genes include, but are not limited to, ARID1A, ARID1B, ARID2, SMARCA2, SMARCA4, SMARCB1, SMARCC2, SMARCC1, SMARCD1, 2 and 3, SMARCE1, ACTL6A and ACTL6B, and PBRM1.

In the present invention, references to ARID1A denote AT-rich interaction domain 1A, having the HGNC ID: 11110. The HUGO Gene Symbol report for ARID1A can be found at: http://www.genenames.org/cgi-bin/gene symbol report?hgnc id=HGNC:11110 which provides links to the ARID1A nucleic acid and amino acid sequences, as well as reference to the homologous murine and rat proteins. ARID1A is located in 1p36.11 [15], a region frequently deleted in human cancers [17].

In the present invention, references to ARID1B denote AT-rich interaction domain 1B, having the HGNC ID: 18040. The HUGO Gene Symbol report for ARID1B can be found at: http://www.genenames.org/cgi-bin/gene symbol report?hgnc id=HGNC:18040 which provides links to the ARID1B nucleic acid and amino acid sequences, as well as reference to the homologous murine and rat proteins.

In the present invention, references to ARID2 denote AT-rich interaction domain 2, having the HGNC ID: 18037. The HUGO Gene Symbol report for ARID2 can be found at: http://www.genenames.org/cgi-bin/gene symbol report? hgnc id=HGNC:18037 which provides links to the ARID2 nucleic acid and amino acid sequences, as well as reference to the homologous murine and rat proteins In the present invention, references to SMARCA2 denote SWI/SNF related, matrix associated, actin dependent regulator of chromatin, subfamily a member 2, having the HGNC ID: 11098. The HUGO Gene Symbol report for SMARCA2 can be found at: http://www.genenames.org/cgi-bin/gene symbol report?hgnc id=HGNC:11098 which provides links to the SMARCA2 nucleic acid and amino acid sequences, as well as reference to the homologous murine and rat proteins In the present invention, references to SMARCA4 denote SWI/SNF related, matrix associated, actin dependent regulator of chromatin, subfamily a member 4, having the HGNC ID: 11100. The HUGO Gene Symbol report for SMARCA4 can be found at: http://www.genenames.org/cgi-bin/gene symbol report?hgnc id=HGNC:11100 which provides links to the SMARCA4 nucleic acid and amino acid sequences, as well as reference to the homologous murine and rat proteins In the present invention, references to SMARCB1 denote SWI/SNF related, matrix associated, actin dependent regulator of chromatin, subfamily b member 1, having the HGNC ID: 11103. The HUGO Gene Symbol report for SMARCB1 can be found at: http://www.genenames.org/cgi-bin/gene symbol report?hgnc id=HGNC:11103 which provides links to the SMARCB1 nucleic acid and amino acid sequences, as well as reference to the homologous murine and rat proteins In the present invention, references to SMARCC1 denote SWI/SNF related, matrix associated, actin dependent regulator of chromatin, subfamily c member 1, having the HGNC ID: 11104. The HUGO Gene Symbol report for SMARCC1 can be found at: http://www.genenames.org/cgi-bin/gene symbol report?hgnc id=HGNC:11104 which provides links to the SMARCC1 nucleic acid and amino acid sequences, as well as reference to the homologous murine and rat proteins In the present invention, references to SMARCC2 denote SWI/SNF related, matrix associated, actin dependent regulator of chromatin, subfamily c member 2, having the HGNC ID: 11105. The HUGO Gene Symbol report for SMARCC2 can be found at: http://www.genenames.org/cgi-bin/gene symbol report?hgnc id=HGNC:11105 which provides links to the SMARCC2 nucleic acid and amino acid sequences, as well as reference to the homologous murine and rat proteins In the present invention, references to SMARCD1 denote SWI/SNF related, matrix associated, actin dependent regulator of chromatin, subfamily d member 1, having the HGNC ID: 11106. The HUGO Gene Symbol report for SMARCD1 can be found at: http://www.genenames.org/cgi-bin/gene symbol report?hgnc id=HGNC:11106 which provides links to the SMARCD1 nucleic acid and amino acid sequences, as well as reference to the homologous murine and rat proteins.

In the present invention, references to SMARCD2 denote SWI/SNF related, matrix associated, actin dependent regulator of chromatin, subfamily d member 2, having the HGNC ID: 11107. The HUGO Gene Symbol report for SMARCD2 can be found at: http://www.genenames.org/cgi-bin/gene symbol report?hgnc id=HGNC:11107 which provides links to the SMARCD2 nucleic acid and amino acid sequences, as well as reference to the homologous murine and rat proteins In the present invention, references to SMARCD3 denote SWI/SNF related, matrix associated, actin dependent regulator of chromatin, subfamily d member 3, having the HGNC ID: 11108. The HUGO Gene Symbol report for SMARCD3 can be found at: http://www.genenames.org/cgi-bin/gene symbol report?hgnc id=HGNC:11108 which provides links to the SMARCD3 nucleic acid and amino acid sequences, as well as reference to the homologous murine and rat proteins In the present invention, references to SMARCE1 denote SWI/SNF related, matrix associated, actin dependent regulator of chromatin, subfamily e member 1, having the HGNC ID: 11109. The HUGO Gene Symbol report for SMARCE1 can be found at: http://www.genenames.org/cgi-bin/gene symbol report?hgnc id=HGNC:11109 which provides links to the SMARCE1 nucleic acid and amino acid sequences, as well as reference to the homologous murine and rat proteins In the present invention, references to ACTL6A denote actin like 6A, having the HGNC ID: 24124. The HUGO Gene Symbol report for ACTL6A can be found at: http://www.genenames.org/cgi-bin/gene symbol report?hgnc id=HGNC:24124 which provides links to the ACTL6A nucleic acid and amino acid sequences, as well as reference to the homologous murine and rat proteins In the present invention, references to ACTL6B denote actin like 6A, having the HGNC ID: 160. The HUGO Gene Symbol report for ACTL6B can be found at: http://www-.genenames.org/cgi-bin/gene symbol report?hgnc id=HGNC:160 which provides links to the ACTL6B nucleic acid and amino acid sequences, as well as reference to the homologous murine and rat proteins In the present invention, references to PBRM1 denote polybromo 1, having the HGNC ID: 30064. The HUGO Gene Symbol report for PBRM1 can be found at: http://www.genenames.org/cgi-bin/gene symbol report?hgnc id=HGNC:30064 which provides links to the PBRM1 nucleic acid and amino acid sequences, as well as reference to the homologous murine and rat proteins Cancers with Gene Translocation Defects in the Following Genes Associated with Synovial Sarcomas Synovial sarcoma (SS) is an aggressive and difficult to treat type of soft tissue sarcoma that predominantly affects adolescents and young adults (AYAs). SS has a poor outcome and limited treatment options (Nielsen, Poulin et al. 2015), but in most cases, localised SS is treated with surgery, sometimes in combination with chemo- or radiotherapy. Chemotherapy in this setting usually consists of doxorubicin or ifosfamide (Spurrell, Fisher et al. 2005) Patients with advanced metastatic SS have a particularly poor long-term survival rate. For example, those with distant metastases have a 10-year survival rate of only 8.9% compared to 69% for patients with localized tumours (Sultan, Rodriguez-Galindo et al. 2009). Taken together, these factors highlight that additional and more specific, targeted therapeutic approaches to SS are required to effectively manage this disease.

As translocations in genes associated with synovial sarcomas are known to also cause BAF-complex defects, the present invention extends to the treatment of synovial sarcomas with ATR inhibitors, as demonstrated by experiments in which cells lines containing such gene translocation defects are sensitive to ATR inhibitors. The experiments demonstrate that this effect is generic as the cell lines are sensitive to ssRNAi molecules that target Ataxia-Telangiectasia Mutated and Rad3-related protein kinase (ATR).

The overwhelming majority of SS are characterised by a t (X;18) chromosomal translocation, which is used as a diagnostic biomarker for the disease (Clark, Rocques et al. 1994). In SS, t (X;18) translocations fuse the first 10 exons of the SS18 gene (synovial sarcoma translocation, chromosome 18) gene to the last three exons of one of the SSX (synovial sarcoma, X breakpoint) family of genes, SSX1, SSX2 or SSX4 (Clark, Rocques et al. 1994, Amary, Berisha et al. 2007). These translocations encode either SS18-SSX1, SS18-SSX2, or SS18-SSX4 fusion proteins, each of which appears sufficient to drive tumour development. For example, either SS18-SSX1 or SS18-SSX2 is sufficient to give rise to tumours with 100% penetrance when expressed in cells of the Myf5 myoblast lineage in transgenic mice (Haldar, Hancock et al. 2007, Jones, Barrott et al. 2016). Cytogenetically, SS tumours display remarkably few recurrent mutations in addition to the SS18-SSX translocation (Vlenterie, Hillebrandt et al. 2015), supporting the hypothesis that tumorigenesis is driven by the fusion gene alone. Several studies have demonstrated that SS tumours display genomic instability, which appears to be more common in adult patients and those with advanced, metastatic disease (Lagarde, Przybyl et al. 2013, Pryzbyl, Sciot et al 2014, Vlenterie, Hillebrandt et al. 2015).

Although SS18 and SSX proteins do not contain any known DNA binding domains, both wild-type proteins are involved in regulation of transcription (de Bruijn, Allander et al. 2006, Garcia, Shaffer et al. 2012, Garcia, Shaffer et al. 2012, Kadoch and Crabtree 2013). In part at least, the transcriptional functions of SS18 might be related to its role as a part of the BAF SWI/SNF complex (Thaete, Brett et al. 1999, Nagai, Tanaka et al. 2001). The BAF complex mediates nucleosome remodelling via an ATP-dependent process that is thought to control transcription (Wilson and Roberts 2011, Smith-Roe, Nakamura et al. 2015), but also has roles in a variety of other processes including DNA repair (Shen, Peng et al. 2015, Smith-Roe, Nakamura et al. 2015). Wild type SS18 protein interacts with multiple other elements of the BAF complex, including SMARCA4, ARID1A and SMARCB1. Alterations in these interactions caused by SS18-SSX fusions might also play a role in the pathogenesis of synovial sarcoma (Middeljans, Wan et al. 2012, Kadoch and Crabtree 2013). For example, SS18-SSX1 fusion proteins interact with BAF, but displace wild-type SS18 protein and an additional BAF component, SMARCB1 from BAF complexes (Kadoch and Crabtree 2013).

The displacement of SMARCB1 from BAF leads to its proteasomal degradation, with reduced levels of BAF-associated SMARCB1 being a characteristic of synovial sarcoma cell lines and tumours (Kadoch and Crabtree 2013, Ito, Asano et al. 2015). Loss of SMARCB1 from BAF complexes is also associated with altered regulation of gene expression. For example, in primary human neonatal fibroblast cells, expression of SS18-SSX1 and the subsequent loss of SMARCB1 causes eviction of repressive polycomb complexes from the promoter for the SOX2 gene (Sex determining region Y-box 2) which encodes an SRY-related HMG-box (SOX) family transcription factor (Kadoch and Crabtree 2013). This causes increased SOX2 expression, which is required for synovial sarcoma cell survival (Kadoch and Crabtree 2013). Interestingly, homozygous mutation or deletion of SMARCB1 is the only observed cytogenetic abnormality in malignant rhabdoid tumours (MRT) (Versteege, Sevenet et al. 1998, McKenna, Sansam et al. 2008); suggesting SMARCB1 can act as a tumour suppressor gene. Multiple other BAF complex encoding genes have also been implicated in cancer pathogenesis including ARID1A and SMARCA4, and it has recently been suggested that BAF complex mutations may exist in as many as 20% of human cancers (Kadoch, Hargreaves et al. 2013).

Preferred examples of gene translocation defects associated with synovial sarcoma include defects in SSX1, SSX2 and SS18.

In the present invention, references to SSX1 denote synovial sarcoma, X breakpoint 1, having the HGNC ID:11335. The HUGO Gene Symbol report for SSX1 can be found at: http://www.genenames.org/cgi-bin/gene symbol report?hgnc id=HGNC:11335 which provides links to the SSX1 nucleic acid and amino acid sequences, as well as reference to the homologous murine and rat proteins.

In the present invention, references to SSX2 denote synovial sarcoma, X breakpoint 2, having the HGNC ID:11336. The HUGO Gene Symbol report for SSX2 can be found at: http://www.genenames.org/cgi-bin/gene symbol report?hgnc id=HGNC:11336 which provides links to the SSX2 nucleic acid and amino acid sequences, as well as reference to the homologous murine and rat proteins.

In the present invention, references to SS18 denote synovial sarcoma translocation, chromosome 18, having the HGNC ID:11340. The HUGO Gene Symbol report for SS18 can be found at: http://www.genenames.org/cgi-bin/gene symbol report?hgnc id=HGNC:11340 which provides links to the SS18 nucleic acid and amino acid sequences, as well as reference to the homologous murine and rat proteins. SS18 is a dedicated and stable subunit of BAF complexes, aberrant forms of which result in dysfunctional BAF-complexes that progress proliferation in synovial sarcoma (Kadoch et al., "Reversible Disruption of mSWI/SNF (BAF) Complexes by the SS18-SSX Oncogenic Fusion in Synovial Sarcoma." *Cell* 153.1 (2013): 71-85. PMC. Web. 8 Jan. 2016.)

Cancers with defects (loss of function mutations, loss of expression) in the following genes associated with synovial sarcomas:

In the present invention, references to SSX1 denote synovial sarcoma, X breakpoint 1, having the HGNC ID:11335. The HUGO Gene Symbol report for SSX1 can be found at: http://www.genenames.org/cgi-bin/gene symbol report?hgnc id=HGNC:11335 which provides links to the SSX1 nucleic acid and amino acid sequences, as well as reference to the homologous murine and rat proteins.

In the present invention, references to SSX2 denote synovial sarcoma, X breakpoint 2, having the HGNC ID:11336. The HUGO Gene Symbol report for SSX2 can be found at: http://www.genenames.org/cgi-bin/gene symbol report?hgnc id=HGNC:11336 which provides links to the SSX2 nucleic acid and amino acid sequences, as well as reference to the homologous murine and rat proteins.

By a similar rationale, cancers with defects (loss of function mutations, loss of expression) in genes associated with synovial sarcomas may also be targeted with Ataxia-Telangiectasia Mutated and Rad3-related protein kinase (ATR) inhibitors (ATRi), in particular genes with defects associated with synovial sarcoma, such as SSX1 and SSX2. In particular the defect may be a translocation encoding an SS18-SSX1 or SS18-SSX2 fusion.

Inhibitors

In the present invention, Ataxia-Telangiectasia Mutated and Rad3-related protein kinase (ATR) inhibitors (ATRi) refer to compounds or substances that inhibit the expression levels or kinase activity of ATR, which may be employed or screened for use as ATR inhibitors in accordance with the present invention for treating BAF-complex gene mutated or deficient cancer. Some inhibitors are known and further examples may be found by the application of screening technologies to these targets.

ATR inhibiting compounds may be small molecules, peptide fragments, antibodies or fragments thereof, or siRNAs. Examples of ATRi compounds include, but are not limited to: AZ20, BEZ235 (NVP-BEZ235, dactolisib), ETP-46464, VE-821, VE-822 (VX-970), AZD6738, NU6027, CP-466722, CGK733, KU-60019, KU-55933, Schisandrin B, and Mirin. In particular, the data provided herein suggests that small molecule inhibitors or siRNA targeting ATR are capable of causing a generic anti-cancer effect in types of cancer mutated or deficient in one or more BAF complex genes. Alternatively, the inhibitor may comprise an antibody, or fragment thereof, with neutralising activity.

Small Molecule Inhibitors

Examples of small molecule compounds which are ATR inhibitors and which may be used in accordance with the invention are as follows.

In the present invention references to AZ20 denote 4-cyclohexylmethoxy-5-nitrosopyrimidine-2,6-diamine, having the ChemSpider ID: 29361340. The ChemSpider report for AZ20, as well as the structure, can be found at: http://www.chemspider.com/Chemical-Structure.29361340.html. AZ20 is a selective inhibitor of ATR kinase with in vivo anti-tumour activity (23).

In the present invention references to BEZ235 (NVP-BEZ235, dactolisib) denote 2-Methyl-2-{4-(3-methyl-2-oxo-8-(3-quinolinyl)-2,3-dihydro-1H-imidazo(4,5-c)quinolin-1-yl)phenyl}propanenitrile, having the ChemSpider ID: 10151099. The ChemSpider report for BEZ235, as well as the structure, can be found at: http://www.chemspider.com/Chemical-Structure.10151099.html. Originally developed as dual PI3K/MTOR inhibitor, BEZ235 also possesses substantial activity against ATR (25).

In the present invention references to ETP-46464 denote 2-Methyl-2-{4-(2-oxo-9-(3-quinolinyl)-2H-(1,3)oxazino(5,4-c)quinolin-1(4H)-yl)phenyl}propanenitrile having the ChemSpider ID: 29785252. The ChemSpider report for ETP-46464, as well as the structure, can be found at: http://www.chemspider.com/Chemical-Structure.29785252.html. ETP-46464 is an inhibitor of ATR kinase activity (25).

In the present invention references to VE-821 denote 3-amino-6-(4-methylsulfonylphenyl)-N-phenyl-pyrazine-2-carboxamide having the ChemSpider ID: 25991555. The ChemSpider report for VE-821, as well as the structure, can be found at: http://www.chemspider.com/Chemical-Structure.25991555.html. VE-821 is an inhibitor of ATR kinase that potentiates the cytotoxic effects of a number of DNA damaging agents (6-9).

In the present invention references to VE-822 (VX-970) denote 5-[4-(Isopropylsulfonyl)phenyl]-3-(3-{4-[(methyl-amino)methyl]phenyl}-1,2-oxazol-5-yl)-2-pyrazinamine having the ChemSpider ID: 30773968. The ChemSpider report for VE-822, as well as the structure, can be found at: http://www.chemspider.com/Chemical-Structure.30773968.html. VE-822 is a specific and potent inhibitor of ATR currently in Phase I clinical trials (6).

In the present invention references to AZD6738 denote 6-[5-(3-Cyano-5-fluorophenyl)-1,2,4-oxadiazol-3-yl]nicotinonitrile having the ChemSpider ID: 8054780. The ChemSpider report for AZD6538, as well as the structure, can be found at: http://www.chemspider.com/Chemical-Structure.8054780.html. As an analogue of AZ20 with improved solubility, pharmacodynamics and bioavailability, AZF6738 is potent and selective ATR inhibitor (26).

In the present invention references to NU6027 denote 4-cyclohexylmethoxy-5-nitrosopyrimidine-2,6-diamine having the ChemSpider ID: 352956. The ChemSpider report for NU60727, well as the structure, can be found at: http://www.chemspider.com/Chemical-Structure.352956.html. NU6027 was originally developed as CDK2 inhibitor, but also potently inhibits ATR activity (27).

In the present invention references to CP-466722 denote 1-(6,7-Dimethoxy-4-quinazolinyl)-3-(2-pyridinyl)-1H-1,2,4-triazol-5-amine, having the ChemSpider ID: 27445283. The ChemSpider report for CP-466722, as well as the structure, can be found at: http://www.chemspider.com/Chemical-Structure.27445283.html.

In the present invention references to CGK733 denote 2,2-Diphenyl-N-(2,2,2-trichloro-1-{[(4-fluoro-3-nitrophenyl)carbamothioyl]amino}ethyl)acetamide having the ChemSpider ID: 5037512. The ChemSpider report for CGK733, well as the structure, can be found at: http://www.chemspider.com/Chemical-Structure.5037512.html. CGK733 was originally identified as an inhibitor of ATM and ATR and has been show to suppress cyclin D1 levels and inhibit cell proliferation [28].

In the present invention references to KU-60019 denote 2-[(2R,6S)-2,6-dimethylmorpholin-4-yl]-N-[5-[4-oxo-6-(1-piperidyl)pyran-2-yl]-9H-thioxanthen-2-yl]acetamide, having the ChemSpider ID: 28294997. The ChemSpider report for KU-60019, as well as the structure, can be found at: http://www.chemspider.com/Chemical-Structure.28294997.html.

In the present invention references to KU-55933 denote 2-(Morpholin-4-yl)-6-(thianthren-1-yl)-4H-pyran-4-one, having the ChemSpider ID: 4442218. The ChemSpider report for KU-55933, as well as the structure, can be found at: http://www.chemspider.com/Chemical-Structure.4442218.html.

In the present invention references to Mirin denote 4-Thiazolidinone, 5-(p-hydroxybenzylidene)-2-imino-, having the ChemSpider ID: 1016643. The ChemSpider report for Mirin, as well as the structure, can be found at: http://www.chemspider.com/Chemical-Structure.1016643.html.

In the present invention references to Schisandrin B denote 1,2,3,13-Tetramethoxy-6,7-dimethyl-5,6,7,8-tetrahydrobenzo[3',4']cycloocta[1',2':4,5]benzo[1,2-d][1,3]dioxole having the ChemSpider ID 97221.

The ChemSpider report for Schisandrin B, well as the structure, can be found at: http://www.chemspider.com/Chemical-Structure.97221.html. Schisandrin B is a selective inhibitor of ATR (29)

Another class of inhibitors are compounds of the formulae herein, including Formula A (i.e., Formula A-I, A-I-a, A-II, A-II-a, etc.) or a compound of any of the formulae herein.

In some embodiments, the compound that inhibits ATR is represented by Formula A-I:

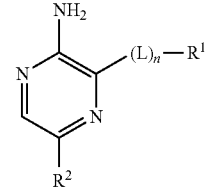

A-I or a pharmaceutically acceptable salt thereof,
wherein:
$R^1$ is a 5-6 membered monocyclic aryl or heteroaryl ring having 0-4 heteroatoms independently selected from nitrogen, oxygen, or sulfur, wherein said monocyclic aryl or heteroaryl ring is optionally fused to another ring to form an 8-10 membered bicyclic aryl or heteroaryl ring having 0-6 heteroatoms independently selected from nitrogen, oxygen, or sulfur; each $R^1$ is optionally substituted with 1-5 $J^1$ groups;
$R^2$ is a 5-6 membered monocyclic aryl or heteroaryl ring having 0-3 heteroatoms independently selected from nitrogen, oxygen, or sulfur, wherein said monocyclic aryl or heteroaryl ring is optionally fused to another ring to form an 8-10 membered bicyclic aryl or heteroaryl ring having 0-4 heteroatoms independently selected from nitrogen, oxygen, or sulfur; each $R^2$ is optionally substituted with 1-5 $J^2$ groups;
L is —C(O)NH— or —C(O)N($C_{1-6}$alkyl)-;
n is 0 or 1;
each $J^1$ and $J^2$ is independently halo, —CN, —NO$_2$, —V$^1$-R, or —(V$^2$)$_m$-Q;
$V^1$ is a $C_{1-10}$ aliphatic chain wherein 0-3 methylene units are optionally and independently replaced with O, NR", S, C(O), S(O), or S(O)$_2$; $V^1$ is optionally substituted with 1-6 occurrences of $J^{V1}$;
$V^2$ is a $C_{1-10}$ aliphatic chain wherein 0-3 methylene units are optionally and independently replaced with O, NR", S, C(O), S(O), or S(O)$_2$; $V^2$ is optionally substituted with 1-6 occurrences of $J^{V2}$;
m is 0 or 1;
Q is a 3-8 membered saturated or unsaturated monocyclic ring having 0-4 heteroatoms independently selected from nitrogen, oxygen, or sulfur, or a 9-10 membered saturated or unsaturated bicyclic ring having 0-6 heteroatoms independently selected from nitrogen, oxygen, or sulfur; each Q is optionally substituted with 0-5 $J^Q$;
each $J^{V1}$ or $J^{V2}$ is independently halogen, CN, NH$_2$, NO$_2$, $C_{1-4}$aliphatic, NH($C_{1-4}$aliphatic), N($C_{1-4}$aliphatic)$_2$, OH, O(C$_{1-4}$aliphatic), CO$_2$H, CO$_2$(C$_{1-4}$aliphatic), C(O)NH$_2$, C(O)NH(C$_{1-4}$aliphatic), C(O)N(C$_{1-4}$aliphatic)$_2$, NHCO(C$_{1-4}$aliphatic), N(C$_{1-4}$aliphatic)CO(C$_{1-4}$aliphatic), SO$_2$(C$_{1-4}$aliphatic), NHSO$_2$(C$_{1-4}$aliphatic), or N(C$_{1-4}$aliphatic)SO$_2$(C$_{1-4}$aliphatic), wherein said C$_{1-4}$aliphatic is optionally substituted with halo;

R is H or C$_{1-6}$aliphatic wherein said C$_{1-6}$aliphatic is optionally substituted with 1-4 occurrences of NH$_2$, NH(C$_{1-4}$aliphatic), N(C$_{1-4}$aliphatic)$_2$, halogen, C$_{1-4}$aliphatic, OH, O(C$_{1-4}$aliphatic), NO$_2$, CN, CO$_2$H, CO$_2$(C$_{1-4}$aliphatic), CO(C$_{1-4}$aliphatic), O(haloC$_{1-4}$aliphatic), or haloC$_{1-4}$aliphatic;

each J$^Q$ is independently halo, oxo, CN, NO$_2$, X-R, or —(X)$_p$-Q$^4$;

p is 0 or 1;

X is C$_{1-10}$aliphatic; wherein 1-3 methylene units of said C$_{1-6}$aliphatic are optionally replaced with —NR, —O—, —S—, C(O), S(O)$_2$, or S(O); wherein X is optionally and independently substituted with 1-4 occurrences of NH$_2$, NH(C$_{1-4}$aliphatic), N(C$_{1-4}$aliphatic)$_2$, halogen, C$_{1-4}$aliphatic, OH, O(C$_{1-4}$aliphatic), NO$_2$, CN, CO(C$_{1-4}$aliphatic), CO$_2$H, CO$_2$(C$_{1-4}$aliphatic), C(O)NH$_2$, C(O)NH(C$_{1-4}$aliphatic), C(O)N(C$_{1-4}$ aliphatic)$_2$, SO(C$_{1-4}$aliphatic), SO$_2$(C$_{1-4}$aliphatic), SO$_2$NH(C$_{1-4}$aliphatic), SO$_2$N(C$_{1-4}$aliphatic)$_2$, NHC(O)(C$_{1-4}$aliphatic), N(C$_{1-4}$aliphatic)C(O)(C$_{1-4}$aliphatic), wherein said C$_{1-4}$aliphatic is optionally substituted with 1-3 occurrences of halo;

Q$^4$ is a 3-8 membered saturated or unsaturated monocyclic ring having 0-4 heteroatoms independently selected from nitrogen, oxygen, or sulfur, or a 8-10 membered saturated or unsaturated bicyclic ring having 0-6 heteroatoms independently selected from nitrogen, oxygen, or sulfur; each Q$^4$ is optionally substituted with 1-5 J$^{Q4}$;

J$^{Q4}$ is halo, CN, or C$_{1-4}$alkyl wherein up to 2 methylene units are optionally replaced with O, NR*, S, C(O), S(O), or S(O)$_2$;

R is H or C$_{1-4}$alkyl wherein said C$_{1-4}$alkyl is optionally substituted with 1-4 halo;

R', R", and R* are each independently H, C$_{1-4}$alkyl, or is absent; wherein said C$_{1-4}$alkyl is optionally substituted with 1-4 halo.

In some embodiments, the compound that inhibits ATR is Compound A-1:

Compound A-1

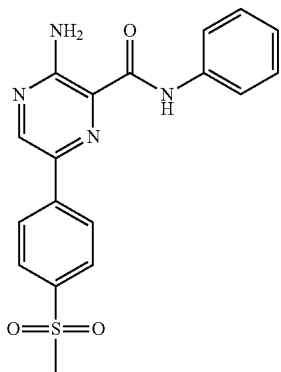

or a pharmaceutically acceptable salt thereof.

In some embodiments, the compound that inhibits ATR is represented by Formula AI-a:

A-I-a

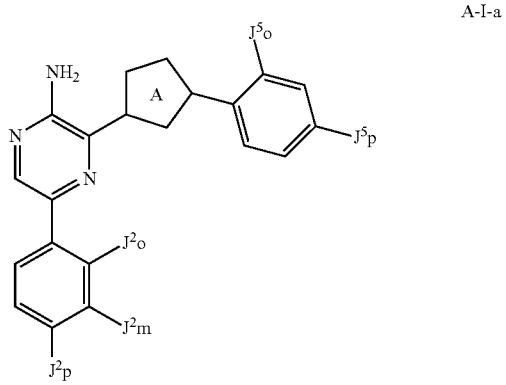

or a pharmaceutically acceptable salt thereof;

wherein:

Ring A is

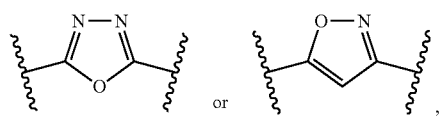 [SMILES: *c1nnc(*)o1 ; *c1cc(*)on1]

J$^5$o is H, F, Cl, C$_{1-4}$aliphatic, O(C$_{1-3}$aliphatic), or OH;

J$^5$p is

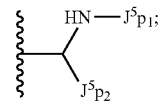

J$^5$p1 is H, C$_{1-4}$aliphatic, oxetanyl, tetrahydrofuranyl, tetrahydropyranyl; wherein J$^5$p1 is optionally substituted with 1-2 occurrences of OH or halo;

J$^5$p2 is H, methyl, ethyl, CH$_2$F, CF$_3$, or CH$_2$OH;

J$^2$o is H, CN, or SO$_2$CH$_3$;

J$^2$m is H, F, Cl, or methyl;

J$^2$p is —SO$_2$(C$_{1-6}$alkyl), —SO$_2$(C$_{3-6}$cycloalkyl), —SO$_2$(4-6 membered heterocyclyl), —SO$_2$(C$_{1-4}$alkyl)N(C$_{1-4}$alkyl)$_2$, or —SO$_2$(C$_{1-4}$alkyl)-(4-6 membered heterocyclyl), wherein said heterocyclyl contains 1 heteroatom selected from oxygen, nitrogen, or sulfur; and wherein said J$^2$p is optionally substituted with 1-3 occurrences halo, OH, or O(C$_{1-4}$alkyl).

In some embodiments, Ring A is

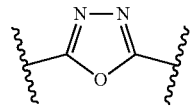

In some embodiments, Ring A is

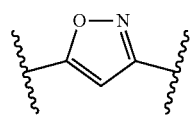

In some embodiments, the compound that inhibits ATR is Compound A-2:

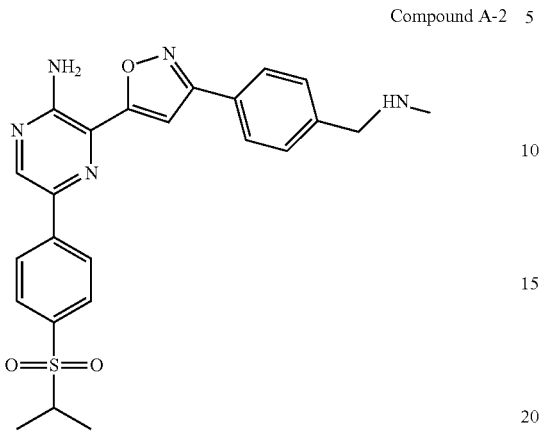

Compound A-2 or a pharmaceutically acceptable salt thereof.

In some embodiments, the compound that inhibits ATR is represented by Formula A-II:

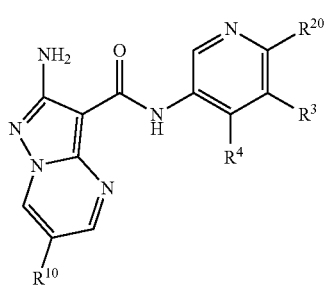

A-II or a pharmaceutically salt thereof,
wherein:
$R^{10}$ is independently selected from fluoro, chloro, or —C($J^{10}$)$_2$CN;
$J^{10}$ is independently selected from H or $C_{1-2}$alkyl; or
two occurrences of $J^{10}$, together with the carbon atom to which they are attached, form a 3-4 membered optionally substituted carbocyclic ring;
$R^{20}$ is independently selected from H; halo; —CN; NH$_2$; a $C_{1-2}$alkyl optionally substituted with 0-3 occurrences of fluoro; or a $C_{1-3}$aliphatic chain wherein up to two methylene units of the aliphatic chain are optionally replaced with —O—, —NR$^a$—, —C(O)—, or —S(O)$_z$;
$R^3$ is independently selected from H; halo; $C_{1-4}$alkyl optionally substituted with 1-3 occurrences of halo; $C_{3-4}$cycloalkyl; —CN; or a $C_{1-3}$aliphatic chain wherein up to two methylene units of the aliphatic chain are optionally replaced with —O—, —NR$^a$—, —C(O)—, or —S(O)$_z$;
$R^4$ is independently selected from $Q^1$ or a $C_{1-10}$aliphatic chain wherein up to four methylene units of the aliphatic chain are optionally replaced with —O—, —NR$^a$—, —C(O)—, or —S(O)$_z$—; each $R^4$ is optionally substituted with 0-5 occurrences of $J^{Q1}$; or
$R^3$ and $R^4$, taken together with the atoms to which they are bound, form a 5-6 membered aromatic or non-aromatic ring having 0-2 heteroatoms selected from oxygen, nitrogen or sulfur; the ring formed by $R^3$ and $R^4$ is optionally substituted with 0-3 occurrences of $J^Z$;
$Q^1$ is independently selected from a 3-7 membered fully saturated, partially unsaturated, or aromatic monocyclic ring, the 3-7 membered ring having 0-3 heteroatoms selected from oxygen, nitrogen or sulfur; or an 7-12 membered fully saturated, partially unsaturated, or aromatic bicyclic ring having 0-5 heteroatoms selected from oxygen, nitrogen, or sulfur;
$J^z$ is independently selected from $C_{1-6}$aliphatic, =O, halo, or →O;
$J^{Q1}$ is independently selected from —CN; halo; =O; $Q^2$; or a $C_{1-8}$aliphatic chain wherein up to three methylene units of the aliphatic chain are optionally replaced with —O—, —NR$^a$—, —C(O)—, or —S(O)$_z$—; each occurrence of $J^{Q1}$ is optionally substituted by 0-3 occurrences of $J^R$; or
two occurrences of $J^{Q1}$ on the same atom, taken together with the atom to which they are joined, form a 3-6 membered ring having 0-2 heteroatoms selected from oxygen, nitrogen, or sulfur; wherein the ring formed by two occurrences of $J^{Q1}$ is optionally substituted with 0-3 occurrences of $J^X$; or
two occurrences of $J^{Q1}$, together with $Q^1$, form a 6-10 membered saturated or partially unsaturated bridged ring system;
$Q^2$ is independently selected from a 3-7 membered fully saturated, partially unsaturated, or aromatic monocyclic ring having 0-3 heteroatoms selected from oxygen, nitrogen, or sulfur; or an 7-12 membered fully saturated, partially unsaturated, or aromatic bicyclic ring having 0-5 heteroatoms selected from oxygen, nitrogen, or sulfur;
$J^R$ is independently selected from —CN; halo; =O; →O; $Q^3$; or a $C_{1-6}$aliphatic chain wherein up to three methylene units of the aliphatic chain are optionally replaced with —O—, —NR$^a$—, —C(O)—, or —S(O)$_z$—; each $J^R$ is optionally substituted with 0-3 occurrences of $J^T$; or
two occurrences of $J^R$ on the same atom, together with the atom to which they are joined, form a 3-6 membered ring having 0-2 heteroatoms selected from oxygen, nitrogen, or sulfur; wherein the ring formed by two occurrences of $J^R$ is optionally substituted with 0-3 occurrences of $J^X$; or
two occurrences of $J^R$, together with $Q^2$, form a 6-10 membered saturated or partially unsaturated bridged ring system;
$Q^3$ is a 3-7 membered fully saturated, partially unsaturated, or aromatic monocyclic ring having 0-3 heteroatoms selected from oxygen, nitrogen, or sulfur; or an 7-12 membered fully saturated, partially unsaturated, or aromatic bicyclic ring having 0-5 heteroatoms selected from oxygen, nitrogen, or sulfur;
$J^X$ is independently selected from —CN; =O; halo; or a $C_{1-4}$aliphatic chain wherein up to two methylene units of the aliphatic chain are optionally replaced with —O—, —NR$^a$—, —C(O)—, or —S(O)$_z$—;
$J^T$ is independently selected from halo, —CN; →O; =O; —OH; a $C_{1-6}$aliphatic chain wherein up to two methylene units of the aliphatic chain are optionally replaced with —O—, —NR$^a$—, —C(O)—, or —S(O)$_z$—; or a 3-6 membered non-aromatic ring having 0-2 heteroatoms selected from oxygen, nitrogen, or sulfur; each occurrence of $J^T$ is optionally substituted with 0-3 occurrences of $J^M$; or two occurrences of $J^T$ on the same atom, together with the atom to which they are joined, form a 3-6 membered ring having 0-2 heteroatoms selected from oxygen, nitrogen, or sulfur; or two occurrences of $J^T$, together with $Q^3$, form a 6-10 membered saturated or partially unsaturated bridged ring system;

$J^M$ is independently selected from halo or $C_{1-6}$aliphatic;

J is H or Cl;

z is 0, 1 or 2; and $R^a$ is independently selected from H or $C_{1-4}$aliphatic.

In some embodiments, $R^1$ and $R^3$ are fluoro. In some embodiments, $R^4$ is $Q^1$. In some embodiments, $Q^1$ is independently selected from piperidinyl and imidazolyl.

In some embodiments, the compound that inhibits ATR is Compound A-3:

Compound A-3 or a pharmaceutically acceptable salt thereof.

In some embodiments, the compound that inhibits ATR is represented by Formula A-II-a:

A-II-a or a pharmaceutically acceptable salt thereof, wherein:

$R^{10}$ is independently selected from fluoro, chloro, or —C($J^{10}$)$_2$CN;

$J^{10}$ is independently selected from H or $C_{1-2}$alkyl; or two occurrences of $J^1$, together with the carbon atom to which they are attached, form an optionally substituted 3-4 membered carbocyclic ring;

$R^3$ is independently selected from H; chloro; fluoro; $C_{1-4}$alkyl optionally substituted with 1-3 occurrences of halo; $C_{3-4}$cycloalkyl; —CN; or a $C_{1-3}$aliphatic chain wherein up to two methylene units of the aliphatic chain are optionally replaced with —O-, —NR$^a$—, —C(O)—, or —S(O)$_z$;

$L^1$ is H; a 3-7 membered aromatic or non-aromatic ring having 0-2 heteroatoms selected from oxygen nitrogen or sulfur; or a $C_{1-6}$aliphatic chain wherein up to two methylene units of the aliphatic chain are optionally replaced with —O—, —NR$^a$—, —C(O)—, or —S(O)$_z$; each $L^1$ is optionally substituted with $C_{1-4}$aliphatic; —CN; halo; —OH; or a 3-6 membered non-aromatic ring having 0-2 heteroatoms selected from oxygen, nitrogen, or sulfur;

$L^2$ is H; a 3-7 membered aromatic or non-aromatic ring having 0-2 heteroatoms selected from oxygen nitrogen or sulfur; or a $C_{1-6}$aliphatic chain wherein up to two methylene units of the aliphatic chain are optionally replaced with —O—, —NR$^a$—, —C(O)—, or —S(O)$_z$; each $L^2$ is optionally substituted with $C_{1-4}$aliphatic; —CN; halo; —OH; or a 3-6 membered non-aromatic ring having 0-2 heteroatoms selected from oxygen, nitrogen, or sulfur; or $L^1$ and $L^2$, together with the nitrogen to which they are attached, form a Ring D; Ring D is optionally substituted with 0-5 occurrences of $J^G$;

$L^3$ is H; $C_{1-3}$aliphatic; or CN;

Ring D is independently selected from a 3-7 membered heterocyclyl ring having 1-2 heteroatoms selected from oxygen, nitrogen or sulfur; or an 7-12 membered fully saturated or partially unsaturated bicyclic ring having 1-5 heteroatoms selected from oxygen, nitrogen, or sulfur;

$J^G$ is independently selected from halo; —CN; —N(R$^o$)$_2$; →O; a 3-6 membered carbocycyl; a 3-6 membered heterocyclyl having 1-2 heteroatoms selected from oxygen nitrogen, or sulfur; or a $C_{1-4}$alkyl chain wherein up to two methylene units of the alkyl chain are optionally replaced with —O—, —NR$^a$—, —C(O)—, or —S(O)$_z$; each $J^G$ is optionally substituted with 0-2 occurrences of $J^K$.

two occurrences of $J^G$ on the same atom, together with the atom to which they are joined, form a 3-6 membered ring having 0-2 heteroatoms selected from oxygen, nitrogen, or sulfur; or two occurrences of $J^G$, together with Ring D, form a 6-10 membered saturated or partially unsaturated bridged ring system;

$J^K$ is a 3-7 membered aromatic or non-aromatic ring having 0-2 heteroatoms selected from oxygen, nitrogen, or sulfur;

z is 0, 1, or 2; and $R^a$ and $R^o$ are H or $C_{1-4}$alkyl.

In some embodiments, $R^1$ and $R^3$ are fluoro.

In some embodiments, the compound that inhibits ATR is Compound A-4:

Compound A-4 or a pharmaceutically acceptable salt thereof.

In some embodiments, the compound that inhibits ATR is:

Compound A-1

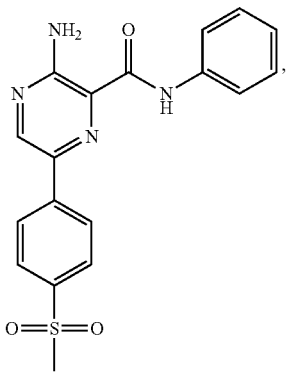

Compound A-2

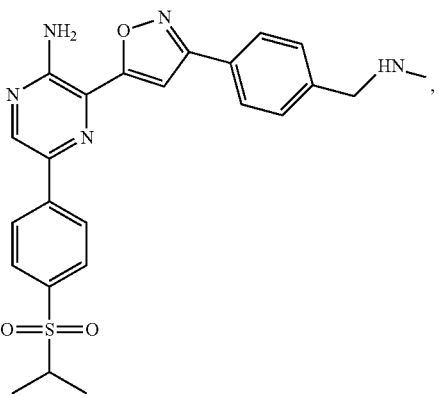

Compound A-3

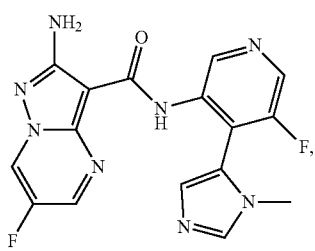

Compound A-4

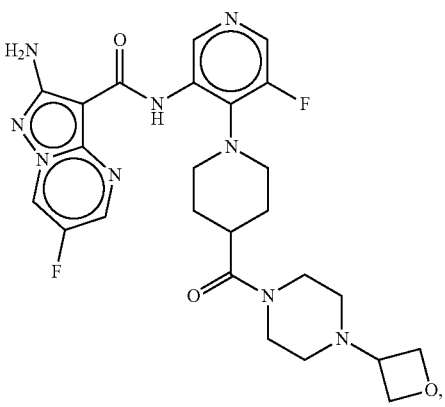

or a pharmaceutically acceptable salt thereof.

The ATR compounds described above can be prepared by any suitable methods known in the art, for example, WO 2015/187451, WO 2015/085132, WO 2014/089379, WO 2014/089379, WO 2014/143242, WO 2014/143241, WO 2015/084384, WO 2014/143240; WO 2013/071094; WO 2013/071093; WO 2013/071090; WO 2013/071088; WO 2013/049859; WO 2013/049719; WO 2013/049720; WO 2013/049722; WO 2013/071085; WO 2013/049726; WO 2012/178125; WO 2012/178124; WO 2012/178123; WO 2012/138938; WO 2012/138938; WO 2011/163527; WO 2011/143423; WO 2011/143426; WO 2011/143425; WO 2011/143422; WO 2011/143419; WO 2011/143399; WO 2010/054398; and WO 2010/071837.

Other examples of ATR inhibitors that may be utilized in the present invention may include those compounds described in WO 2015/187451, WO 2015/085132, WO 2015/187451, WO 2015/085132, WO 2014/089379, WO 2014/089379, WO 2014/143242, WO 2014/143241, WO 2015/084384, WO 2014/143240; WO 2014/089379, WO 2013/071094; WO 2013/071093; WO 2013/071090; WO 2013/071088; WO 2013/049859; WO 2013/049719; WO 2013/049720; WO 2013/049722; WO 2013/071085; WO 2013/049726; WO 2012/178125; WO 2012/178124; WO 2012/178123; WO 2012/138938; WO 2012/138938; WO 2011/163527; WO 2011/143423; WO 2011/143426; WO 2011/143425; WO 2011/143422; WO 2011/143419; WO 2011/143399; WO 2010/054398; and WO 2010/071837, all such compounds and compound formulae incorporated by reference herein.

For purposes of this application, it will be understood that when two occurrences of $J^Q$, together with $Q^1$, form a bridged ring system, the two occurrences of $J^Q$ are attached to separate atoms of $Q^1$. Additionally, when two occurrences of $J^R$, together with $Q^2$, form a bridged ring system, the two occurrences of $J^R$ are attached to separate atoms of $Q^2$. Moreover, when two occurrences of $J^T$, together with $Q^3$, form a bridged ring system, the two occurrence of $J^T$ are attached to separate atoms of $Q^3$. Further, when two occurrences of $J^W$, together with W, form a bridged ring system, the two occurences of $J^W$ are attached to separate atoms of W. Finally, when two occurrences of $J^G$, together with Ring D, form a bridged ring system, the two occurrences of $J^G$ are attached to separate atoms of Ring D.

It will be understood by those skilled in the art that the arrow in →O represents a dative bond.

Compounds of this invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed. Smith, M. B. and March, J., John Wiley & Sons, New York: 2001, the entire contents of which are hereby incorporated by reference.

As described herein, a specified number range of atoms includes any integer therein. For example, a group having from 1-4 atoms could have 1, 2, 3, or 4 atoms.

As described herein, compounds of the invention may optionally be substituted with one or more substituents, such as are illustrated generally herein, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

Unless otherwise indicated, a substituent connected by a bond drawn from the center of a ring means that the substituent can be bonded to any position in the ring. In example i below, for instance, $J^w$ can be bonded to any position on the pyridyl ring. For bicyclic rings, a bond drawn through both rings indicates that the substituent can be bonded from any position of the bicyclic ring. In example ii below, for instance, $J^w$ can be bonded to the 5-membered ring (on the nitrogen atom, for instance), and to the 6-membered ring.

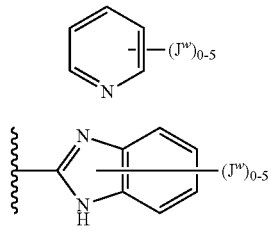

The term "stable", as used herein, refers to compounds that are not substantially altered when subjected to conditions to allow for their production, detection, recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "dative bond", as used herein, is defined as the coordination bond formed upon interaction between molecular species, one of which serves as a donor and the other as an acceptor of the electron pair to be shared in the complex formed.

The term "aliphatic" or "aliphatic group", as used herein, means a straight-chain (i.e., unbranched), branched, or cyclic, substituted or unsubstituted hydrocarbon chain that is completely saturated or that contains one or more units of unsaturation that has a single point of attachment to the rest of the molecule.

Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. Aliphatic groups may be linear or branched, substituted or unsubstituted alkyl, alkenyl, or alkynyl groups. Specific examples include, but are not limited to, methyl, ethyl, isopropyl, n-propyl, sec-butyl, vinyl, n-butenyl, ethynyl, and tert-butyl. Aliphatic groups may also be cyclic, or have a combination of linear or branched and cyclic groups. Examples of such types of aliphatic groups include, but are not limited to cyclopropyl, cyclobutyl, cyclopentyl, cyclohexyl, cyclohexenyl, —CH$_2$-cyclopropyl, CH$_2$CH$_2$CH(CH$_3$)-cyclohexyl.

The term "cycloaliphatic" (or "carbocycle" or "carbocyclyl") refers to a monocyclic $C_3$-$C_8$ hydrocarbon or bicyclic $C_8$-$C_{12}$ hydrocarbon that is completely saturated or that contains one or more units of unsaturation, but which is not aromatic, that has a single point of attachment to the rest of the molecule wherein any individual ring in said bicyclic ring system has 3-7 members. Examples of cycloaliphatic groups include, but are not limited to, cycloalkyl and cycloalkenyl groups. Specific examples include, but are not limited to, cyclohexyl, cyclopropyl, and cyclobutyl.

The term "heterocycle", "heterocyclyl", or "heterocyclic" as used herein means non-aromatic, monocyclic, bicyclic, or tricyclic ring systems in which one or more ring members are an independently selected heteroatom. In some embodiments, the "heterocycle", "heterocyclyl", or "heterocyclic" group has three to fourteen ring members in which one or more ring members is a heteroatom independently selected from oxygen, sulfur, nitrogen, or phosphorus, and each ring in the system contains 3 to 7 ring members.

Examples of heterocycles include, but are not limited to, 3-1H-benzimidazol-2-one, 3-(1-alkyl)-benzimidazol-2-one, 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl, indolinyl, tetrahydroquinolinyl, tetrahydroisoquinolinyl, benzothiolane, benzodithiane, and 1,3-dihydro-imidazol-2-one.

Cyclic groups, (e.g. cycloaliphatic and heterocycles), can be linearly fused, bridged, or spirocyclic.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated", as used herein, means that a moiety has one or more units of unsaturation. As would be known by one of skill in the art, unsaturated groups can be partially unsaturated or fully unsaturated. Examples of partially unsaturated groups include, but are not limited to, butene, cyclohexene, and tetrahydropyridine. Fully unsaturated groups can be aromatic, anti-aromatic, or non-aromatic. Examples of fully unsaturated groups include, but are not limited to, phenyl, cyclooctatetraene, pyridyl, thienyl, and 1-methylpyridin-2(1H)-one.

The term "alkoxy", or "thioalkyl", as used herein, refers to an alkyl group, as previously defined, attached through an oxygen ("alkoxy") or sulfur ("thioalkyl") atom.

The terms "haloalkyl", "haloalkenyl", "haloaliphatic", and "haloalkoxy" mean alkyl, alkenyl or alkoxy, as the case may be, substituted with one or more halogen atoms. This term includes perfluorinated alkyl groups, such as —CF$_3$ and —CF$_2$CF$_3$.

The terms "halogen", "halo", and "hal" mean F, Cl, Br, or I.

The term "aryl" used alone or as part of a larger moiety as in "arylalkyl", "arylalkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring".

The term "heteroaryl", used alone or as part of a larger moiety as in "heteroarylalkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic". Examples of heteroaryl rings include, but are not limited to, 2-furanyl, 3-furanyl, N-imidazolyl, 2-imidazolyl, 4-imidazolyl, 5-imidazolyl, benzimidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, benzofuryl, benzothiophenyl, indolyl (e.g., 2-indolyl), pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, purinyl, pyrazinyl, 1,3,5-triazinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

It shall be understood that the term "heteroaryl" includes certain types of heteroaryl rings that exist in equilibrium between two different forms. More specifically, for example, species such hydropyridine and pyridinone (and likewise hydroxypyrimidine and pyrimidinone) are meant to be encompassed within the definition of "heteroaryl."

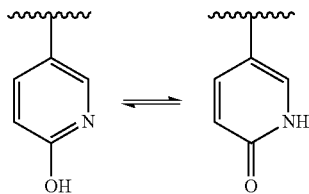 [SMILES: *c1ccc(O)nc1 ; *c1ccc(=O)[nH]c1]

The term "protecting group" and "protective group" as used herein, are interchangeable and refer to an agent used to temporarily block one or more desired functional groups in a compound with multiple reactive sites. In certain embodiments, a protecting group has one or more, or preferably all, of the following characteristics: a) is added selectively to a functional group in good yield to give a protected substrate that is b) stable to reactions occurring at one or more of the other reactive sites; and c) is selectively removable in good yield by reagents that do not attack the regenerated, deprotected functional group. As would be understood by one skilled in the art, in some cases, the reagents do not attack other reactive groups in the compound. In other cases, the reagents may also react with other reactive groups in the compound. Examples of protecting groups are detailed in Greene, T. W., Wuts, P. G in "Protective Groups in Organic Synthesis", Third Edition, John Wiley & Sons, New York: 1999 (and other editions of the book), the entire contents of which are hereby incorporated by reference. The term "nitrogen protecting group", as used herein, refers to an agent used to temporarily block one or more desired nitrogen reactive sites in a multifunctional compound. Preferred nitrogen protecting groups also possess the characteristics exemplified for a protecting group above, and certain exemplary nitrogen protecting groups are also detailed in Chapter 7 in Greene, T. W., Wuts, P. G in "Protective Groups in Organic Synthesis", Third Edition, John Wiley & Sons, New York: 1999, the entire contents of which are hereby incorporated by reference.

In some embodiments, a methylene unit of an alkyl or aliphatic chain is optionally replaced with another atom or group. Examples of such atoms or groups include, but are not limited to, nitrogen, oxygen, sulfur, —C(O)—, —C(=N—CN)—, —C(=NR)-, —C(=NOR)-, —SO—, and —SO$_2$—. These atoms or groups can be combined to form larger groups. Examples of such larger groups include, but are not limited to, —OC(O)—, —C(O)CO—, —CO$_2$—, —C(O)NR—, —C(=N—CN), —NRCO—, —NRC(O) O—, —SO$_2$NR—, —NRSO$_2$—, —NRC(O)NR-, —OC(O) NR-, and —NRSO$_2$NR-, wherein R is, for example, H or $C_{1-6}$aliphatic. It should be understood that these groups can be bonded to the methylene units of the aliphatic chain via single, double, or triple bonds. An example of an optional replacement (nitrogen atom in this case) that is bonded to the aliphatic chain via a double bond would be —CH$_2$CH=N—CH$_3$. In some cases, especially on the terminal end, an optional replacement can be bonded to the aliphatic group via a triple bond. One example of this would be CH$_2$CH$_2$CH$_2$C≡N. It should be understood that in this situation, the terminal nitrogen is not bonded to another atom.

It should also be understood that, the term "methylene unit" can also refer to branched or substituted methylene units. For example, in an isopropyl moiety [—CH(CH$_3$)$_2$], a nitrogen atom (e.g. NR) replacing the first recited "methylene unit" would result in dimethylamine [—N(CH$_3$)$_2$]. In instances such as these, one of skill in the art would understand that the nitrogen atom will not have any additional atoms bonded to it, and the "R" from "NR" would be absent in this case.

Unless otherwise indicated, the optional replacements form a chemically stable compound. Optional replacements can occur both within the chain and/or at either end of the chain; i.e. both at the point of attachment and/or also at the terminal end. Two optional replacements can also be adjacent to each other within a chain so long as it results in a chemically stable compound. For example, a C$_3$ aliphatic can be optionally replaced by 2 nitrogen atoms to form —C—N=N. The optional replacements can also completely replace all of the carbon atoms in a chain. For example, a C$_3$ aliphatic can be optionally replaced by —NR-, —C(O)—, and —NR— to form —NRC(O)NR— (a urea).

Unless otherwise indicated, if the replacement occurs at the terminal end, the replacement atom is bound to a hydrogen atom on the terminal end. For example, if a methylene unit of —CH$_2$CH$_2$CH$_3$ were optionally replaced with —O—, the resulting compound could be —OCH$_2$CH$_3$, —CH$_2$OCH$_3$, or —CH$_2$CH$_2$OH. In another example, if a methylene unit of —CH$_2$CH$_2$CH$_3$ was optionally replaced with —NH—, the resulting compound could be —NHCH$_2$CH$_3$, —CH$_2$NHCH$_3$, or —CH$_2$CH$_2$NH$_2$. It should be understood that if the terminal atom does not contain any free valence electrons, then a hydrogen atom is not required at the terminal end (e.g., —CH$_2$CH$_2$CH=O or —CH$_2$CH$_2$C≡N).

Unless otherwise indicated, structures depicted herein are also meant to include all isomeric (e.g., enantiomeric, diastereomeric, geometric, conformational, and rotational) forms of the structure. For example, the R and S configurations for each asymmetric center, (Z) and (E) double bond isomers, and (Z) and (E) conformational isomers are included in this invention. As would be understood to one skilled in the art, a substituent can freely rotate around any rotatable bonds. For example, a substituent drawn as

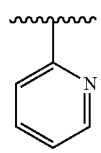

also represents

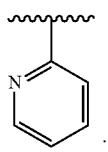

Therefore, single stereochemical isomers as well as enantiomeric, diastereomeric, geometric, conformational, and rotational mixtures of the present compounds are within the scope of the invention.

Unless otherwise indicated, all tautomeric forms of the compounds of the invention are within the scope of the invention.

Additionally, unless otherwise indicated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

The compounds described herein can exist in free form, or, where appropriate, as salts. Those salts that are pharmaceutically acceptable are of particular interest since they are useful in administering the compounds described below for medical purposes. Salts that are not pharmaceutically acceptable are useful in manufacturing processes, for isolation and purification purposes, and in some instances, for use in separating stereoisomeric forms of the compounds of the invention or intermediates thereof.

Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds described herein include those derived from suitable inorganic and organic acids and bases. These salts can be prepared in situ during the final isolation and purification of the compounds.

Where the compound described herein contains a basic group, or a sufficiently basic bioisostere, acid addition salts can be prepared by 1) reacting the purified compound in its free-base form with a suitable organic or inorganic acid and 2) isolating the salt thus formed. In practice, acid addition salts might be a more convenient form for use and use of the salt amounts to use of the free basic form.

Examples of pharmaceutically acceptable, non-toxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, glycolate, gluconate, glycolate, hemisulfate, heptanoate, hexanoate, hydrochloride, hydrobromide, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, palmoate, pectinate, persulfate, 3-phenylpropionate, phosphate, picrate, pivalate, propionate, salicylate, stearate, succinate, sulfate, tartrate, thiocyanate, p-toluenesulfonate, undecanoate, valerate salts, and the like.

Where the compound described herein contains a carboxy group or a sufficiently acidic bioisostere, base addition salts can be prepared by 1) reacting the purified compound in its acid form with a suitable organic or inorganic base and 2) isolating the salt thus formed. In practice, use of the base addition salt might be more convenient and use of the salt form inherently amounts to use of the free acid form. Salts derived from appropriate bases include alkali metal (e.g., sodium, lithium, and potassium), alkaline earth metal (e.g., magnesium and calcium), ammonium and N$^+$(C$_{1-4}$alkyl)$_4$ salts. This invention also envisions the quaternization of any basic nitrogen-containing groups of the compounds disclosed herein. Water or oil-soluble or dispersible products may be obtained by such quaternization.

Basic addition salts include pharmaceutically acceptable metal and amine salts. Suitable metal salts include the sodium, potassium, calcium, barium, zinc, magnesium, and aluminum. The sodium and potassium salts are usually preferred. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate. Suitable inorganic base addition salts are prepared from metal bases, which include sodium hydride, sodium hydroxide, potassium hydroxide, calcium hydroxide, aluminium hydroxide, lithium hydroxide, magnesium hydroxide, zinc hydroxide and the like. Suitable amine base addition salts are prepared from amines which are frequently used in medicinal chemistry because of their low toxicity and acceptability for medical use. Ammonia, ethylenediamine, N-methyl-glucamine, lysine, arginine, ornithine, choline, N, N'-dibenzylethylenediamine, chloroprocaine, dietanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, dicyclohexylamine and the like are examples of suitable base addition salts.

Other acids and bases, while not in themselves pharmaceutically acceptable, may be employed in the preparation of salts useful as intermediates in obtaining the compounds described herein and their pharmaceutically acceptable acid or base addition salts.

It should be understood that this invention includes mixtures/combinations of different pharmaceutically acceptable salts and also mixtures/combinations of compounds in free form and pharmaceutically acceptable salts.

The compounds described herein can also exist as pharmaceutically acceptable solvates (e.g., hydrates) and clathrates. As used herein, the term "pharmaceutically acceptable solvate," is a solvate formed from the association of one or more pharmaceutically acceptable solvent molecules to one of the compounds described herein. The term solvate includes hydrates (e.g., hemihydrate, monohydrate, dihydrate, trihydrate, tetrahydrate, and the like).

As used herein, the term "hydrate" means a compound described herein or a salt thereof that further includes a stoichiometric or non-stoichiometric amount of water bound by non-covalent intermolecular forces.

As used herein, the term "clathrate" means a compound described herein or a salt thereof in the form of a crystal lattice that contains spaces (e.g., channels) that have a guest molecule (e.g., a solvent or water) trapped within.

In addition to the compounds described herein, pharmaceutically acceptable derivatives including prodrugs of these compounds may also be employed in compositions to treat or prevent the herein identified disorders.

siRNA Inhibitors

Another class of inhibitors useful for treatment of PTEN mutated or deficient cancer includes nucleic acid inhibitors of one or more SWI/SNF BAF-complex genes, or the complements thereof, which inhibit activity or function by down-regulating production of active polypeptide. This can be monitored using conventional methods well known in the art, for example by screening using real time PCR as described in the examples.

Expression of mitotic kinases may be inhibited using anti-sense or RNAi technology. The use of these approaches to down-regulate gene expression is now well-established in the art.

Anti-sense oligonucleotides may be designed to hybridise to the complementary sequence of nucleic acid, pre-mRNA or mature mRNA, interfering with the production of the base excision repair pathway component so that its expression is reduced or completely or substantially completely prevented. In addition to targeting coding sequence, anti-sense techniques may be used to target control sequences of a gene, e.g. in the 5' flanking sequence, whereby the anti-sense oligonucleotides can interfere with expression control sequences. The construction of anti-sense sequences and their use is described for example in Peyman & Ulman, Chemical Reviews, 90:543-584, 1990 and Crooke, Ann. Rev. Pharmacol. Toxicol., 32:329-376, 1992.

Oligonucleotides may be generated in vitro or ex vivo for administration or anti-sense RNA may be generated in vivo within cells in which down-regulation is desired. Thus, double-stranded DNA may be placed under the control of a promoter in a "reverse orientation" such that transcription of the anti-sense strand of the DNA yields RNA which is complementary to normal mRNA transcribed from the sense strand of the target gene. The complementary anti-sense RNA sequence is thought then to bind with mRNA to form a duplex, inhibiting translation of the endogenous mRNA from the target gene into protein. Whether or not this is the actual mode of action is still uncertain. However, it is established fact that the technique works.

The complete sequence corresponding to the coding sequence in reverse orientation need not be used. For example fragments of sufficient length may be used. It is a routine matter for the person skilled in the art to screen fragments of various sizes and from various parts of the coding or flanking sequences of a gene to optimise the level of anti-sense inhibition. It may be advantageous to include the initiating methionine ATG codon, and perhaps one or more nucleotides upstream of the initiating codon. A suitable fragment may have about 14-23 nucleotides, e.g., about 15, 16 or 17 nucleotides.

An alternative to anti-sense is to use a copy of all or part of the target gene inserted in sense, that is the same orientation as the target gene, to achieve reduction in expression of the target gene by co-suppression (Angell & Baulcombe, The EMBO Journal 16(12):3675-3684, 1997 and Voinnet & Baulcombe, Nature, 389: 553, 1997). Double stranded RNA (dsRNA) has been found to be even more effective in gene silencing than both sense or antisense strands alone (Fire et al, Nature 391, 806-811, 1998). dsRNA mediated silencing is gene specific and is often termed RNA interference (RNAi). Methods relating to the use of RNAi to silence genes in C. elegans, Drosophila, plants, and mammals are known in the art (Fire, Trends Genet., 15: 358-363, 19999; Sharp, RNA interference, Genes Dev. 15: 485-490 2001; Hammond et al., Nature Rev. Genet. 2: 110-1119, 2001; Tuschl, Chem. Biochem. 2: 239-245, 2001; Hamilton et al., Science 286: 950-952, 1999; Hammond, et al., Nature 404: 293-296, 2000; Zamore et al., Cell, 101: 25-33, 2000; Bernstein, Nature, 409: 363-366, 2001; Elbashir et al, Genes Dev., 15: 188-200, 2001; WO01/29058; WO99/32619, and Elbashir et al, Nature, 411: 494-498, 2001).

RNA interference is a two-step process. First, dsRNA is cleaved within the cell to yield short interfering RNAs (siRNAs) of about 21-23nt length with 5' terminal phosphate and 3' short overhangs (~2nt). The siRNAs target the corresponding mRNA sequence specifically for destruction (Zamore, Nature Structural Biology, 8, 9, 746-750, 2001.

RNAi may also be efficiently induced using chemically synthesized siRNA duplexes of the same structure with 3'-overhang ends (Zamore et al, Cell, 101: 25-33, 2000). Synthetic siRNA duplexes have been shown to specifically suppress expression of endogenous and heterologous genes in a wide range of mammalian cell lines (Elbashir et al, Nature, 411: 494-498, 2001).

Another possibility is that nucleic acid is used which on transcription produces a ribozyme, able to cut nucleic acid at a specific site and therefore also useful in influencing gene expression, e.g., see Kashani-Sabet & Scanlon, Cancer Gene Therapy, 2(3): 213-223, 1995 and Mercola & Cohen, Cancer Gene Therapy, 2(1): 47-59, 1995.

Small RNA molecules may be employed to regulate gene expression. These include targeted degradation of mRNAs by small interfering RNAs (siRNAs), post transcriptional gene silencing (PTGs), developmentally regulated sequence-specific translational repression of mRNA by micro-RNAs (miRNAs), and targeted transcriptional gene silencing.

A role for the RNAi machinery and small RNAs in targeting of heterochromatin complexes and epigenetic gene silencing at specific chromosomal loci has also been demonstrated. Double-stranded RNA (dsRNA)-dependent post transcriptional silencing, also known as RNA interference (RNAi), is a phenomenon in which dsRNA complexes can target specific genes of homology for silencing in a short period of time. It acts as a signal to promote degradation of mRNA with sequence identity. A 20-nt siRNA is generally long enough to induce gene-specific silencing, but short enough to evade host response. The decrease in expression of targeted gene products can be extensive with 90% silencing induced by a few molecules of siRNA.

In the art, these RNA sequences are termed "short or small interfering RNAs" (siRNAs) or "microRNAs" (miRNAs) depending on their origin. Both types of sequence may be used to down-regulate gene expression by binding to complimentary RNAs and either triggering mRNA elimination (RNAi) or arresting mRNA translation into protein. siRNA are derived by processing of long double stranded RNAs and when found in nature are typically of exogenous origin. Micro-interfering RNAs (miRNA) are endogenously encoded small non-coding RNAs, derived by processing of short hairpins. Both siRNA and miRNA can inhibit the translation of mRNAs bearing partially complimentary target sequences without RNA cleavage and degrade mRNAs bearing fully complementary sequences.

The siRNA ligands are typically double stranded and, in order to optimise the effectiveness of RNA mediated down-regulation of the function of a target gene, it is preferred that the length of the siRNA molecule is chosen to ensure correct recognition of the siRNA by the RISC complex that mediates the recognition by the siRNA of the mRNA target and so that the siRNA is short enough to reduce a host response.

miRNA ligands are typically single stranded and have regions that are partially complementary enabling the ligands to form a hairpin. miRNAs are RNA genes which are transcribed from DNA, but are not translated into protein. A DNA sequence that codes for a miRNA gene is longer than the miRNA. This DNA sequence includes the miRNA sequence and an approximate reverse complement. When this DNA sequence is transcribed into a single-stranded RNA molecule, the miRNA sequence and its reverse-complement base pair to form a partially double stranded RNA segment. The design of microRNA sequences is discussed in John et al, PLoS Biology, 11(2), 1862-1879, 2004.

Typically, the RNA ligands intended to mimic the effects of siRNA or miRNA have between 10 and 40 ribonucleotides (or synthetic analogues thereof), more preferably between 17 and 30 ribonucleotides, more preferably between 19 and 25 ribonucleotides and most preferably between 21 and 23 ribonucleotides. In some embodiments of the invention employing double-stranded siRNA, the molecule may have symmetric 3' overhangs, e.g. of one or two (ribo)nucleotides, typically a UU of dTdT 3' overhang. Based on the disclosure provided herein, the skilled person can readily design suitable siRNA and miRNA sequences, for example using resources such as Ambion's siRNA finder, see http://www.ambion.com/techlib/misc/siRNA_finder.html. siRNA and miRNA sequences can be synthetically produced and added exogenously to cause gene downregulation or produced using expression systems (e.g. vectors). In a preferred embodiment the siRNA is synthesized synthetically.

Longer double stranded RNAs may be processed in the cell to produce siRNAs (e.g. see Myers, Nature Biotechnology, 21: 324-328, 2003). The longer dsRNA molecule may have symmetric 3' or 5' overhangs, e.g. of one or two (ribo)nucleotides, or may have blunt ends. The longer dsRNA molecules may be 25 nucleotides or longer. Preferably, the longer dsRNA molecules are between 25 and 30 nucleotides long. More preferably, the longer dsRNA molecules are between 25 and 27 nucleotides long. Most preferably, the longer dsRNA molecules are 27 nucleotides in length. dsRNAs 30 nucleotides or more in length may be expressed using the vector pDECAP (Shinagawa et al., Genes and Dev., 17: 1340-5, 2003).

Another alternative is the expression of a short hairpin RNA molecule (shRNA) in the cell. shRNAs are more stable than synthetic siRNAs. A shRNA consists of short inverted repeats separated by a small loop sequence. One inverted repeat is complimentary to the gene target. In the cell the shRNA is processed by DICER into a siRNA which degrades the target gene mRNA and suppresses expression. In a preferred embodiment the shRNA is produced endogenously (within a cell) by transcription from a vector. shRNAs may be produced within a cell by transfecting the cell with a vector encoding the shRNA sequence under control of a RNA polymerase III promoter such as the human H1 or 7SK promoter or a RNA polymerase II promoter. Alternatively, the shRNA may be synthesised exogenously (in vitro) by transcription from a vector. The shRNA may then be introduced directly into the cell. Preferably, the shRNA sequence is between 40 and 100 bases in length, more preferably between 40 and 70 bases in length. The stem of the hairpin is preferably between 19 and 30 base pairs in length. The stem may contain G-U pairings to stabilise the hairpin structure.

In one embodiment, the siRNA, longer dsRNA or miRNA is produced endogenously (within a cell) by transcription from a vector. The vector may be introduced into the cell in any of the ways known in the art. Optionally, expression of the RNA sequence can be regulated using a tissue specific promoter. In a further embodiment, the siRNA, longer dsRNA or miRNA is produced exogenously (in vitro) by transcription from a vector.

Alternatively, siRNA molecules may be synthesized using standard solid or solution phase synthesis techniques, which are known in the art. Linkages between nucleotides may be phosphodiester bonds or alternatives, e.g., linking groups of the formula P(O)S, (thioate); P(S)S, (dithioate); P(O)NR'2; P(O)R'; P(O)OR6; CO; or CONR'2 wherein R is H (or a salt) or alkyl (1-12C) and R6 is alkyl (1-9C) is joined to adjacent nucleotides through —O— or —S—.

Modified nucleotide bases can be used in addition to the naturally occurring bases, and may confer advantageous properties on siRNA molecules containing them.

For example, modified bases may increase the stability of the siRNA molecule, thereby reducing the amount required for silencing. The provision of modified bases may also provide siRNA molecules, which are more, or less, stable than unmodified siRNA.

The term 'modified nucleotide base' encompasses nucleotides with a covalently modified base and/or sugar. For example, modified nucleotides include nucleotides having sugars, which are covalently attached to low molecular weight organic groups other than a hydroxyl group at the 3'position and other than a phosphate group at the 5'position. Thus modified nucleotides may also include 2'substituted sugars such as 2'-O-methyl-; 2-O-alkyl; 2-O-allyl; 2'-S-alkyl; 2'-S-allyl; 2'-fluoro-; 2'-halo or 2; azido-ribose, carbocyclic sugar analogues a-anomeric sugars; epimeric sugars such as arabinose, xyloses or lyxoses, pyranose sugars, furanose sugars and sedoheptulose.

Modified nucleotides are known in the art and include alkylated purines and pyrimidines, acylated purines and pyrimidines, and other heterocycles. These classes of pyrimidines and purines are known in the art and include pseudoisocytosine, N4,N4-ethanocytosine, 8-hydroxy-N6-methyladenine, 4-acetylcytosine, 5-(carboxyhydroxylmethyl) uracil, 5 fluorouracil, 5-bromouracil, 5-carboxymethylaminomethyl-2-thiouracil, 5-carboxymethylaminomethyl uracil, dihydrouracil, inosine, N6-isopentyl-adenine, 1-methyladenine, 1-methylpseudouracil, 1-methylguanine, 2,2-dimethylguanine, 2methyladenine, 2-methylguanine, 3-methylcytosine, 5-methylcytosine, N6-methyladenine, 7-methylguanine, 5-methylaminomethyl uracil, 5-methoxy amino methyl-2-thiouracil, -D-mannosylqueosine, 5-methoxycarbonylmethyluracil, 5methoxyuracil, 2 methyl-thio-N6-isopentenyladenine, uracil-5-oxyacetic acid methyl ester, psueouracil, 2-thiocytosine, 5-methyl-2 thiouracil, 2-thiouracil, 4-thiouracil, 5methyluracil, N-uracil-5-oxy-acetic acid methylester, uracil 5-oxyacetic acid, queosine, 2-thiocytosine, 5-propyluracil, 5-propylcytosine, 5-ethyluracil, 5ethylcytosine, 5-butyluracil, 5-pentyluracil, 5-pentylcytosine, and 2,6,diaminopurine, methylpsuedouracil, 1-methylguanine, 1-methylcytosine.

Antibodies

Antibodies may be employed in the present invention as an example of a class of inhibitor useful for treating BAF-complex gene mutated or deficient cancer, and more particularly as inhibitors of ATR. They may also be used in the methods disclosed herein for assessing an individual having cancer or predicting the response of an individual having cancer, in particular for determining whether the individual has BAF-complex gene mutated or deficient cancer that might be treatable according to the present invention.

As used herein, the term "antibody" includes an immunoglobulin whether natural or partly or wholly synthetically produced. The term also covers any polypeptide or protein comprising an antibody binding domain. Antibody fragments which comprise an antigen binding domain are such as Fab, scFv, Fv, dAb, Fd; and diabodies. It is possible to take monoclonal and other antibodies and use techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EP 0 184 187 A, GB 2,188,638 A or EP 0 239 400 A.

Antibodies can be modified in a number of ways and the term "antibody molecule" should be construed as covering any specific binding member or substance having an antibody antigen-binding domain with the required specificity. Thus, this term covers antibody fragments and derivatives, including any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in EP 0 120 694 A and EP 0 125 023 A.

It has been shown that fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward, E. S. et al., Nature 341, 544-546 (1989)) which consists of a VH domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al, Science, 242; 423-426, 1988; Huston et al, PNAS USA, 85: 5879-5883, 1988); (viii) bispecific single chain Fv dimers (WO 93/11161) and (ix) "diabodies", multivalent or multispecific fragments constructed by gene fusion (WO 94/13804; Holliger et al, P.N.A.S. USA, 90: 6444-6448, 1993); (x) immunoadhesins (WO 98/50431). Fv, scFv or diabody molecules may be stabilised by the incorporation of disulphide bridges linking the VH and VL domains (Reiter et al, Nature Biotech, 14: 1239-1245, 1996). Minibodies comprising a scFv joined to a CH3 domain may also be made (Hu et al, Cancer Res., 56: 3055-3061, 1996).

Preferred antibodies used in accordance with the present invention are isolated, in the sense of being free from contaminants such as antibodies able to bind other polypeptides and/or free of serum components. Monoclonal antibodies are preferred for some purposes, though polyclonal antibodies are within the scope of the present invention.

The reactivities of antibodies on a sample may be determined by any appropriate means. Tagging with individual reporter molecules is one possibility. The reporter molecules may directly or indirectly generate detectable, and preferably measurable, signals. The linkage of reporter molecules may be directly or indirectly, covalently, e.g. via a peptide bond or non-covalently. Linkage via a peptide bond may be as a result of recombinant expression of a gene fusion encoding antibody and reporter molecule. One favoured mode is by covalent linkage of each antibody with an individual fluorochrome, phosphor or laser exciting dye with spectrally isolated absorption or emission characteristics. Suitable fluorochromes include fluorescein, rhodamine, phycoerythrin and Texas Red. Suitable chromogenic dyes include diaminobenzidine.

Other reporters include macromolecular colloidal particles or particulate material such as latex beads that are coloured, magnetic or paramagnetic, and biologically or chemically active agents that can directly or indirectly cause detectable signals to be visually observed, electronically detected or otherwise recorded. These molecules may be enzymes which catalyse reactions that develop or change colours or cause changes in electrical properties, for example. They may be molecularly excitable, such that electronic transitions between energy states result in characteristic spectral absorptions or emissions. They may include chemical entities used in conjunction with biosensors. Biotin/avidin or biotin/streptavidin and alkaline phosphatase detection systems may be employed.

Antibodies according to the present invention may be used in screening for the presence of a polypeptide, for example in a test sample containing cells or cell lysate as discussed, and may be used in purifying and/or isolating a polypeptide according to the present invention, for instance following production of the polypeptide by expression from encoding nucleic acid. Antibodies may modulate the activity of the polypeptide to which they bind and so, if that polypeptide has a deleterious effect in an individual, may be useful in a therapeutic context (which may include prophylaxis).

BAF Complex Genes

BAF complex genes are an established group of proteins that constitute the multi-subunit SWI/SNF chromatin-remodelling complexes "BRG1- or HRBM-associated factors" (BAF) and polybromo-associated BAF (PBAF). They mediate ATP-dependent chromatin remodelling processes that are critical for differentiation and proliferation.

Several components of the complexes function as tumour suppressors (see Reisman, Oncogene 28: 1653-1668, 2009). BAF complex genes include, but are not limited to, ARID1A, ARID1B, ARID2, SMARCA2, SMARCA4, SMARCB1, SMARCC2, SMARCC1, SMARCD1, 2 and 3, SMARCE1, ACTL6A, ACTL6B and PBRM1. A preferred example of a BAF-complex gene, a cancer deficient in which can be treated in accordance with the present invention, is ARID1A (AT-rich DNA-interacting domain 1A), also known as OSA, p270 and BAF250A. ARID1A is located 1p36.11 (16)—a region frequently deleted in human cancers (17)—and may be deficient in as many as 30% of renal carcinomas and 10% of breast carcinomas (18).

Treatment of Cancer

The present invention provides methods and medical uses for the treatment of BAF-complex gene deficient or mutated cancers with ATR inhibitors. A BAF-complex gene deficient or mutated cancer may be identified as such by testing a sample of cancer cells from an individual, for example to determine whether one or more BAF-complex gene protein contains one or more mutations. It is known that BAF-complex gene mutations are present with high frequency across many different tumour types. The cancers with the highest BAF-complex mutation rates are synovial sarcoma, ovarian clear cell carcinoma (75%), colorectal cancer (55%), melanoma (39%), lung cancer (35%), hepatocellular carcinoma (33%), gastric cancer (32%), bladder cancer (22%), hematologic malignancies (15%), squamous cell carcinoma (14%), serous ovarian cancer (12%), breast cancer (11%), pancreatic cancer (10%), medulloblastoma (8%), renal cancer (6%) and glioma (6%). Across all tumour types, the average frequency of BAF-complex gene mutations is 19.6% (13). (Shain & Pollack, PLoS One. 2013; 8(1): e55119.).

Cancers with defects in the SWI/SNF BAF as defined in Kadoch, C., et al. (Proteomic and bioinformatic analysis of mammalian SWI/SNF complexes identifies extensive roles in human malignancy. Nat Genet 45, 592-601 (2013)) include colorectal cancers, ovarian clear cell cancer. serous ovarian cancer, pancreatic cancer, gastric cancer, bladder cancer, hepatocellular cancer, renal cancer, squamous cell carcinoma, breast cancer, medulloblastoma, glioma, melanoma, lung cancer, hematologic malignancies and synovial sarcoma.

In some embodiments, the BAF-deficient cancer is characterised by one or more BAF-complex gene mutation(s) or defects(s) occurring in somatic pre-cancerous or cancerous cells. In yet another embodiment, the BAF-deficient cancer is characterised by one or more BAF-complex gene mutation(s) occurring in the germ line of the individual patient.

In some embodiments, a BAF-complex gene deficient or mutated cancer may be identified as such by testing a sample of cancer cells from an individual to determine the expression of one or more BAF-complex genes to evaluate whether expression of the protein is absent or at a reduced level compared to normal.

In other embodiments, the BAF-deficient cancer is characterised by the cancer cells having a defect in or the cancer cells exhibiting epigenetic inactivation of a BAF complex gene, or loss of protein function.

More generally, a cancer may be identified as a BAF-deficient cancer by determining the activity of the BAF polypeptides in a sample of cells from an individual. The sample may be of normal cells from the individual where the individual has a mutation in one or more BAF genes or the sample may be of cancer cells, e.g. where the cells forming a tumour exhibit defects in BAF activity. Activity may be determined relative to a control, for example in the case of defects in cancer cells, a relative to non-cancerous cells, preferably from the same tissue. The activity of one or more BAF genes may be determined by using techniques well known in the art such as Western blot analysis, immunohistology, chromosomal abnormalities, enzymatic or DNA binding assays, and plasmid-based assays.

The sample may be of normal cells from the individual where the individual has a mutation in one or more BAF-complex gene or the sample may be of cancer cells, e.g. where the cells forming a tumour contain one or more BAF-complex gene mutations. Activity may be determined relative to a control, for example in the case of defects in cancer cells, relative to non-cancerous cells, preferably from the same tissue.

The determination of BAF-complex gene expression may involve determining the presence or amount of BAF-complex gene mRNA in a sample. Methods for doing this are well known to the skilled person. By way of example, they include determining the presence of BAF-complex gene mRNA (i) using a labelled probe that is capable of hybridising to the BAF-complex gene nucleic acid; and/or (ii) using PCR involving one or more primers based on a BAF-complex gene nucleic acid sequence to determine whether the BAF-complex gene transcript is present in a sample. The probe may also be immobilised as a sequence included in a microarray.

In one embodiment, detecting BAF-complex gene mRNA is carried out by extracting RNA from a sample of the tumour and measuring expression of one or more BAF-complex gene specifically using quantitative real time RT-PCR. Alternatively or additionally, the expression of BAF-complex gene could be assessed using RNA extracted from a tumour sample using microarray analysis, which measures the levels of mRNA for a group of genes using a plurality of probes immobilised on a substrate to form the array.

In some embodiments, a cancer may be identified as BAF-deficient by determining the presence in a cell sample from an individual's tumour of one or more chromosomal abnormalities, for example deletions in part or loss of entire chromosomes, corresponding to gene loss. Chromosomal abnormalities may be visualised through any karyotyping technique known in the art, including but not limited to Giemesa staining, quinacrine staining, Hoechst 33258 staining, DAPI (4'-6-diamidino-2-phenylindole) staining, daunomycin staining, and fluorescence in situ hybridization. In a further embodiment, the BAF-complex gene is ARID1A and the deficiency is determined by a chromosomal abnormality comprising of the loss of at least the section 1p36.11 from chromosome 1.

In some embodiments, a cancer may be identified as a BAF-deficient cancer by determining the presence in a cell sample from the individual of one or more variations, for example, polymorphisms or mutations, in a nucleic acid encoding a BAF complex polypeptide.

Sequence variations such as mutations and polymorphisms may include a deletion, insertion or substitution of one or more nucleotides, relative to the wild-type nucleotide sequence. The one or more variations may be in a coding or non-coding region of the nucleic acid sequence and may reduce or abolish the expression or function of the BAF gene. In other words, the variant nucleic acid may encode a variant polypeptide which has reduced or abolished activity or may encode a wild-type polypeptide which has little or no expression within the cell, for example through the altered activity of a regulatory element. A variant nucleic acid may have one or more mutations or polymorphisms relative to the wild-type sequence.

Alternatively or additionally, in the present invention the determination of whether a patient has a BAF deficient cancer can be carried out by analysis of BAF complex protein expression, for example by examining whether levels of one or more BAF complex protein are supressed.

In some aspects, the presence or amount of BAF complex protein may be determined using a binding agent capable of specifically binding to the BAF complex protein, or fragments thereof. A preferred type of BAF complex protein binding agent is an antibody capable of specifically binding the BAF complex protein or fragment thereof. The antibody may be labelled to enable it to be detected or capable of detection following reaction with one or more further species, for example using a secondary antibody that is labelled or capable of producing a detectable result, e.g. in an ELISA type assay. As an alternative, a labelled binding agent may be employed in a western blot to detect BAF complex protein.

Alternatively, or additionally, the method for determining the presence of a BAF complex protein may be carried out on tumour samples, for example using immunohistochemical (IHC) analysis. IHC analysis can be carried out using paraffin fixed samples or frozen tissue samples, and generally involves staining the samples to highlight the presence and location of the BAF complex protein.

In some embodiments of the present invention, the BAF-deficient cancer is characterised by one or more mutations in the gene or protein sequence, a deficiency, and/or an absence in a BAF-complex gene selected from one or more of ARID1A, ARID1B, ARID2, SMARCA2, SMARCA4, SMARCB1, SMARCC2, SMARCC1, SMARCD1, SMARCD2, SMARCD3, SMARCE1, ACTL6A, ACTL6B and/or PBRM1. More preferably, the mutated or deficient BAF-complex gene is selected from one or more of ARID1A, ARID1B, ARID2, SMARCA2, SMARCA4 and SMARCB1, and more preferably, the mutated or deficient BAF-complex gene is ARID1A.

In some embodiments, the BAF-deficient cancer is characterised by one or more mutations, a deficiency, and/or or an absence in ARID1A.

In a further aspect, the present invention provides an assay comprising:
  measuring or quantifying a mutation or deficiency in one or more BAF-complex genes selected from one or more of ARID1A, ARID1B, ARID2, SMARCA2, SMARCA4, SMARCB1, SMARCC2, SMARCC1, SMARCD1, SMARCD2, SMARCD3, SMARCE1, ACTL6A, ACTL6B and/or PBRM1 in a biological sample obtained from an individual with cancer; and
    comparing the measured or quantified amount of the one or more BAF-complex genes with a reference value, and if the one or more BAF-complex genes is mutated or deficient relative to the reference value, identifying the individual as having an increased probability of being responsive to treatment with an Ataxia-Telangiectasia Mutated and Rad3-related protein kinase (ATR) inhibitor.

In a further aspect, the present invention provides an assay comprising:
  measuring or quantifying a mutation or deficiency in one or more genes selected from one or more of SSX1, SSX2 and/or SS18 in a biological sample obtained from an individual with synovial sarcoma; and
  comparing the measured or quantified amount of the one or more genes selected from one or more of SSX1, SSX2 and/or SS18 with a reference value, and if the one or more BAF-complex genes is mutated or deficient relative to the reference value, identifying the individual as having an increased probability of being responsive to treatment with an Ataxia-Telangiectasia Mutated and Rad3-related protein kinase (ATR) inhibitor.

Methods of Screening for ATR Inhibitors

The present invention also includes methods of screening that employ ATR as a protein target for the screening of candidate compounds to find ATR inhibitors. Accordingly, methods of screening may be carried out for identifying candidate agents that are capable of inhibiting ATR, for subsequent use of development as agents for the treatment of BAF-complex gene mutated or deficient cancer or for the treatment of synovial sarcoma. Conveniently, this may be done in an assay buffer to help the components of the assay interact, and in a multiple well format to test a plurality of candidate agents. The activity of ATR can then be determined in the presence and absence of the one or more candidate compounds to determine whether a given candidate is an inhibitor of ATR.

By way of example, the candidate agent may be a known inhibitor of one of the protein targets disclosed herein, an antibody, a peptide, a nucleic acid molecule or an organic or inorganic compound, e.g. molecular weight of less than 100 Da. In some instances, the use of candidate agents that are compounds is preferred. However, for any type of candidate agent, combinatorial library technology provides an efficient way of testing a potentially vast number of different substances for ability to modulate activity of a target protein. Such libraries and their use are known in the art. The present invention also specifically envisages screening candidate agents known for the treatment of other conditions, and especially other forms of cancer. This has the advantage that the patient or disease profile of known therapeutic agents might be expanded or modified using the screening techniques disclosed herein, or for therapeutic agents in development, patient or disease profiles established that are relevant for the treatment of BAF-complex gene mutated or deficient cancer.

Following identification of a candidate agent for further investigation, the agent in question may be tested to determine whether it is not lethal to normal cells or otherwise is suited to therapeutic use. Following these studies, the agent may be manufactured and/or used in the preparation of a medicament, pharmaceutical composition or dosage form.

The development of lead agents or compounds from an initial hit in screening assays might be desirable where the agent in question is difficult or expensive to synthesise or where it is unsuitable for a particular method of administration, e.g. peptides are unsuitable active agents for oral compositions as they tend to be quickly degraded by proteases in the alimentary canal. Mimetic design, synthesis and testing is generally used to avoid randomly screening large number of molecules for a target property.

There are several steps commonly taken in the design of a mimetic from a compound having a given target property. Firstly, the particular parts of the compound that are critical and/or important in determining the target property are determined. In the case of a peptide, this can be done by systematically varying the amino acid residues in the peptide, e.g. by substituting each residue in turn. These parts or residues constituting the active region of the compound are known as its "pharmacophore".

Once the pharmacophore has been found, its structure is modelled to according its physical properties, e.g. stereochemistry, bonding, size and/or charge, using data from a range of sources, e.g. spectroscopic techniques, X-ray diffraction data and NMR. Computational analysis, similarity mapping (which models the charge and/or volume of a pharmacophore, rather than the bonding between atoms) and other techniques can be used in this modelling process. In a variant of this approach, the three-dimensional structure of the ligand and its binding partner are modelled. This can be especially useful where the ligand and/or binding partner change conformation on binding, allowing the model to take account of this in the design of the mimetic.

A template molecule is then selected onto which chemical groups which mimic the pharmacophore can be grafted. The template molecule and the chemical groups grafted on to it can conveniently be selected so that the mimetic is easy to synthesise, is likely to be pharmacologically acceptable, and does not degrade in vivo, while retaining the biological activity of the lead compound. The mimetics found by this approach can then be screened to see whether they have the target property, or to what extent they exhibit it. Further optimisation or modification can then be carried out to arrive at one or more final mimetics for in vivo or clinical testing.

Pharmaceutical Compositions

The active agents herein for the treatment of BAF-deficient cancer may be administered alone, but it is generally preferable to provide them in pharmaceutical compositions that additionally comprise with one or more pharmaceutically acceptable carriers, adjuvants, excipients, diluents, fillers, buffers, stabilisers, preservatives, lubricants, or other materials well known to those skilled in the art and optionally other therapeutic or prophylactic agents. Examples of components of pharmaceutical compositions are provided in Remington's Pharmaceutical Sciences, 20th Edition, 2000, pub. Lippincott, Williams & Wilkins.

These compounds or derivatives of them may be used in the present invention for the treatment of BAF-deficient cancer. As used herein "derivatives" of the therapeutic agents includes salts, coordination complexes, esters such as in vivo hydrolysable esters, free acids or bases, hydrates, prodrugs or lipids, coupling partners.

Salts of the compounds of the invention are preferably physiologically well tolerated and non toxic. Many examples of salts are known to those skilled in the art. Compounds having acidic groups, such as phosphates or sulfates, can form salts with alkaline or alkaline earth metals such as Na, K, Mg and Ca, and with organic amines such as triethylamine and Tris (2-hydroxyethyl)amine. Salts can be formed between compounds with basic groups, e.g., amines, with inorganic acids such as hydrochloric acid, phosphoric acid or sulfuric acid, or organic acids such as acetic acid, citric acid, benzoic acid, fumaric acid, or tartaric acid. Compounds having both acidic and basic groups can form internal salts.

Esters can be formed between hydroxyl or carboxylic acid groups present in the compound and an appropriate carboxylic acid or alcohol reaction partner, using techniques well known in the art.

Derivatives include prodrugs of the compounds which are convertible in vivo or in vitro into one of the parent compounds. Typically, at least one of the biological activities of compound will be reduced in the prodrug form of the compound, and can be activated by conversion of the prodrug to release the compound or a metabolite of it.

Other derivatives include coupling partners of the compounds in which the compounds is linked to a coupling partner, e.g. by being chemically coupled to the compound or physically associated with it. Examples of coupling partners include a label or reporter molecule, a supporting substrate, a carrier or transport molecule, an effector, a drug, an antibody or an inhibitor. Coupling partners can be covalently linked to compounds of the invention via an appropriate functional group on the compound such as a hydroxyl group, a carboxyl group or an amino group. Other derivatives include formulating the compounds with liposomes.

The term "pharmaceutically acceptable" as used herein includes compounds, materials, compositions, and/or dosage forms which are, within the scope of sound medical judgement, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

The active agents disclosed herein for the treatment of BAF-deficient cancer according to the present invention are preferably for administration to an individual in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc., is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 20th Edition, 2000, Lippincott, Williams & Wilkins. A composition may be administered alone or in combination with other treatments, either simultaneously or sequentially, dependent upon the condition to be treated.

The formulations may conveniently be presented in unit dosage form and may be prepared by any methods well known in the art of pharmacy. Such methods include the step of bringing the active compound into association with a carrier which may constitute one or more accessory ingredients. In general, the formulations are prepared by uniformly and intimately bringing into association the active compound with liquid carriers or finely divided solid carriers or both, and then if necessary shaping the product.

The agents disclosed herein for the treatment of BAF-deficient cancer may be administered to a subject by any convenient route of administration, whether systemically/peripherally or at the site of desired action, including but not limited to, oral (e.g. by ingestion); topical (including e.g. transdermal, intranasal, ocular, buccal, and sublingual); pulmonary (e.g. by inhalation or insufflation therapy using, e.g. an aerosol, e.g. through mouth or nose); rectal; vaginal; parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot, for example, subcutaneously or intramuscularly.

Formulations suitable for oral administration (e.g., by ingestion) may be presented as discrete units such as capsules, cachets or tablets, each containing a predetermined amount of the active compound; as a powder or granules; as a solution or suspension in an aqueous or non-aqueous liquid; or as an oil-in-water liquid emulsion or a water-in-oil liquid emulsion; as a bolus; as an electuary; or as a paste.

Formulations suitable for parenteral administration (e.g., by injection, including cutaneous, subcutaneous, intramuscular, intravenous and intradermal), include aqueous and non-aqueous isotonic, pyrogen-free, sterile injection solutions which may contain anti-oxidants, buffers, preservatives, stabilisers, bacteriostats, and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. Examples of suitable isotonic vehicles for use in such formulations include Sodium Chloride Injection, Ringer's Solution, or Lactated Ringer's Injection. Typically, the concentration of the active compound in the solution is from about 1 ng/ml to about 10 mg/ml, for example from about 10 ng/ml to about 1 mg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets. Formulations may be in the form of liposomes or other microparticulate systems which are designed to target the active compound to blood components or one or more organs.

Compositions comprising agents disclosed herein for the treatment of BAF-complex gene mutated or deficient cancer may be used in the methods described herein in combination with standard chemotherapeutic regimes or in conjunction with radiotherapy. Examples of other chemotherapeutic agents include Amsacrine (Amsidine), Bleomycin, Busulfan, Capecitabine (Xeloda), Carboplatin, Carmustine (BCNU), Chlorambucil (Leukeran), Cisplatin, Cladribine (Leustat), Clofarabine (Evoltra), Crisantaspase (Erwinase), Cyclophosphamide, Cytarabine (ARA-C), Dacarbazine (DTIC), Dactinomycin (Actinomycin D), Daunorubicin, Docetaxel (Taxotere), Doxorubicin, Epirubicin, Etoposide (Vepesid, VP-16), Fludarabine (Fludara), Fluorouracil (5-FU), Gemcitabine (Gemzar), Hydroxyurea (Hydroxycarbamide, Hydrea), Idarubicin (Zavedos), Ifosfamide (Mitoxana), Irinotecan (CPT-11, Campto), Leucovorin (folinic acid), Liposomal doxorubicin (Caelyx, Myocet), Liposomal daunorubicin (DaunoXome®) Lomustine, Melphalan, Mercaptopurine, Mesna, Methotrexate, Mitomycin, Mitoxantrone, Oxaliplatin (Eloxatin), Paclitaxel (Taxol), Pemetrexed (Alimta), Pentostatin (Nipent), Procarbazine, Raltitrexed (Tomudex®), Streptozocin (Zanosar®), Tegafur-uracil (Uftoral), Temozolomide (Temodal), Teniposide (Vumon), Thiotepa, Tioguanine (6-TG) (Lanvis), Topotecan (Hycamtin), Treosulfan, Vinblastine (Velbe), Vincristine (Oncovin), Vindesine (Eldisine) or Vinorelbine (Navelbine), or the PARP inhibitors (Olaparib (Lynparza), Rucaparib, Niraparib, Veliparib and Talazoparib).

Administration in vivo can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician.

In general, a suitable dose of the active compound is in the range of about 100 mg to about 250 mg per kilogram body weight of the subject per day. Where the active compound is a salt, an ester, prodrug, or the like, the amount administered is calculated on the basis of the parent compound, and so the actual weight to be used is increased proportionately.

Experimental Examples

Example 1

Methods
Cell Culture

ES2 and TOV21G were obtained from the American Type Tissue Collection. RMG-1, SMOV2, KOC7C, HCH1, OVAS, OVISE, OVMANA, OVTOKO, OVSAYO and KK were courtesy of Dr. Hiroaki Itamochi (Tottori University School of Medicine, Yonago, Japan). Ovarian clear cell carcinoma lines were grown in McCoys with 10% FCS. The identity of cell lines was confirmed by short tandem repeat (STR) typing using the StemElite Kit (Promega) in March 2013. ARID1A HCT116 isogenic cell lines were obtained from Horizon Discovery and grown in McCoys with 10% FCS. Arid1a null and wildtype mouse embryonic stem cells were obtained from Dr Zhong Wang (Harvard Medical School, USA) and grown on gelatin coated plates in DMEM with 10% FCS supplemented with 0.1 mM NEAA, 1 mM sodium pyruvate, 0.1 mM betamercaptothanol and 2000U LIF/ml.

VE-821 siRNA Screen

A siRNA library was purchased from Dharmacon. Genes were selected as described in the main text. Each well contained a SMART pool of four distinct siRNA species targeting different sequences of the target transcript. Each plate was supplemented with negative siCONTROL (12 wells; Dharmacon) and positive control (4 wells, siPLK1, Dharmacon). RNAi screening conditions were optimised and raw CellTitre-Glo (Promega) luminescent viability readings were generated as previously described21. VE-821 or vehicle (DMSO) was added 24 hours after transfection at 1 µM concentration in media and cells were exposed for 5 days. Statistical analysis of the siRNA screen was performed as described in [21]

Chemicals

The ATR inhibitors VE-821 and VX-970 were provided by Vertex Pharmaceuticals. Olaparib and BMN673 were purchased from Selleck Chemicals; cisplatin was purchased from Sigma.

Western Blotting and Antibodies

Whole-cell protein extracts were prepared from cells lysed in NET-N buffer (20 mM Tris pH 7.6, 1 mM EDTA, 1% NP40, 150 mM NaCl) supplemented with protease inhibitor cocktail tablets (Roche, West Sussex, UK). Western blots were carried out with precast Bis-Tris gels (Invitrogen, Paisley, UK). The following primary antibodies were used in this study; ARID1A (Cell Signalling), ARID1B (Cell Signalling), SMARCA4 (Cell Signalling), ATR (Santa Cruz), PT1989 ATR (Gene Tex), Tubulin (Sigma), SMARCB1 (Abcam), γH2AX (Cell Signalling), PARP-1 (Santa Cruz), Ezrin (Cell Signalling), TOP2A (Cell Signalling), Cyclin B1 (Cell Signalling), Lamin A/C (Cell Signalling), ARID2 (Abcam) and PBRM1 (Cell Signalling).

Cellular Viability Assays

Short-term survival assays were performed in 384-well plates. Exponentially growing cells were plated at a concentration of 500 cells/well. Drug was added 24 h after seeding and cells were continuously exposed to the drug for five days, after which cell viability was estimated using CellTitre-Glo luminescence (Promega). For clonogenic assays, cells were seeded in 6-well plates (500 cells/well) and continuously exposed to drug 24!h after seeding for 14 days. Media containing fresh drug was replaced every 72 hours. Cells were fixed with 10% trichloroacetic acid and stained with sulphorhodamine B (Sigma-Aldrich, Gillingham, UK). Colonies were counted manually. All cell-based assays were performed at least in triplicate.

Cell Cycle Analysis DECATENATION

Cells were plated at a density of 2×105 cells per well of a six-well plate and incubated for 24 hours after which ATRi or 0.1% DMSO was added for the indicated period of time. After incubation, adherent cells were harvested and then fixed with cold 50 (v/v) % ethanol in phosphate-buffered saline (PBS). Cells were then treated with RNase A for 30 mins prior to nucleic acid staining with propidium iodide (PI, Sigma). Samples were analyzed on a BD LSR II flow cytometer using BD FACSDiva software (BD Biosciences). For synchronisation experiments cells were incubated with 2 mM thymidine for 12 hours, washed and incubated with media for 16 hours, then incubated in 2 mM thymidine for a further 12 hours. Cells were then released into media containing either VX-970 or DMSO and samples fixed as above for cell cycle analysis.

p-H3 Assay DECATENATION

Following experimental treatment, cells were fixed using cold 50% ethanol and PBS. Prior to analysis, cells were centrifuged and resuspended in 1 mL 0.25% (v/v) solution of Triton-X100 in PBS for 15 minutes. Following centrifugation, cells were resuspended in 100 µL of PBS solution containing 1% (w/v) BSA and 0.75 µg of P-S10 Histone H3 antibody (Jackson ImmunoResearch). Samples were incubated at room temperature for 3 hours. Samples were then centrifuged and washed with PBS solution containing 1% BSA. Cells were subsequently suspended in 100 µL of FITC-labelled goat anti-rabbit secondary antibody (Jackson ImmunoResearch) in a 1:30 dilution in PBS with 1% BSA. Samples were incubated in the dark for 30 minutes and resuspended in PBS solution containing PI (5 µg/mL) and RNase (1 mg/mL). Samples were analyzed on a BD LSR II flow cytometer using BD FACSDiva software (BD Biosciences).

Apoptosis Assay

HCT116 isogenic and OCCC cells were plated in a 96-well plate at high density (15-20,000/well). Twenty four hours later serial dilutions of VX-970 were added for the indicated period of time. ApoTox-Glo™ Triplex Assay (Promega) was performed as per the manufactures protocol.

In Vivo Efficacy Studies

In vivo efficacy studies were performed using HCT116 ARID1A$^{-/-}$, HCT116 ARID1A$^{-/-}$ and TOV21G cells injected subcutaneously in the flank of female CD-1 Nude mice. Animals were treated with either vehicle alone (10% D-α-Tocopherol polyethylene glycol 1000 succinate) or VX-970 (60 mg/kg in 10% D-α-Tocopherol polyethylene glycol 1000 succinate) by oral gavage. Treatment was administered four times weekly for the indicated length of time. Tumours were measured manually by calliper trice weekly and animals were sacrificed when tumours reached >15 mm in any direction.

Anaphase Bridge Analysis

Cells were grown on Poly-lysine coated cover slips for 24 hours prior to exposure to the indicated treatment. Samples were fixed in formaldehyde (4%), permeablised in Triton X-100 (0.2%) and DNA stained with DAPI. Slides were then imaged at 60× on a Leica confocal microscope.

Mitotic Spreads

Following exposure to the indicated treatment, cells were incubated with 0.5% colchicine for 4 hours. Cells were harvested, washed in PBS and incubated in 0.56% KCl at 37° C. for 20 min. Samples were then fixed (3 methanol:1 acetic acid) and DAPI was added. Cell solutions were dropped onto clean coverslips and mitotic spreads imaged at 60× on a Leica confocal microscope.

Results

Genetic Screens Identify ARID1A as an ATRi Synthetic Lethal Partner

To uncover clinically actionable genetic determinants of single-agent ATRi response, a series of high-throughput RNAi chemosensitisation screens were performed where cells were transfected with an siRNA library and then exposed to the a highly potent and selective ATR catalytic inhibitor VE-821 (Ki=13 nM; 15). As a cell line for screening, the p53 mutant, triple negative (ERα-, PR-, ERBB2-ve) breast tumour cell line, HCC1143 was selected based on work that has suggested that ATR inhibitors might show some utility in p53 mutant cancers. To model the effect of ATRi on normal cells, the non-tumour, mammary epithelial cell model, MCF12A was also screened. This confirmed that both cell lines retained a functional ATR activation pathway by assessing cisplatin-induced ATR p.T1989 autophosphorylation[16,17]. To identify clinically actionable effects, the RNAi library included 1280 siRNAs targeting recurrently mutated genes in cancer[18], kinases, due to their inherent tractability as drug targets, and DNA damage response genes[19], given the potential for ATR inhibitors to enhance defects in these processes[7,20]. HCC1143 and MCF12A cells were transfected in a 384 well plate format using the siRNA library and then exposed to either VE-821 (1 µM) or vehicle (DMSO) for a subsequent four days, at which point we estimated cell viability using Cell Titre Glo Reagent (Promega) (FIG. 1A).

Data from the triplicate screens was used to calculate Z scores describing the effect of each siRNA on VE-821 sensitisation21 and identified 150 significant (Z<-2) VE-821 sensitivity-causing effects in HCC1143 and 179 in MCF12A (FIG. 1B,C). ATR siRNA caused significant VE-821 sensitisation, as did siRNAs targeting other ATR activation factors (RAD17, RAD1, RAD9A). siRNA targeting ERCC4 and ATM also sensitised cells to VE-821, consistent with ATRi synthetic lethalities, giving confidence in the results from the screens.

To identify ATRi synthetic lethal effects operating in diverse genetic backgrounds, the HCC1143 and MCF12A data was compared and 30 siRNAs in common were identified that caused VE-821 sensitivity, including those targeting components of the HR/Fanconi Anemia pathway (FANCE, SLX4, PALB2), DNA mismatch repair (MSH4, PMS2) and translesion synthesis (RAD18) pathways (FIG. 1C). We also identified seven tumour suppressor genes in this list (ATM, FANCE, GCP3, IDH1, PALB2, PMS2, ARID1A; FIG. 1C,D). The observation that silencing ARID1A sensitised cells to ATRi was particularly interesting as ARID1A is recurrently mutated in a variety of tumour types (45% ovarian clear cell carcinoma, 14-19% gastric, bladder and hepatocellular tumours and 2-3% breast tumours[13]) and at present no licenced targeted therapy approaches are available for ARID1A mutant tumours.

Figure 2:
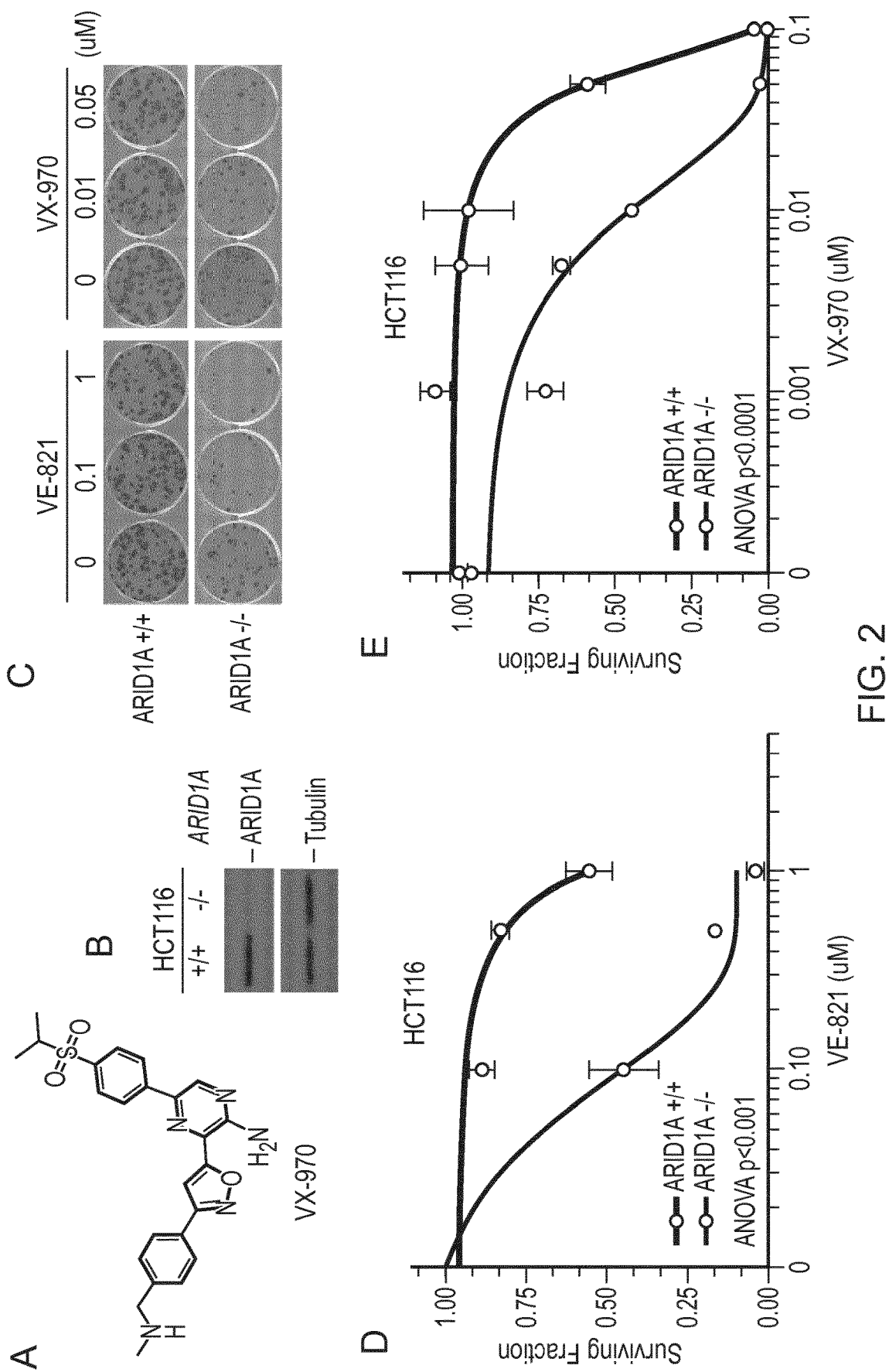
FIG. 2. In vitro ARID1A/ATR synthetic lethality. A. Chemical structure of VX-970. B. Western blot of ARID1A in human ARID1A isogenic HCT116 cells. C. Image of colonies in 6 well-plate clonogenic assay. HCT116 ARID1A isogenic ($^{+/+}$ and $^{-/-}$) cell lines were exposed to increasing concentrations of the VE-821 (0, 0.1, 1 uM) and VX-970 (0, 0.01, 0.05 uM) for 14 days. D and E. Dose response clonogenic survival curve of HCT116 ARID1A isogenic ($^{+/+}$ and $^{-/-}$) cell lines exposed to increasing concentrations of the VE-821 and VX-970 for 14 days. Error bars represent SD from triplicate experiments, ANOVA p-value of <0.0001. F. Area under curve (AUC) box whisker comparison plot for human tumor cell lines exposed to VX-970 for five days. ARID1A wild type tumor cell lines (n=15) were compared to ARID1A mutant cell lines (n=9). Student's t-test p=0.00594. G. Dose response clonogenic survival curve of mouse Arid1a isogenic ES cell lines. Experiment was performed as per (C). Error bars represent SD from triplicate experiments, ANOVA p value of <0.0001. H. Western blot of Arid1a protein expression in mouse ES Arid1a isogenic cells. I. Z score box whisker comparison plot for 86 human tumor cell lines transfected with ATR siRNA. Cells lines were transfected with siRNA and cell viability was estimated five days later by Cell Titre Glo reagent. ATR siRNA Z-scores for ARID1A wildtype (n=65) and ARID1A mutant (n=21) were found to be statistically different (p=0.0084, median permutation test).
Figure 2:
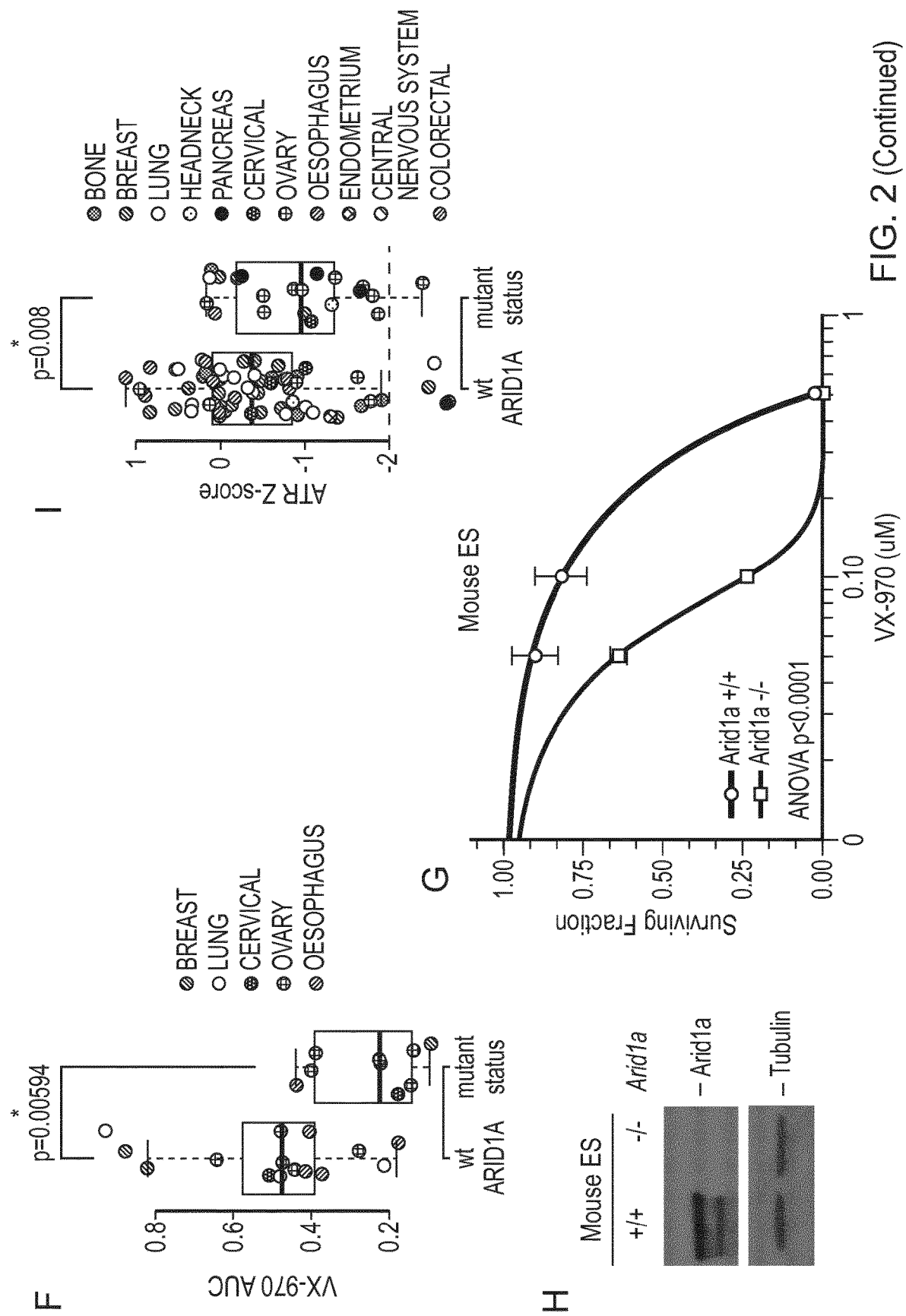

The ARID1A/ATRi synthetic lethal interaction as validated using a number of orthogonal approaches. In HCC1143 cells, a siRNA SMARTPool reduced ARID1A protein levels and significantly enhanced sensitivity to VE-821 (p<0.0001, ANOVA, FIG. 1E,F) as did individual ARID1A siRNAs. ARID1A siRNAs also caused sensitivity to an ATRi currently being assessed in Phase 1 trials, VX-970 (FIG. 2A), suggesting that the synthetic lethality was not specific to VE-821. To assess whether constitutive loss of ARID1A function also resulted in ATRi sensitivity, human colorectal HCT116 isogenic cells containing either wildtype ARID1A (ARID1A$^{+/+}$) or homozygous mutant loss of function ARID1A alleles (p.Q456*/p.Q456*; referred to as ARID1A$^{-/-}$; FIG. 2B) were exploited. In clonogenic survival assays, ATRi exposure significantly impaired the survival of ARID1A$^{-/-}$ cells compared to ARID1A$^{+/+}$ ($p<0.0001$ by ANOVA, FIG. 2C-E). These observations did not appear to reflect a general, nonspecific, sensitivity of ARID1A$^{-/-}$ cells to targeted therapy as neither taxol or methotrexate elicited ARID1A$^{-/-}$ selectivity. The observation of ARID1A synthetic lethality in the HCT116 ARID1A$^{-/-}$ model not only validated the synthetic lethal interaction between ARID1A and ATR inhibition but also established that the effect was not restricted to cells from a breast lineage. ATRi sensitivity in a genetically and histologically diverse panel of tumour cell lines was also assessed, observing that those with loss-of-function ARID1A mutations (n=9) as a group were significantly more sensitive to VX-970 than those without ARID1A mutation (n=15, p=0.005, Student's t-test, FIG. 2F). The magnitude of ATRi sensitivity associated with ARID1A mutant cells was comparable, if not greater than that seen with other candidate biomarkers of ATRi sensitivity such as ATM or ERCC1.

Furthermore, it was found that the ARID1A$^{-/-}$ selectivity of VX-970 was greater than for other proposed ARID1A-targeted agents such as PARP inhibitors (PARPi) or cisplatin[22,23]. To address whether the ATR/ARID1A synthetic lethal interaction was species specific, isogenic Arid1a$^{+/+}$ and Arid1a$^{-/-}$ mouse embryonic stem (ES) cells were studied[24]. In clonogenic assays both VX-970 and VE-821 selectively targeted Arid1a$^{-/-}$ ES cells ($p<0.001$, ANOVA, FIG. 2G,H). Finally, to address the possibility that the ARID1A/ATRi synthetic lethality might be specific to catalytic inhibition of ATR, siRNA sensitivity data generated in 86 human tumour cell lines ([25] and Campbell et al. manuscript in review). It was observed that ATR siRNA had a significantly greater growth inhibitory effect on ARID1A mutant tumour cells (n=21) compared to ARID1A wildtype tumour cells (n=65) (p=0.0084, MP test, FIG. 2I). To confirm this, ATR was silenced by siRNA in HCT116 ARID1A$^{-/-}$ and ARID1A$^{+/+}$ cells, and it was found that ATR siRNA selectively targeted ARID1A$^{-/-}$ cells ($p<0.05$, Student's t-test). Collectively this data suggested that abrogation of ATR function, either by chemical inhibition or by gene silencing was synthetic lethal with ARID1A deficiency.

In Vivo ATR/ARID1A Synthetic Lethality

It was assessed whether an ATRi being assessed in clinical trials, VX-970, showed in vivo efficacy against ARID1A-deficient tumours. Using mice with established HCT116 ARID1A$^{+/+}$ or ARID1A$^{-/-}$ subcutaneous xenografts (FIG. 3A), it was found that VX-970 had no effect on ARID1A$^{+/+}$ xenografts (p=0.43, ANOVA) but significantly inhibited the growth of ARID1A$^{-/-}$ xenografts (p=0.05, ATR/BAF synthetic lethality 9 ANOVA, FIG. 3B). It was also found, in independent experiments, that VX-970 could prevent the establishment of HCT116 ARID1A$^{-/-}$ xenografts (frequency of ARID1A$^{-/-}$ tumour formation=27% for VX-970 treated mice vs. 73% in vehicle treated mice, p=0.027 Fisher's exact test), but had no impact on the incidence of ARID1A$^{+/+}$ xenografts (80% vs. 87% respectively, p=1 Fisher's exact test, FIG. 3C,D). In this experiment, continued VX-970 treatment also dramatically slowed the growth of ARID1A$^{-/-}$ tumours (p=0.015, ANOVA), but did not impair ARID1A$^{+/+}$ xenografts (p=0.63, ANOVA, FIG. 3E,F).

Figure 3:
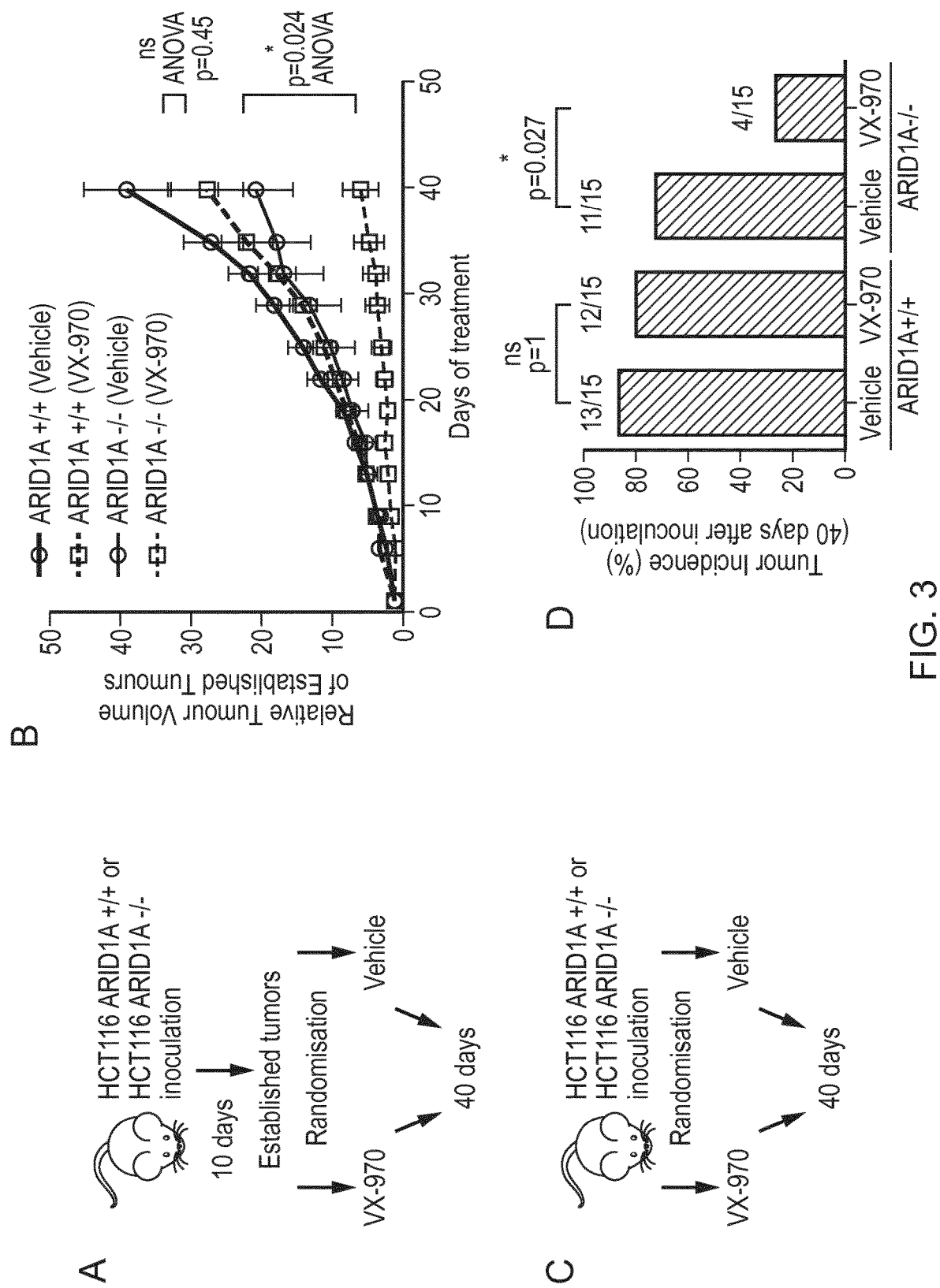
FIG. 3. In vivo ARID1A/ATR synthetic lethality. A. Schematic of VX-970 therapy experiment in mice bearing established HCT116 ARID1A$^{+/+}$ and ARID1A$^{-/-}$ xenografts. Cells were inoculated subcutaneously into nude mice and tumors allowed to establish for 10 days. Mice were then randomized to treatment regimens of either VX-970 (60 mg/kg, 4× weekly by oral gavage) or vehicle. Mice were then treated for a subsequent 40 days. Tumor volume was monitored twice weekly. B. Relative tumor volume plot from (A) showing efficacy of VX-970 and selectivity for ARID1A$^{-/-}$ xenografts* p=0.024, ANOVA. C. Schematic of tumor incidence experiment in mice with non-established HCT116 ARID1A$^{+/+}$ and ARID1A$^{-/-}$ xenografts. Mice were inoculated with cells as before, randomized and then treated with VX-970. VX-970 or vehicle treatment was initiated on the day of cell implantation. Tumor volume was monitored twice weekly and overall tumour incidence was assessed 40 days later. D. Bar chart of incidence 40 days after implantation of HCT116 ARID1A$^{+/+}$ and ARID1A$^{-/-}$ cells. Each group contained 15 animals and fractions above bars indicate the number of animals in which a measurable xenograft formed. *p=0.027 Fisher's exact test. E and F. Tumor growth in experiment described in (C). *p=0.015 ANOVA. G. VX-970 dose response curves from TOV21G (ARID1A mutant) and RMG1 (ARID1A wildtype) cells. Cells were exposed to VX-970 for 5 days. H. Western blot illustrating PARP cleavage in TOV21G cells exposed to increasing concentrations of VX-970 for 24 hours prior to cell lysis. As a positive control cells were exposed to camptothecin (Cpt; 1 uM, 24 hours) prior to cell lysis. PARP-1, cleaved PARP-1 (85 kDa fragment) and tubulin were detected by western blot. I. Bar chart illustrating apoptotic fraction in RMG1 and TOV21G cells exposed to increasing concentrations of VX-970 for 24 hours. Caspase3/7 activity was assessed using Caspase-Glo and total cellular viability was estimated using CellTitre-Glo. Luminescence ratios for Caspase-Glo (i.e. apoptotic cells) and CellTitre-Glo (ie viable cells) was determined for each dose and normalized to DMSO treated samples. *Student's t-test, p<0.05. J. Schematic of VX-970 therapy experiment in mice bearing established TOV21G. Experiment performed as per (A) but with only 28 days treatment. K. Relative tumor volume plot from (J) showing efficacy of VX-970 in TOV21G xenografts *p=0.014, ANOVA. L. Images of TOV21G xenografts after 28 days treatment.
Figure 3:
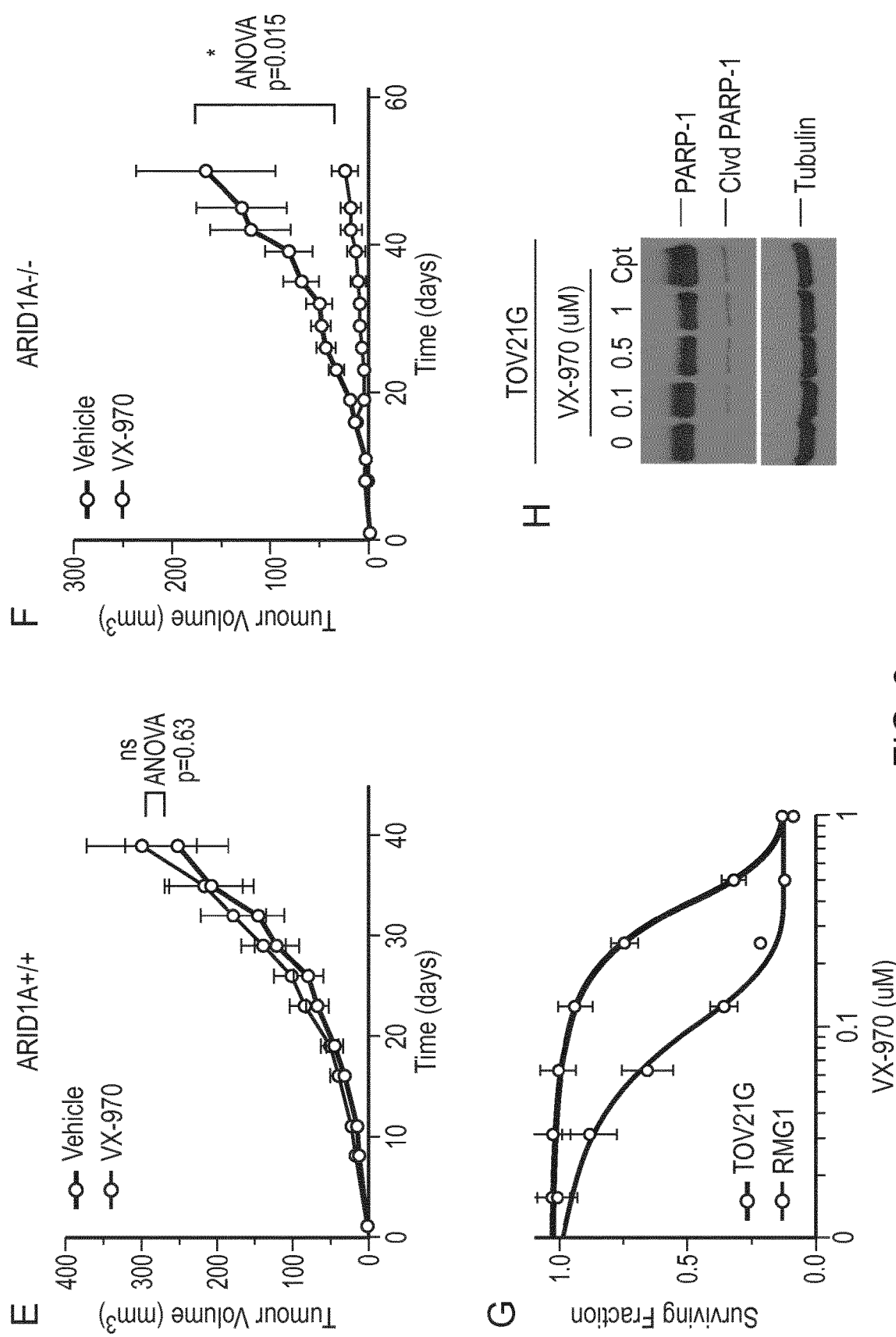
Figure 3:
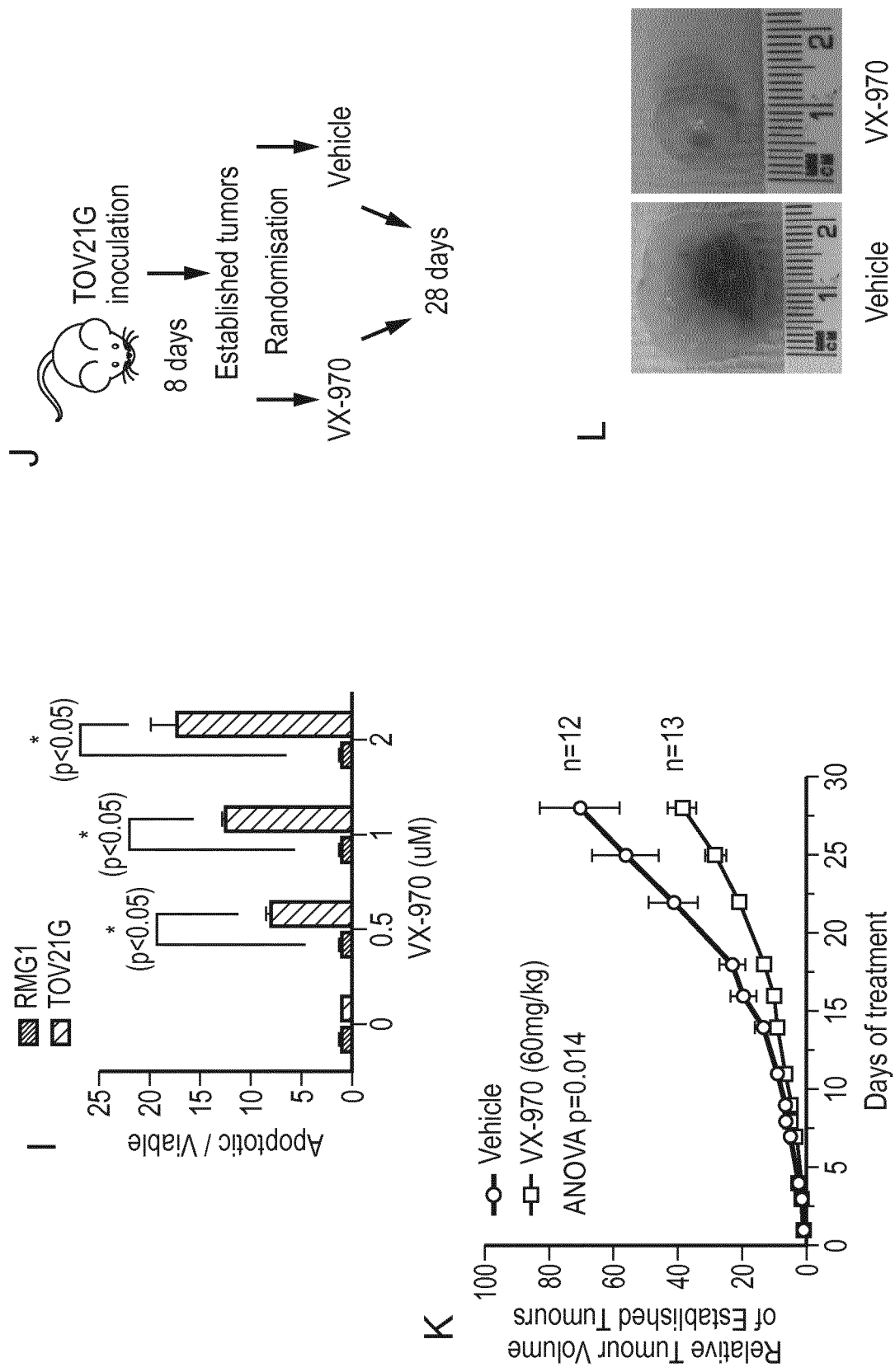

Finally, the in vivo efficacy of VX-970 in a tumor cell line xenograft with a naturally occurring ARID1A mutation was assessed. In in vitro studies, it was found that the ARID1A-deficient TOV21G human ovarian clear cell carcinoma (OCCC) cell line (ARID1A p.548fs/p.756fs) was more sensitive to both VE-821 and VX-970 than the ARID1A wildtype OCCC cell line RMG1 (FIG. 3G, $p<0.005$, AVOVA) and also exhibited a DNA damage and apoptotic response after ATRi exposure (FIG. 3H,I). In vivo, VX-970 treatment significantly inhibited the growth of established TOV21G tumours compared to vehicle (p=0.014, ANOVA, FIG. 3J-L) again suggesting that the ARID1A/ATR synthetic lethality could be exploited in vivo using ATR inhibition.

ATR Inhibition Targets a DNA Decatenation Defect in ARID1A-Deficient Cells

Figure 4:
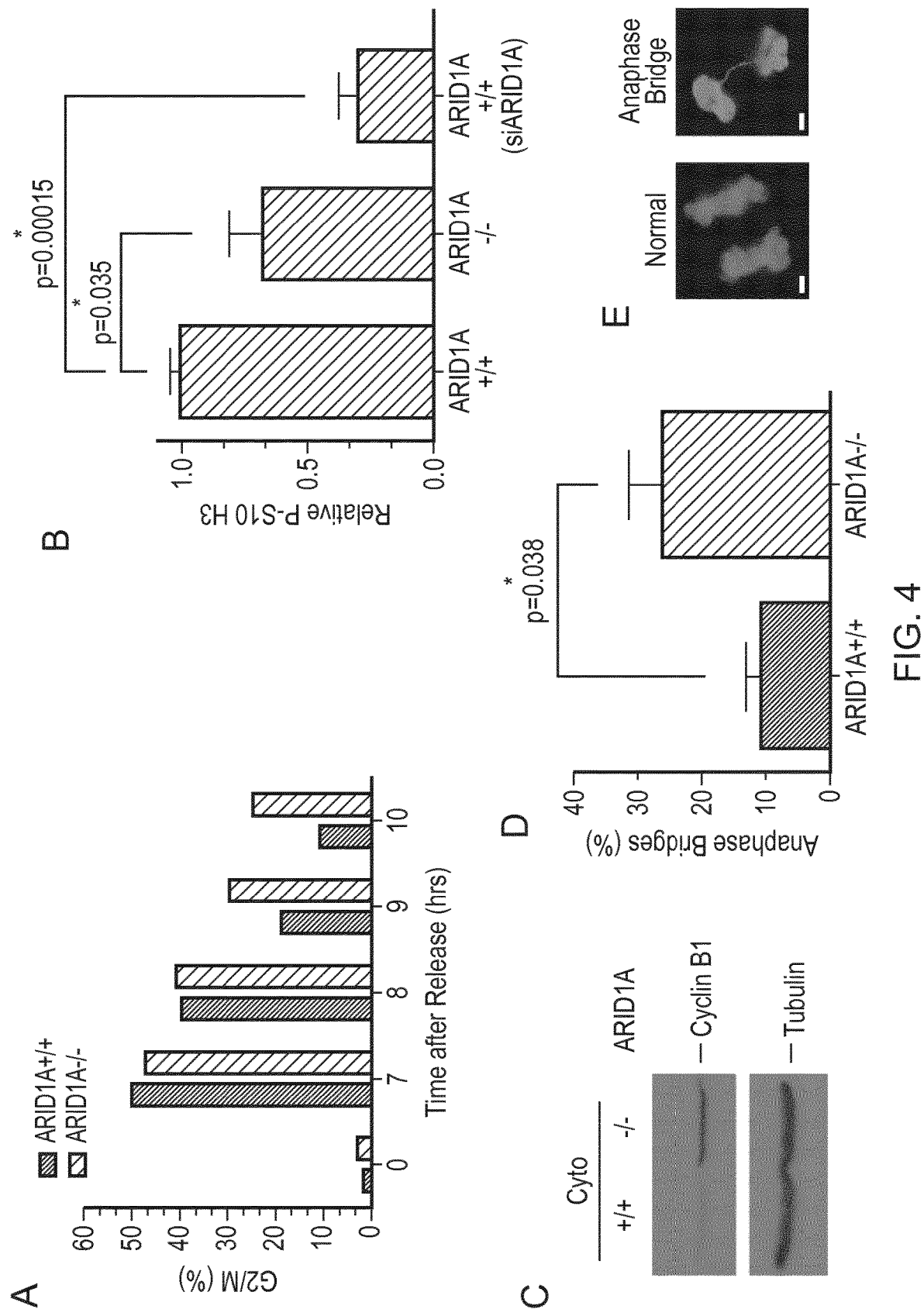
FIG. 4. ARID1A-deficient cells are dependent on a $G_2/M$ cell cycle checkpoint due to a chromosomal decatenation defect. A. Barchart illustrating $G_2/M$ fraction in HCT116 ARID1A$^{+/+}$ and ARID1A$^{-/-}$ cells synchronized in $G_1$/early S phase by double thymidine block and released into fresh media. The percentage of cells in $G_2/M$ phase of the cell cycle is shown 0, 7, 8, 9 and 10 hours after release. B. Barchart illustrating relative amount of cells with phosphorylation of histone H3 on Serine 10. Where shown, HCT116 ARID1A$^{+/+}$ cells were transfected with siARID1A. 48 hours later cells were fixed and stained with FITC-P-S10 Histone H3 and propidium iodide. Mitotic cells (P-S10 positive and 2N) were quantified by FACS. Asterisks indicate a statistically significant difference by Student's t-test between the indicated comparisons. C. Western blot illustrating Cyclin B1 protein in the cytoplasmic fraction of both HCT116 ARID1A$^{+/+}$ and ARID1A$^{-/-}$ cells. D. Bar chart illustrating elevated level of anaphase bridges in HCT116 ARID1A$^{-/-}$ cells compared to ARID1A$^{+/+}$. Cells were stained with DAPI. A minimum of 50 anaphases were scored in 3 biological replicate experiments. *p=0.038, Student's t-test. E. Representative images of a normal anaphase and an anaphase bridge from experiment in (E). Scale bar represents 20 um. F. Western blot of nuclear and chromatin-bound TOP2A. The indicated cell lines were transfected with siRNA targeting ARID1A or control siRNA. 48 hours later, subcellular fractions were isolated and resultant western blots immunoblotted for the indicated proteins. G. Bar chart showing quantification of TOP2A protein derived from (F). H. Western blot of nuclear and chromatin-bound TOP2A from OCCC cell lines. Experiment was performed as per (F).
Figure 4:
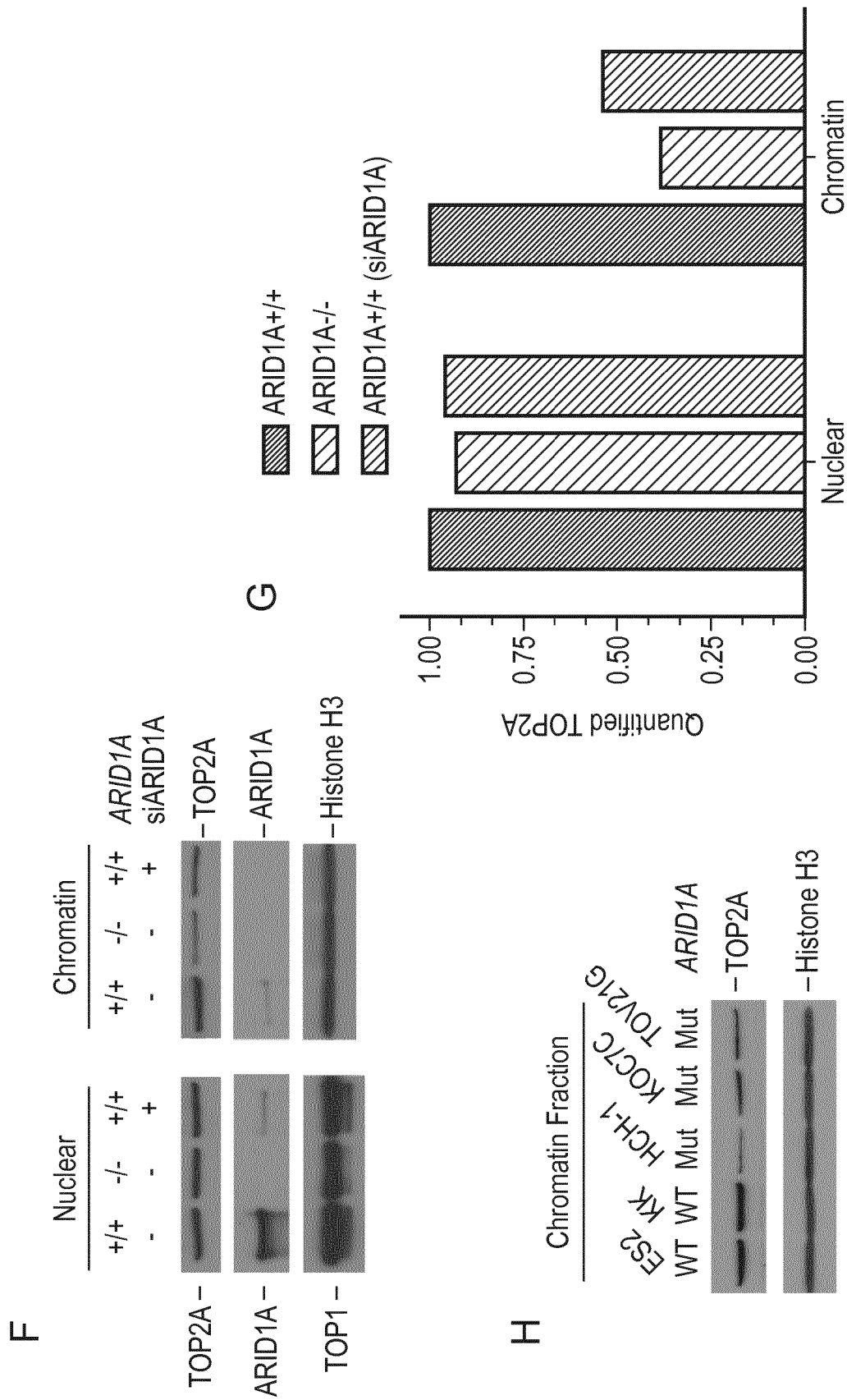

In response to replication fork stress, ATR activity initiates cell cycle arrest at intra-S and G2/M checkpoints[26]. The hypothesis that the sensitivity of ARID1A-deficient cells to ATRi could be in part due to an increased reliance on these checkpoints was examined. To investigate this, ARID1A isogenic cells were synchronised at G1/S using a double-thymidine block and then monitored temporal cell cycle progression after cell cycle release. Both ARID1A$^{+/+}$ and ARID1A$^{-/-}$ cells progressed through S-phase at similar rates, peaking in G2/M after seven hours (FIG. 4A). However, whilst the proportion of ARID1A$^{+/+}$ cells at G2/M fell rapidly between 7-10 hours post synchronisation, ARID1A$^{-/-}$ cells had a delayed progression through G2/M; ten hours after release, 25% of ARID1A$^{-/-}$ cells remained in G2/M compared with only 11% in ARID1A$^{+/+}$ (FIG. 4A). To directly assess the G2/M transition, mitotic entry was monitored by assessing the proportion of phospho-Ser10 Histone H3 positive cells by FACS, noting a 50% reduction in mitotic entry in ARID1A$^{-/-}$ cells vs. ARID1A$^{+/+}$ (FIG. 4B). The subcellular localisation of mitotic cyclin B1 was examined which, under stress conditions, is shuttled to the cytoplasm thereby blocking mitotic entry[27]. Higher cytoplasmic cyclin B1 levels in ARID1A$^{-/-}$ cells compared to ARID1A$^{+/+}$ cells was observed, consistent with increased engagement of the G2/M checkpoint (FIG. 4C). This suggested that both constitutive and induced loss of ARID1A caused a delay in cell cycle progression through G2/M.

G2/M cell cycle checkpoints can be activated by various cellular stresses including failure to complete chromosomal decatenation, a process mediated by Topoisomerase IIa (TOP2A)[28]. Recently, the BAF complex has been shown to be required for the localisation of TOP2A to chromatin[29]. In mouse cells with BAF complex defects, impaired TOP2A localization results in a defect in DNA decatenation[29]. It was determined whether a DNA decatenation defect might also exist in ARID1A defective cells by assessing the frequency of anaphase bridges, a consequence of delayed decatenation. ARID1A$^{-/-}$ cells exhibited a significant increase in the number of anaphase bridges compared to ARID1A$^{+/+}$ cells (p=0.038, Student's t-test, FIG. 4D,E). It was also noted that ARID1A$^{-/-}$ cells exhibited lower levels of chromatin-bound TOP2A, compared to ARID1A$^{+/+}$ cells, as did cells in which ARID1A expression had been silenced by siRNA (FIG. 4F,G). Amongst a panel of OCCC cell lines we also found that those with ARID1A mutations exhibited a reduction in chromatin bound TOP2A, compared to ARID1A wild type cells (FIG. 4H). These observations suggested that ARID1A deficient human tumour cells have a defect in TOP2A-mediated chromosome decatenation.

Figure 5:
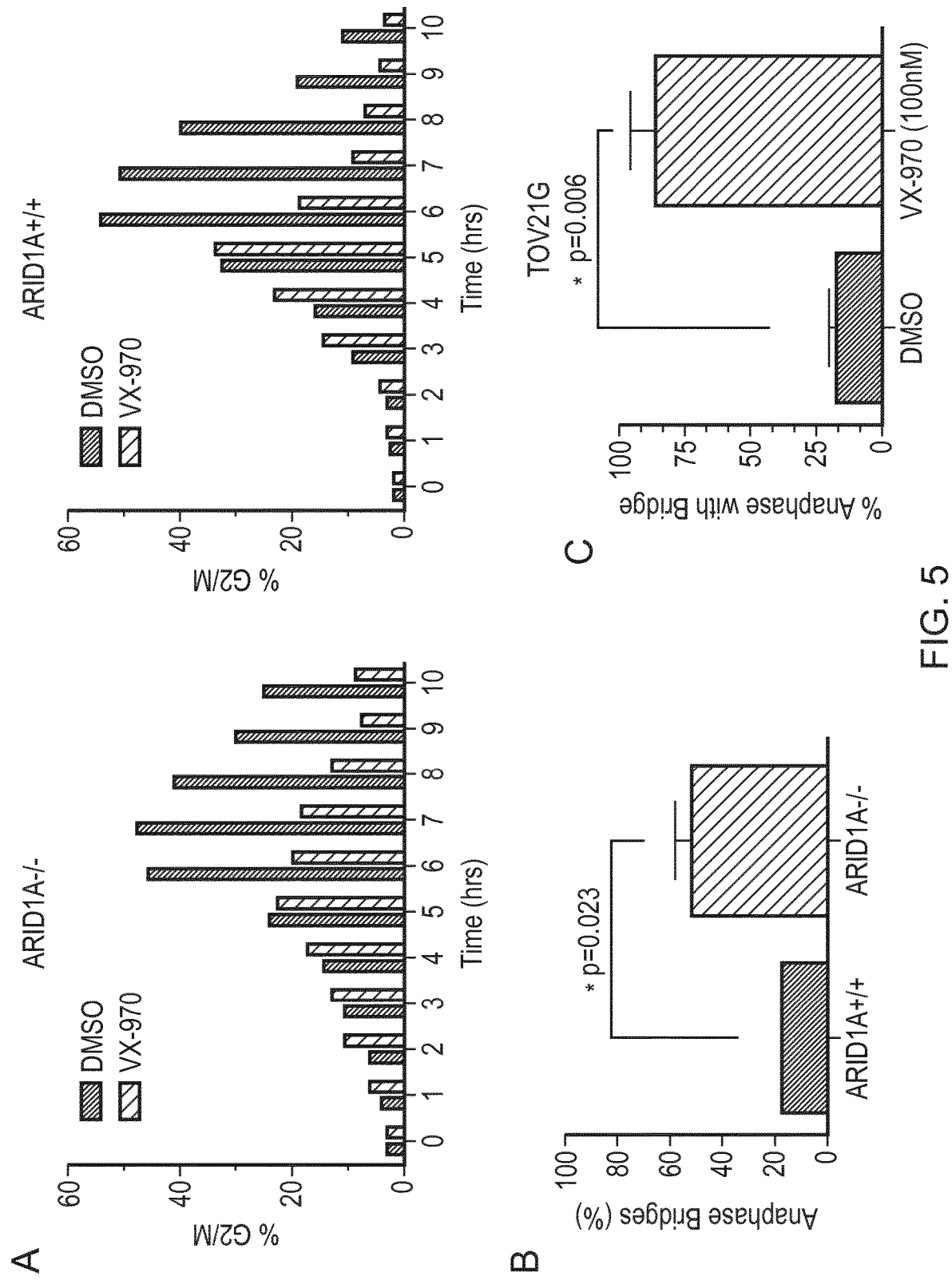
FIG. 5. ATRi effect on cell cycle progression, chromosomal instability, DNA damage and apoptosis. A. Barchart illustrating $G_2/M$ fraction in HCT116 ARID1A$^{+/+}$ and ARID1A$^{-/-}$ cells synchronized in $G_1$/early S phase by double thymidine block and released into fresh media containing DMSO or VX-970 (500 nM). The percentage of cells in G2/M was measured by FACS following PI staining. B. Bar chart illustrating increased level of anaphase bridges in HCT116 ARID1A$^{-/-}$ and ARID1A$^{+/+}$ cells exposed to VX-970 (0.5 uM, 8 hours). Cells were stained with DAPI. A minimum of 50 anaphases were scored in 3 biological replicate experiments. *p=0.023, Student's t-test. C. Bar chart illustrating frequency of anaphase bridges in TOV21G cells exposed to VX-970 (0.5 uM) or DMSO for 8 hours prior to fixation. Experiment performed as for (B). p=0.006 Student's t-test. D. Mitotic spread images from HCT116 ARID1A$^{+/+}$ and ARID1A$^{-/-}$ cells following exposure to either DMSO or VX-970 (1 uM). Scale bar represents 20 um. E. Bar chart illustrating extent of chromosomal abnormalities in HCT116 ARID1A$^{+/+}$ and ARID1A$^{-/-}$ cells exposed to VX-970 (1 uM). *p<0.05, Student's t-test. F. Western blot illustrating γH2AX in HCT116 ARID1A$^{+/+}$ and ARID1A$^{-/-}$ cells exposed to VX-970 (0.5 uM) for the indicated time prior to cell lyses. G. Bar chart illustrating apoptotic fraction in cells exposed to increasing concentrations of VX-970 for 24 hours. Experiment as per FIG. 3I. H. Western blot illustrating PARP cleavage in HCT116 ARID1A$^{+/+}$ and ARID1A$^{-/-}$ cells exposed to VX-970. Experiment performed as per FIG. 3H.
Figure 5:
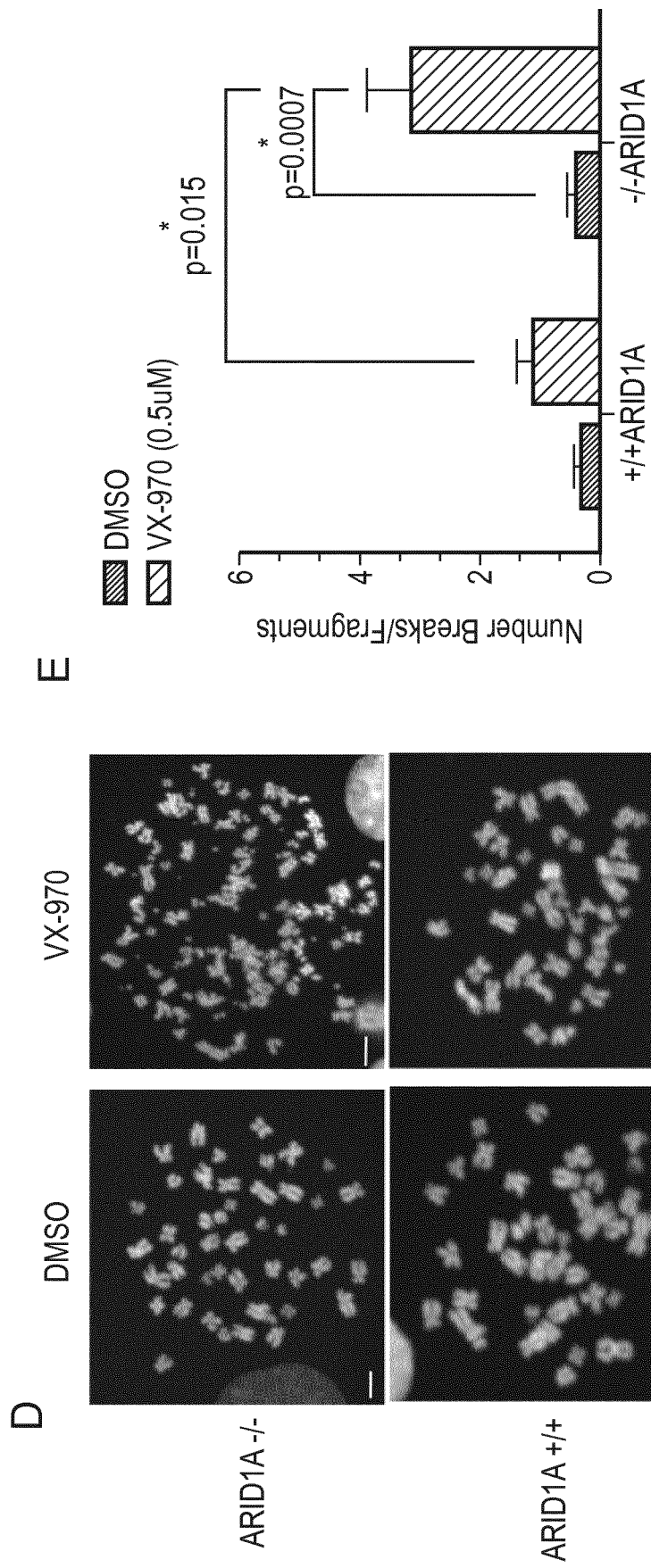
Figure 5:
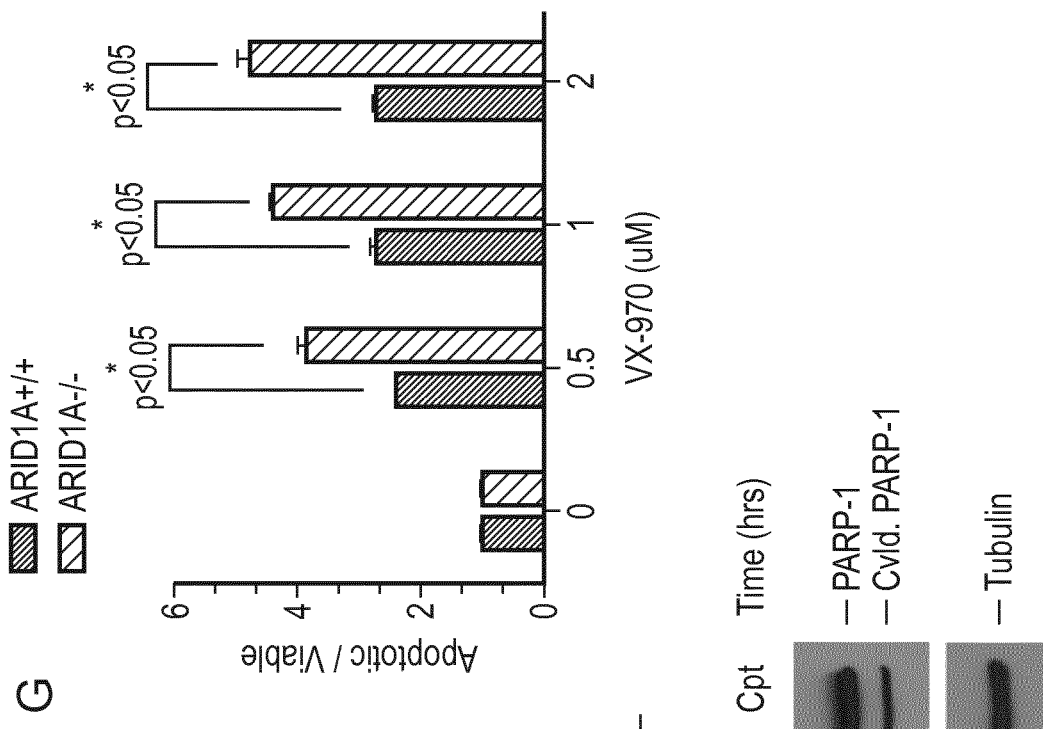
Figure 5:
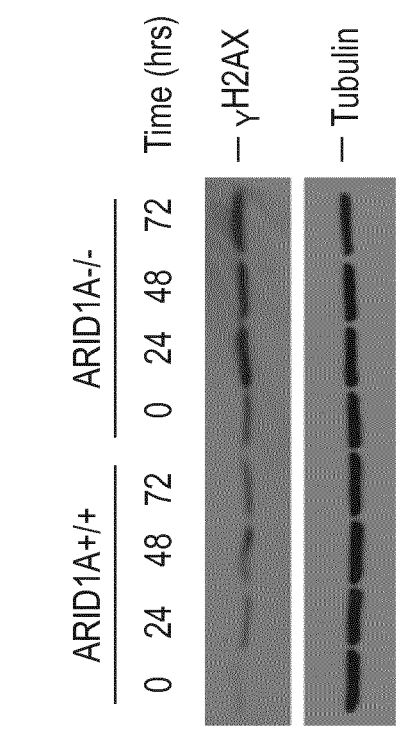
Figure 5:
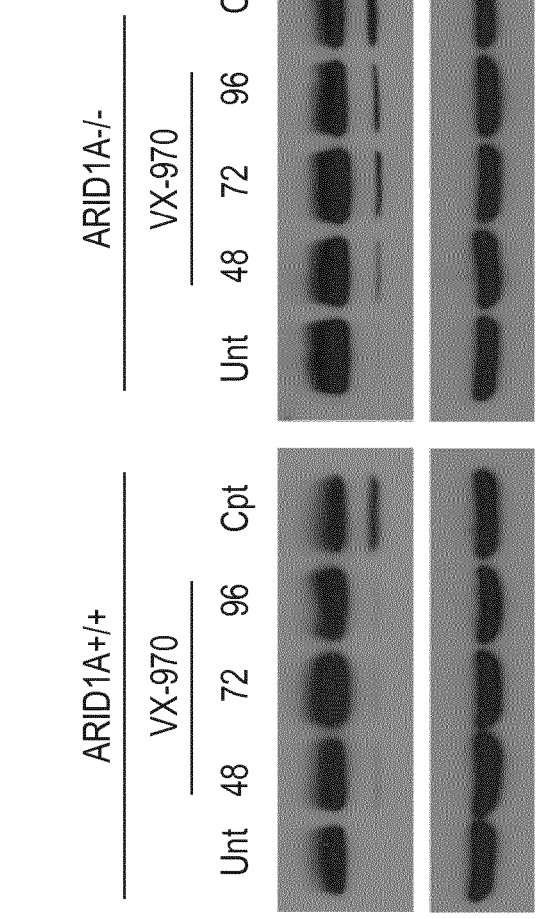

ATR has been implicated in the initiation of a G2/M checkpoint following failure to fully decatenate chromosomes[27,30]. This lead to the hypothesis that inhibition of ATR might relieve the G2/M checkpoint caused by the decatenation-defect in ARID1A-deficient cells, and that this might contribute to synthetic lethality. Assessing cell cycle progression of synchronized cells, it was found that VX-970 abrogated the G2/M delay previously seen in ARID1A$^{-/-}$ cells (FIG. 5A). ATRi-induced abrogation of the G2/M checkpoint also enhanced the frequency of anaphase bridges in ARID1A$^{-/-}$ HCT116 cells (p=0.023, Student's t-test, FIG. 5B) and in ARID1A null TOV21G cells (p=0.006 by Student's t-test, FIG. 5C), presumably as the enhanced transition through G2/M caused by ATR inhibition, limits the ability to effectively decatenate sister chromatids.

To assess the impact of these events on genomic integrity, we examined mitotic chromosomes from VX-970 exposed ARID1A isogenic cells. VX-970 elicited a significant enhancement in the frequency of chromosomal aberrations in ARID1A$^{-/-}$ cells (p=0.0007, Student's t-test, FIG. 5D,E). In addition, it was observed that induction of γH2AX induction by VX-970, an effect that was more pronounced in ARID1A$^{-/-}$ cells (FIG. 5F). A similar γH2AX response was also observed in ARID1A-deficient TOV21G cells (FIG. 3B). In addition to these effects, VX-970 exposure caused an ARID1A-selective apoptotic response as shown by higher caspase-3/7 activation in ARID1A$^{-/-}$ cells compared to ARID1A$^{+/+}$ cells (p<0.05 by Student's t-test, FIG. 5G), an effect also observed in TOV21G (ARID1A mutant OCCC) but not RMG1 (ARID1A wild type OCCC) cells (FIG. 3C). The induction of apoptosis by measuring PARP-cleavage was also assessed. Camptothecin elicited similar levels of cleavage in both ARID1A$^{-/-}$ and ARID1A$^{+/+}$ cells, suggesting both genotypes possessed a functional apoptotic response. In contrast, VX-970 caused far higher levels of PARP-cleavage in ARID1A$^{-/-}$ cells than in ARID1A$^{+/+}$ cells (FIG. 5H).

Inactivation of Additional BAF Components Sensitizes Cells to ATRi

Figure 6:
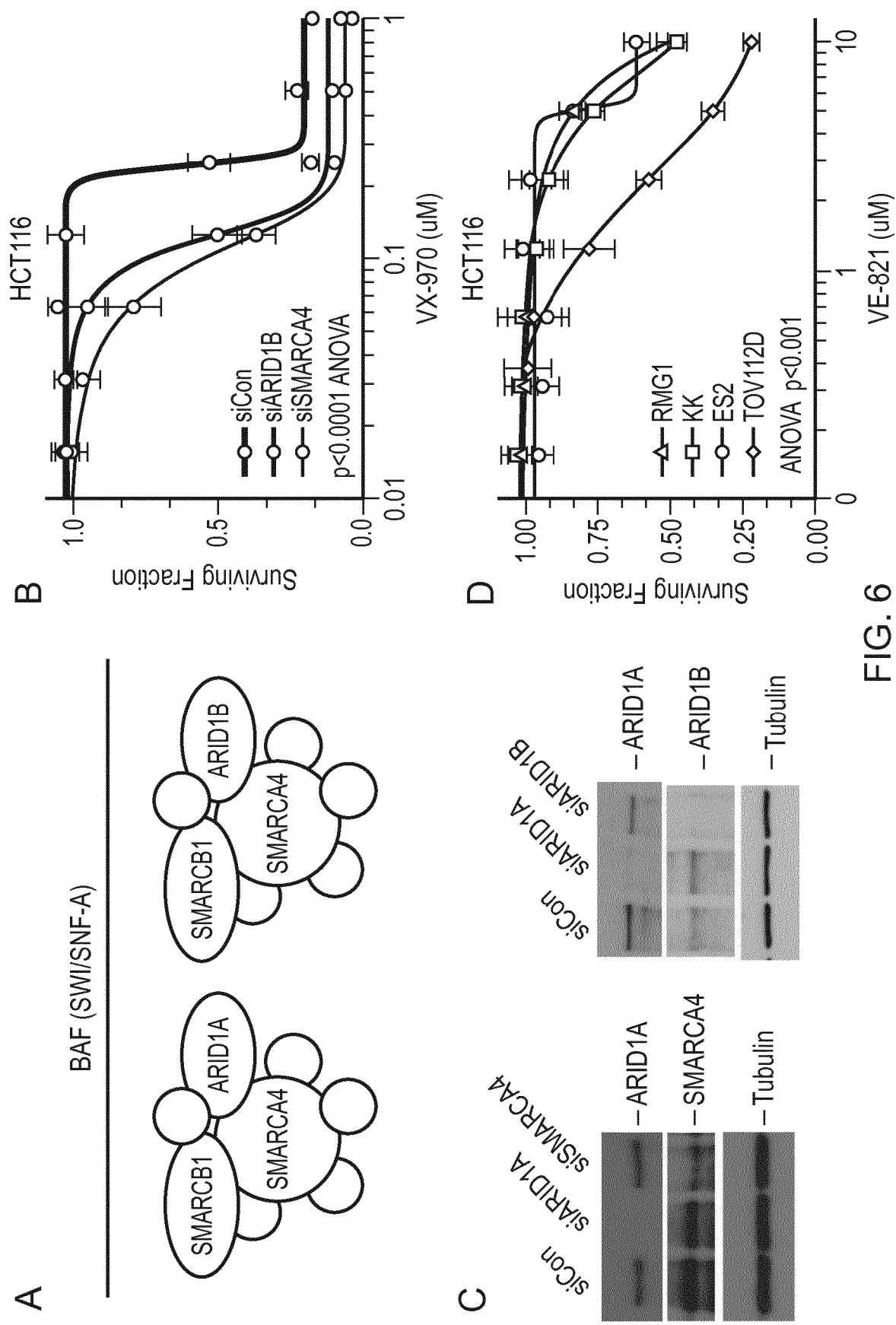
FIG. 6. BAF complex deficiency causes sensitivity to ATR inhibition. A. Schematic of BAF complex composition in human cells. B. VX-970 dose response curves from HCT116 cells transfected with siRNA targeting ARID1B or SMARCA4. 48 hours after transfection cells were exposed to VX-970 for 5 days. Error bars represent SD from triplicate experiments. p<0.0001, ANOVA for siARID1B and siS-MARCA4 vs. siCON. C. Western blots illustrating ARID1B and SMARCA4 silencing in experiment (B). D. VX-970 dose response curves from four OCCC cell lines, 3 SMARCA4 wildtype (blue; RMG1, KK and ES2) and 1 SMARCA4 mutant (red; TOV112D). E. Bar chart illustrating surviving fraction after five days VX-970 exposure in HCC1143 and Hela cells transfected with siRNA targeting either SMARCA4 or ARID1A *p<0.05 by Student's t-test compared to siCon. F. Western blot illustrating level of chromatin bound TOP2A in HCT116 cells transfected siRNA targeting ARID1A, ARID1B or SMARCA4. Cells were analysed 48 hours after transfection. G. A model for the proposed mechanism driving the sensitivity of ARID1A-deficient cells to ATRi. Loss of function genomic alterations to ARID1A (or ARID1B/SMARCA4) lead to dysfunction of the BAF complex. This in turn causes decreased binding of TOP2A to chromatin, reducing the efficiency of chromosomal decatenation. The decatenation defect activates an ATR-dependent, $G_2/M$ cell cycle checkpoint, allowing the cell to resolve catenated chromosomes. BAF-deficient cells exposed to an ATRi progress into mitosis with catenated chromosomes. This leads to DNA breakage, chromosomal instability and ultimately apoptosis.
Figure 6:
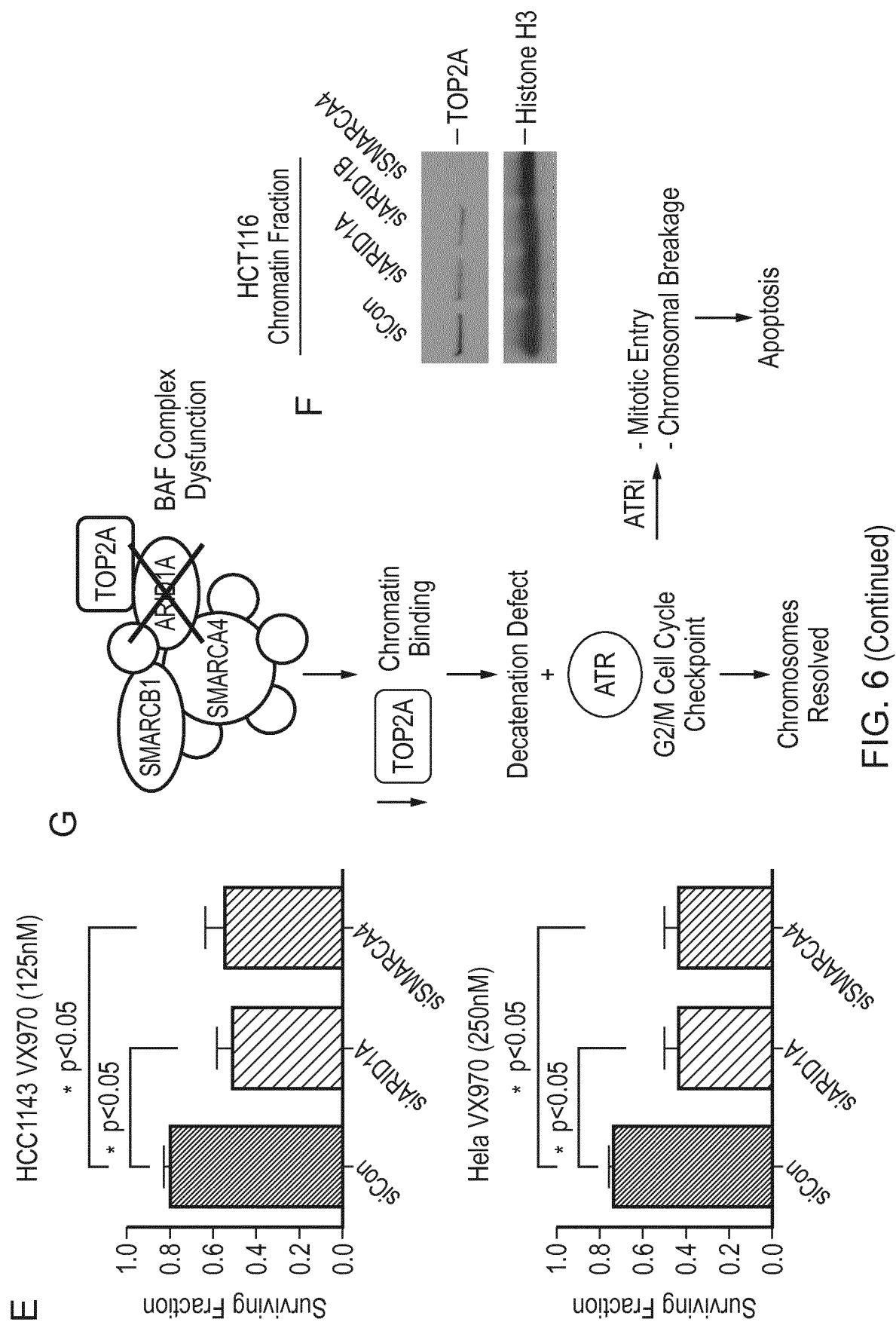

ARID1A is a component of the BAF complex. Experiments to identify whether additional BAF components displayed similar synthetic lethal interactions with ATRi were carried out (FIG. 6A). Silencing of SMARCA4, ARID1B or SMARCB1 individually enhanced sensitivity of HCT116 cells to VX-970 (p<0.0001, ANOVA, FIG. 6B,C). It was also found that TOV112D cells, an OCCC cell line with a loss-of-function SMARCA4 mutation (p.L639fs*7) were significantly more sensitive to ATRi than OCCC cell lines wildtype for both ARID1A and SMARCA4 (FIG. 6D). In HCC1143 and HeLa cells, VX-970 sensitivity caused by SMARCA4 silencing was comparable to that caused by ARID1A siRNA (FIG. 6E). It was also found that silencing of either SMARCA4 or ARID1B in HCT116 cells significantly reduced chromatin-bound TOP2A levels (FIG. 6F), replicating the effect seen for ARID1A dysfunction. These results suggested that a canonical function of ARID1A, namely its role as part of the BAF complex, might be critical to determining ATR inhibitor responses.

Discussion

The data underlying the present invention suggests that ATR inhibitors could have potential as single agent treatments for ARID1A defective cancers and those with other defects in the BAF complex. The highly recurrent nature of ARID1A mutations in human cancer and the availability of clinical ATR inhibitors suggests that once Phase 1 clinical trials are complete, biomarker driven proof-of-concept trials could be instigated to assess the efficacy of these agents. These could be conducted in cancer types where there is a high frequency of ARID1A mutation, such as ovarian clear cell carcinoma, where standard of care therapeutic responses are also limited and few targeted approaches exist. It was also found that ARID1A defects caused ATR inhibitor sensitivity in models from other cancer histologies (for example breast and colorectal cancer), it is also possible that this approach could have wider utility. Likewise, the observation that defects in additional BAF tumour suppressor genes also caused sensitivity to ATR inhibition could also suggest a wider utility for ATR inhibitors. Finally, as one of the challenges with identifying synthetic lethal effects is discriminating those readily abrogated by additional molecular alterations from those that are resistant to these effects[31], it was noted that the ARID1A/ATR synthetic lethal interaction operates in a variety of cellular model systems and thus is likely resilient to additional molecular alterations and could be suitable for clinical assessment.

Mechanistically, the present data suggest the following model for the ARID1A/ATR inhibitor synthetic lethality (FIG. 6G): (i) ARID1A-deficiency causes reduced TOP2A chromatin binding (FIG. 4F); (ii) this results in a DNA decatenation defect (FIG. 4D,E), and as a consequence, G2/M checkpoint activation (FIG. 4A,B,C); (iii) abrogating this cell cycle checkpoint, via ATRi, forces ARID1A-defective cells into mitosis with catenated-DNA (FIG. 5A); finally (iv) the subsequent shearing of catenated-DNA during cytokinesis causes DNA double strand breaks, gross chromosomal instability and apoptosis (FIG. 5D-H). There might be other additional mechanisms that could also contribute to this effect. For example, reduction in ATR function has also been associated with increased ATRi sensitivity[10] and it is possible that ATR activity explanation for our observations. This mechanism might also suggest the possibility that other decatenation-defective cancers could be targeted with ATRi might be impaired in ARID1A mutant cells, although we detected robust ATR protein expression and autophoshorylation in a range of ARID1A-defective tumor cells. Alternatively, cells utilizing the ALT pathway of telomere maintenance are also sensitive to ATRi32, and this might also contribute, although none of the models used here are ALT-positive. Overall, the decatenation defect to which the ARID1A/ATR synthetic lethality appears to be the most straightforward mechanism underlying these observations and one which also suggests the possibility that other decatenation-defective cancers could be targeted with ATRi.

Example 2

One of the more recently used approaches to identifying therapeutic targets in cancer has been to identify and exploit genetic dependencies, such as synthetic lethal and gene addiction effects, that are associated with particular cancer driver gene defects. For example, the synthetic lethal interaction between BRCA1 or BRCA2 tumour suppressor genes and small molecule PARP inhibitors provides the rationale for using PARP inhibitors in the treatment of BRCA1/2 mutant ovarian and prostate cancers (Lord, Tutt et al. 2015, Mateo, Carreira et al. 2015). This particular synthetic lethal interaction targets tumour suppressor gene defects by inhibiting a component of the DNA Damage Response (DDR) molecular network, PARP1. In human cells, as in lower organisms, the DDR consists of a series of overlapping mechanisms that maintain the integrity of the genome in the face of DNA damage (Lord and Ashworth 2016). One of the key elements in several conserved DDR pathways is the kinase ATR (Ataxia telangiectasia and Rad3 related). ATR is activated in response to single stranded DNA (ssDNA) that accumulates in the cell under conditions that cause replication fork stalling (e.g. uncoupling of the replicative helicase from DNA polymerase) or during double-strand break (DSB) repair (Nam and Cortez 2011). In these scenarios, ssDNA is bound by human replication protein A (RPA), which recruits ATR and ATR-interacting protein (ATRIP), which facilitates ATR activation. Active ATR phosphorylates serine/threonine residues on multiple substrate proteins including p53, histone H2AX and CHK1 kinase. Via these target proteins, ATR promotes cell cycle arrest in S-phase and the stabilization of stalled replication forks. These events allow the repair of DNA damage before cells continue into G2 and mitosis. ATR is therefore critical for maintenance of genomic integrity under conditions that cause replicative stress and other forms of DNA damage (Nam and Cortez 2011, Gaillard, Garcia-Muse et al. 2015).

The importance of ATR in the cell cycle and the maintenance of genomic integrity has led to much interest in the therapeutic potential for ATR inhibitors in cancer. Several small-molecule ATR inhibitors are currently under investigation in Phase I clinical trials (NCT02157792, NCT02223923). Successful clinical application of these drugs will require the identification of patient populations most likely to respond, and in this regard several studies have aimed to identify biomarkers of ATR inhibitor sensitivity. Similar to the example of PARP inhibitors as a therapy for BRCA1/2 mutant cancers (Lord and Ashworth 2016), synthetic lethal interactions have been shown to exist between ATR and several DDR-associated genes including p53 when combined with cisplatin (Reaper, Griffiths et al. 2011, Pires, Olcina et al. 2012, Huntoon, Flatten et al. 2013, Josse, Martin et al. 2014), ERCC1 (Mohni, Kavanaugh et al. 2014), XRCC1 (Sultana, Abdel-Fatah et al. 2013) and ATM (Kwok, Davies et al. 2015, Kwok, Davies et al. 2015). Although SS is a disease often treated with DNA damaging chemotherapy, little is known about the dependency of SS tumor cells upon elements of the DDR networks.

Here, we set out to identify novel therapeutic targets for SS by performing a series of parallel high-throughput small interfering RNA (siRNA) screens in SS cell lines. Using this approach, we identified an unexpected dependency in SS cells upon ATR. This genetic dependency was not only evident by silencing of the ATR gene, but importantly could also be exploited and targeted using clinical small molecule ATR inhibitors.

Results

Figure 7:
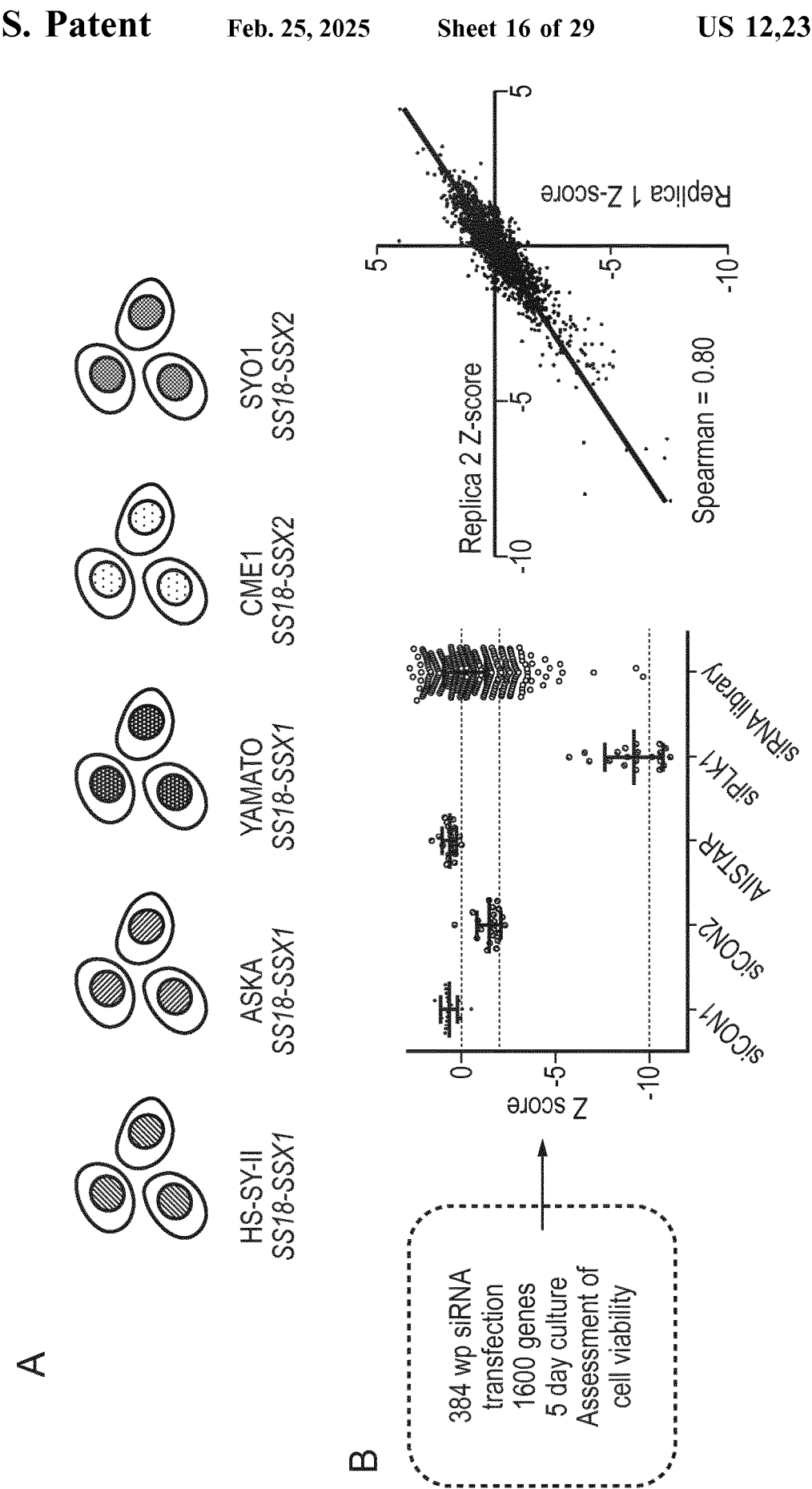
FIG. 7. Genetic dependency profiling identifies ATR as a genetic dependency in synovial sarcoma tumour cells. A. Synovial sarcoma (SS) tumour cell lines used in five parallel siRNA screens. B. Schematic of siRNA screens (left), siRNA Z scores from HS-SY-II indicating high efficiency transfection (as illustrated by low siPLK1 Z scores, middle) and example replica siRNA Z scores from two HS-SY-II siRNA screens (right). C-E. Candidate genetic dependencies in the SS tumour cell lines identified in the siRNA screens. siRNA Z scores are shown for the five SS tumour cell lines ("SS") compared to non-SS tumour cell lines ("Panel"). p values shown are derived from median permutation t tests.
Figure 7:
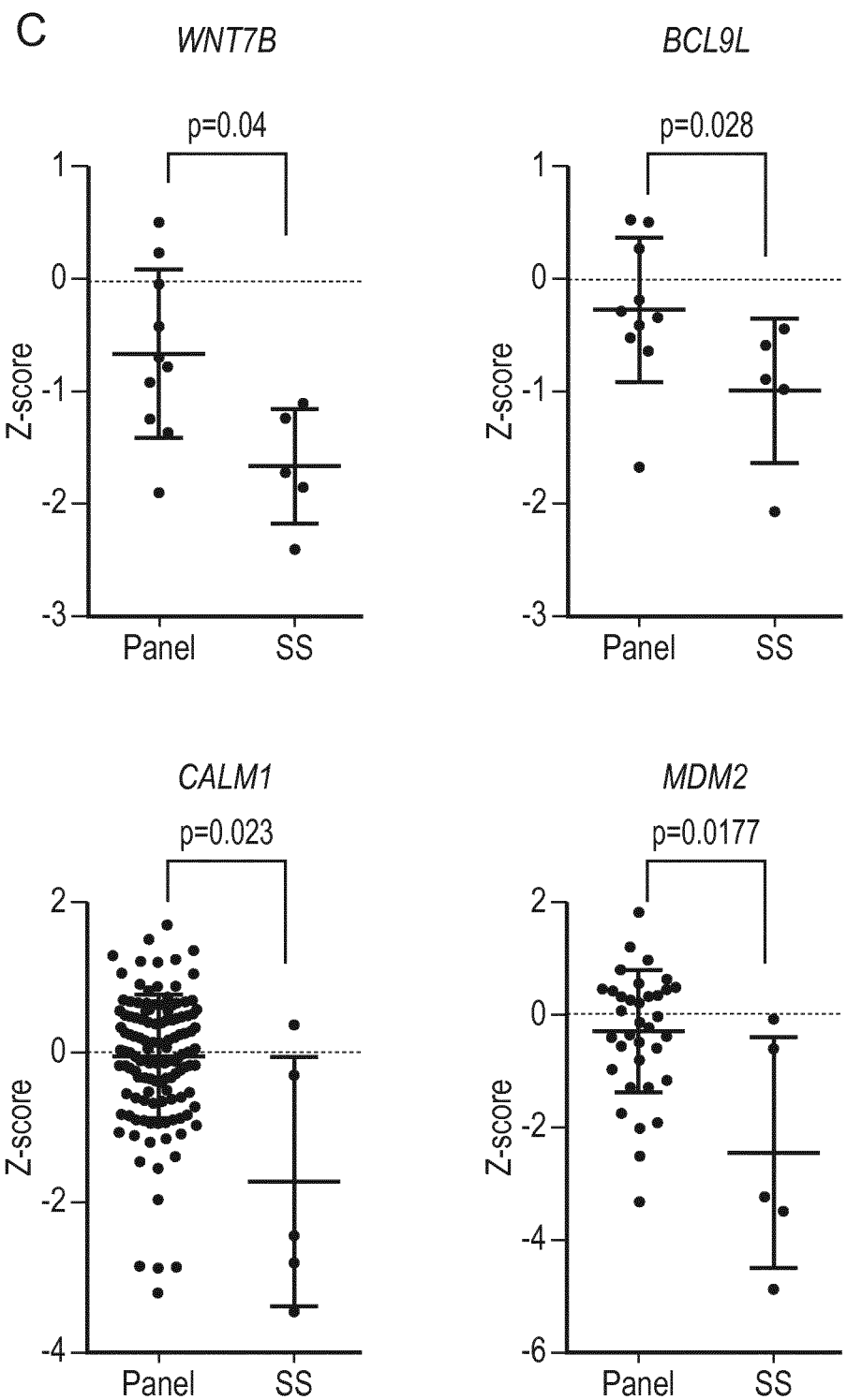
Figure 7:
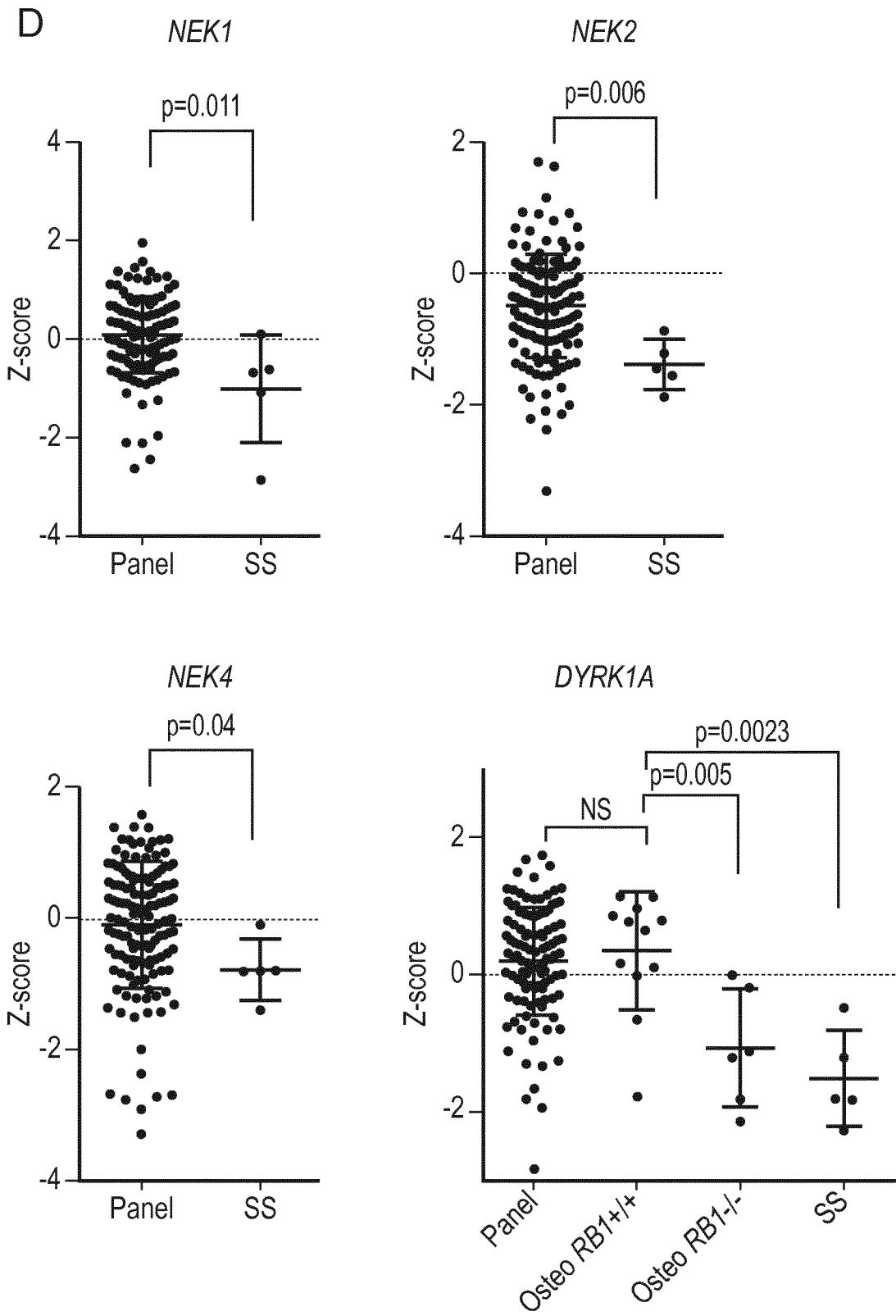
Figure 7:
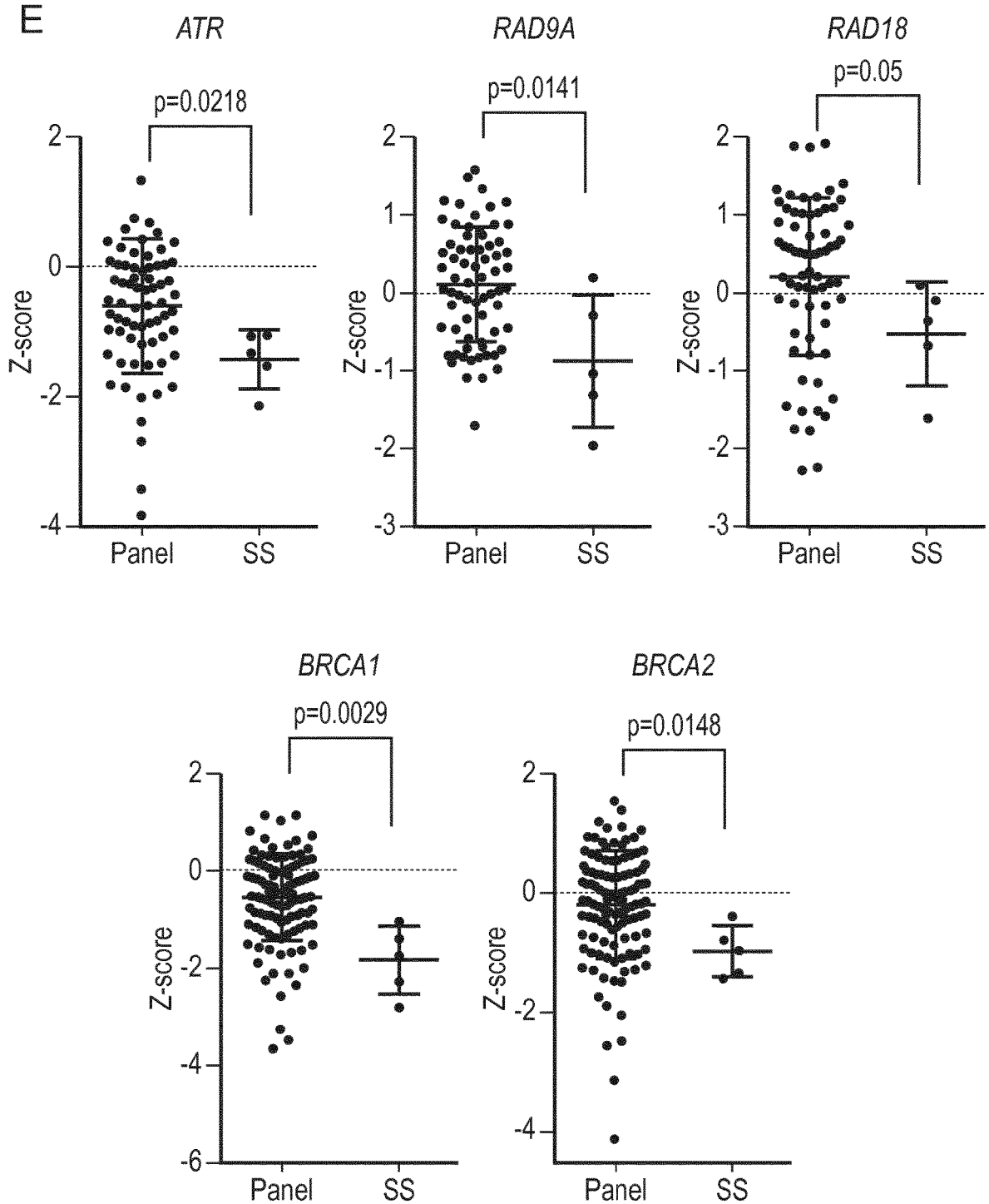

RNA Interference Profiling of Synovial Sarcoma Tumour Cell Lines Identifies ATR as a Candidate Genetic Dependency To identify candidate therapeutic targets in synovial sarcoma, we carried out large-scale RNA interference screens in five commonly-used SS tumor cell lines; HS-SY-II, ASKA, YAMOTO, CME1 and SYO1 (FIG. 7A). These tumour cell lines were selected as these harbour one of the two most common fusions in SS, (SS18-SSX1 or SS18-SSX2) and were amenable to high-efficiency siRNA transfection in a 384 well plate format in each model (example shown in FIG. 7B). After optimising transfection conditions, each tumour cell line was reverse-transfected with a 384-well plate-arrayed siRNA library designed to target 1600 genes, including 720 kinases and kinase-related genes, Wnt pathway genes, DNA repair genes and genes recurrently altered in human cancers (defined by the Cancer Gene Census). Kinases were selected based on their pharmacological tractability as drug targets whilst Wnt-related genes were selected as this molecular pathway has been implicated in the pathogenesis of synovial and other soft tissue sarcomas (Vijayakumar, Liu et al. 2011, Barham, Frump et al. 2013, Trautmann, Sievers et al. 2013). After siRNA transfection, cells were continuously cultured for an additional five days, at which point cell viability was estimated using CellTiterGlo luminescence assay (Promega). In totality, we carried out three replica screens for each cell line and combined the data from these replicas in the final analysis, calculating robust Z scores (see methods) for each siRNA to estimate its effect on tumour cell viability.

To identify genetic dependencies that might be specific to SS, we compared the siRNA Z scores in the SS tumour cell lines to kinome siRNA Z score profiles recently described for 117 tumour cell lines from a diverse set of cancer histotypes (Campbell, Ryan et al. 2016). We augmented this data with additional kinome siRNA screens in 40 additional tumour cell lines, cancer gene census/DNA repair library siRNA screens in 74 tumour cell lines and Wnt pathway siRNA screens in a total of 15 tumour cell lines. In comparing the siRNA profiles in the SS models, we noted a series of candidate SS genetic dependencies, including those associated with Wnt signalling (e.g. the Wnt ligand Wnt7B and the β catenein interacting protein, BCL9L PMID: 18627596, FIG. 7C), the druggable Never in Mitosis-A (NIMA) family members PMID: 23132929 NEK1,2 and 4 and the DREAM complex kinase, DYRK1A (FIG. 7D). Previously we found that DYRK1A is synthetic lethal with RB1 (pRb) tumour suppressor defects in osteosarcoma (OS) (Campbell, Ryan et al. 2016). We found the sensitivity of the SS tumour cell lines to DYRK1A siRNA to be of a scale equivalent to that seen in RB1 null OS tumour cell lines (FIG. 7D).

We also found the SS tumour cell lines to be sensitive to siRNA designed to target DNA repair proteins, including Ataxia telangiectasia and Rad3 related (ATR), the ATR activating proteins, RAD9A and RAD18 and also two tumour suppressor proteins involved in double strand break repair by homologous recombination, BRCA1 and BRCA2 (FIG. 7E).

Figure 8:
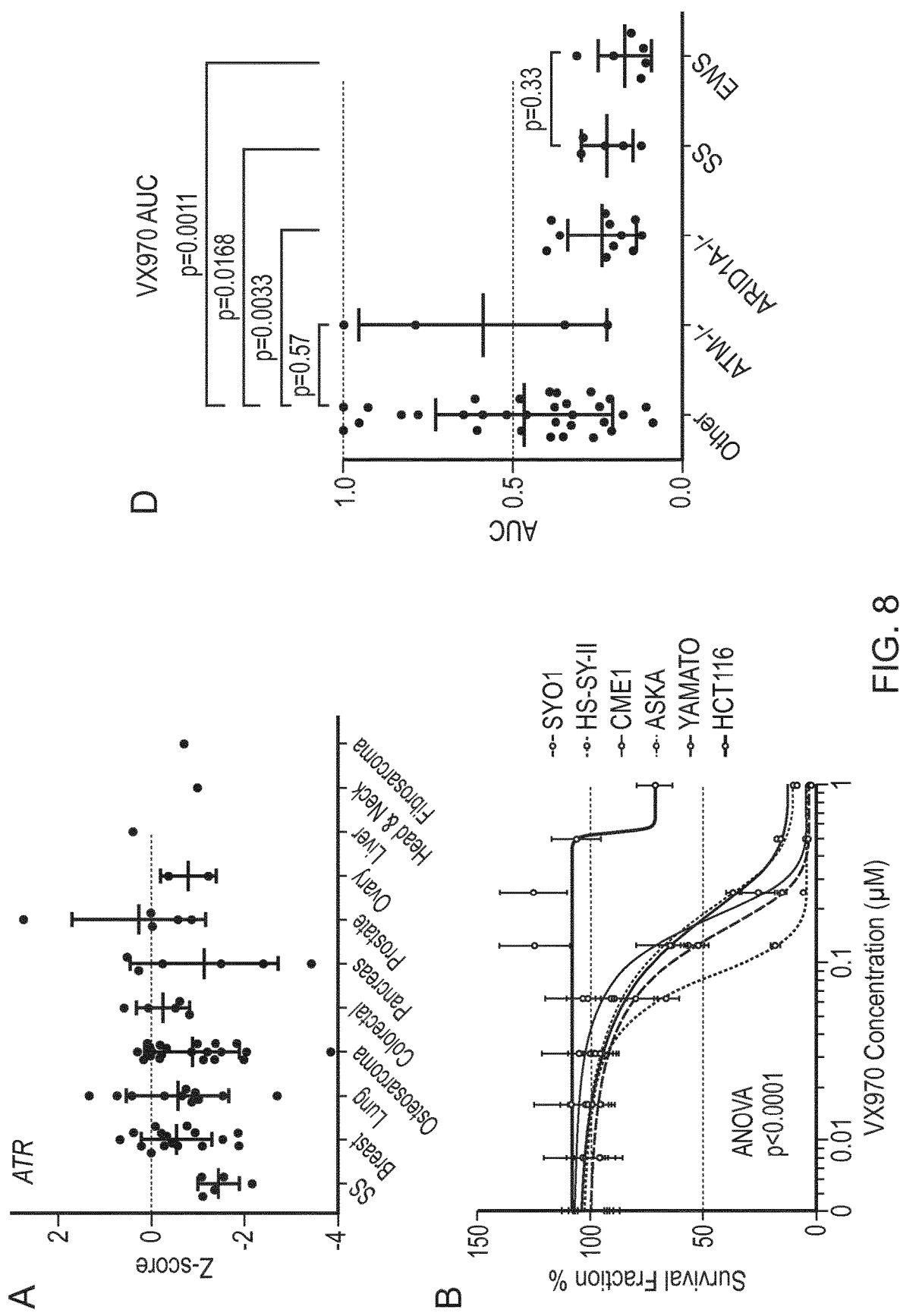
FIG. 8. ATR genetic dependency synovial sarcoma tumour cells—part 1. A. ATR siRNA Z scores from the siRNA screens described in FIG. 7, classified according to the cancer histology of tumour cell lines. B. Dose-response survival curves illustrating sensitivity of SS tumour cell lines to the ATR small molecule inhibitor (ATRi) VX970, compared to ATRi resistant HCT116 cells. Cells were exposed to drugs for five days and cell viability estimated using CellTiter-Glo. For each SS tumour cell line, dose response ANOVA p<0.0001 vs. HCT116. C. Dose-response survival curves illustrating sensitivity of SS tumour cell lines to VX970, compared to ATRi resistant ARID1A wild type HCT116 cells (HCT116 ARID1A$^{+/+}$) and ARID1A defective HCT116 cells (HCT116 ARID1A$^{-/-}$). Cells were exposed to drugs for five days and cell viability estimated using CellTiter-Glo. For each SS tumour cell line and HCT116 ARID1A$^{-/-}$, dose response ANOVA p<0.0001 vs. HCT116 ARID1A$^{+/+}$. D. VX970 area under the curve (AUC) values in tumour cell lines. ARID1A defective cells indicated as "ARID1A$^{-/-}$", Ewings sarcoma tumour cell lines shown as "EWS". E. Anti-tumour response in mice bearing established synovial sarcoma PDX, SA13412, to treatment with VX970. Median tumour volumes after the initiation of VX970 treatment are shown. Error bars represent standard error of the mean (SEM). F. Kaplan-Meier survival plot of data from (E). log rank Mantel p=0.026. G. Western blot illustrating expression of synovial sarcoma fusion proteins in HCT116 cells. A SS18-SSX1 variant with the final eight residues of SSX1 deleted (Δ71-78) is shown as d71-78. H. Bar chart illustrating induction of AXIN2 mRNA after expression of synovial sarcoma fusion proteins in HCT116 cells. I-K. Dose-response survival curves illustrating that expression of synovial sarcoma fusion proteins in HCT116 cells causes ATRi sensitivity. Expression of SSX18-SSX1 or SSX18-SSX2 cause ATRi sensitivity but expression of Δ71-78 does not.
Figure 8:
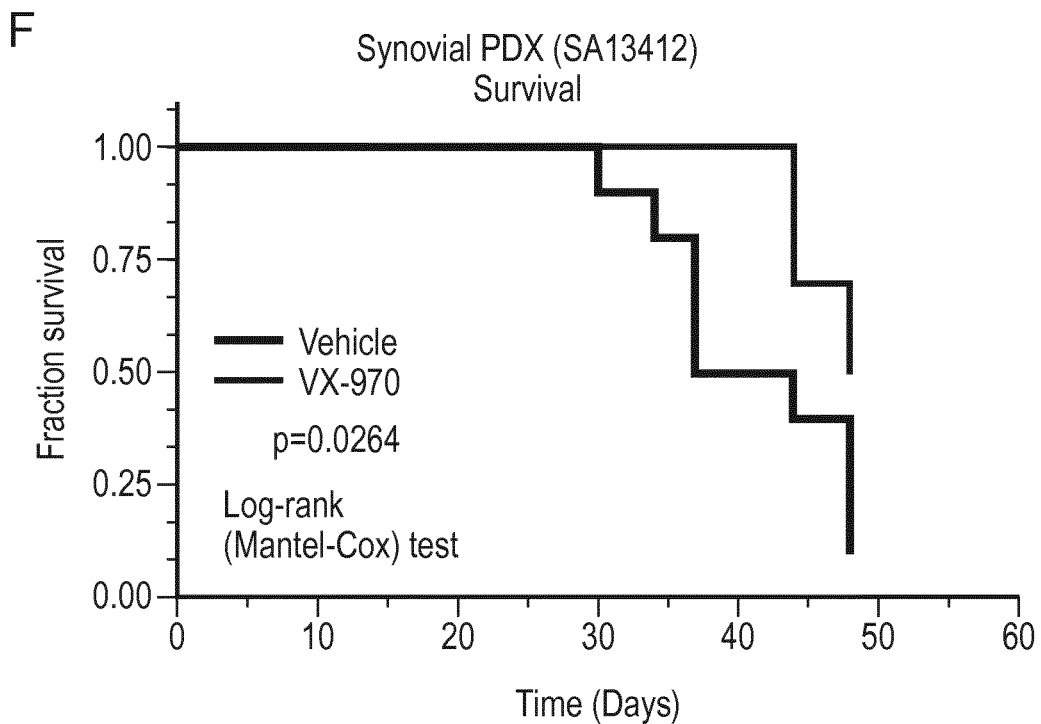
Figure 8:
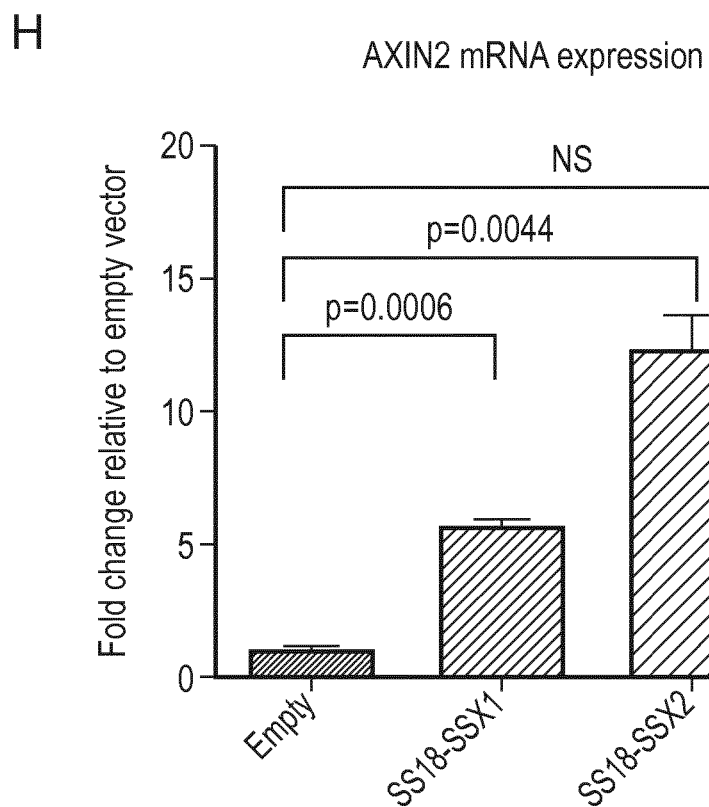
Figure 8:
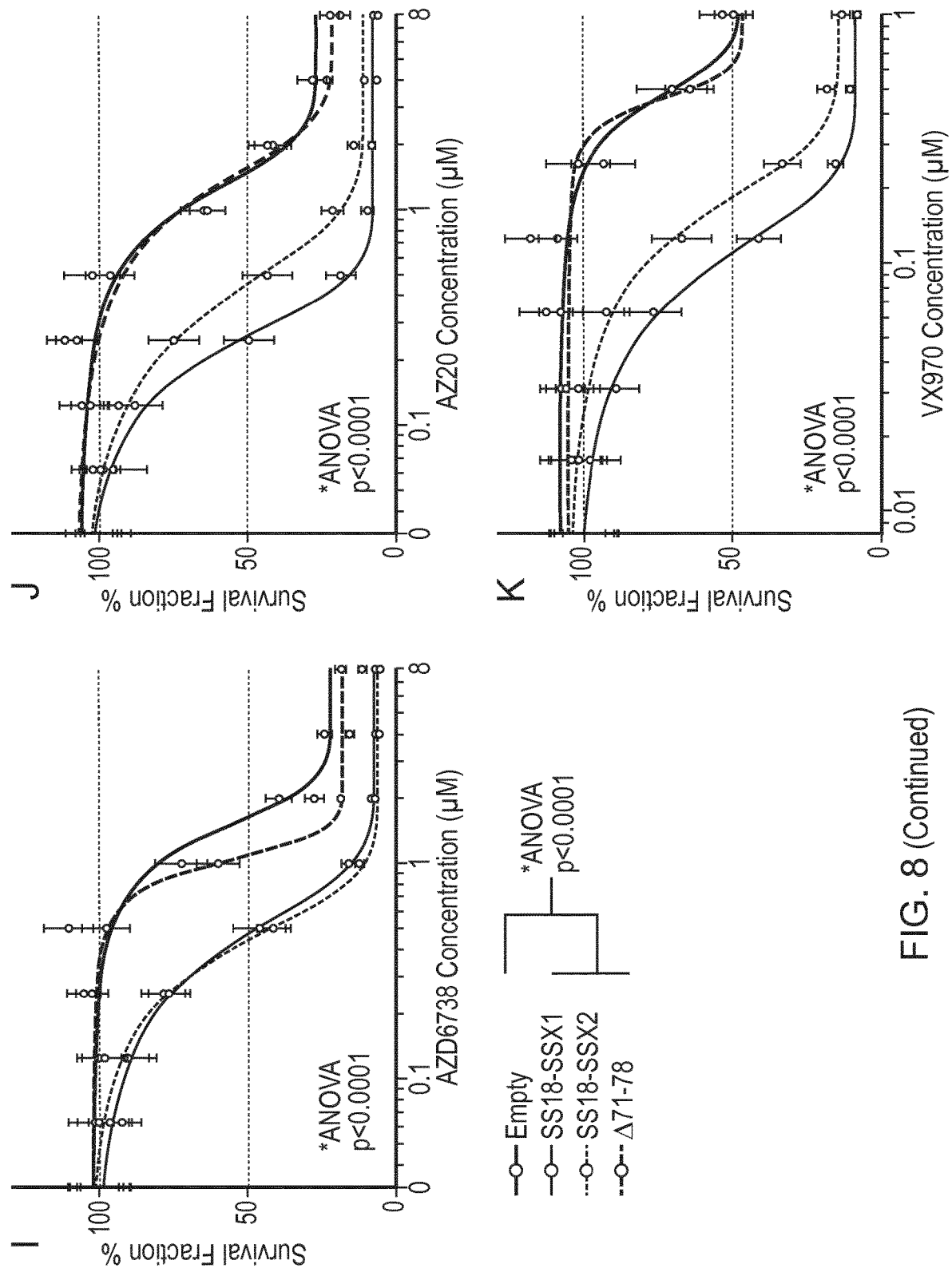

ATR Genetic Dependency in Synovial Sarcoma can be Elicited with Clinical ATR Inhibitors and is Caused by Expression of SS18-SSX1 and SS18-SSX2 Fusion Proteins The identification of ATR as a genetic dependency was particularly interesting for a number of reasons: (i) when comparing the ATR siRNA Z scores for tumour cell lines from different cancer histologies, we found the SS tumour cell lines to be amongst the most sensitive and to respond in a relatively consistent fashion (FIG. 8A); (ii) although SS are often treated with DNA damaging chemotherapies, little is understood about their sensitivity to ATR inhibitors that can exploit tumour-specific defects in the DNA damage response (DDR); (iii) small molecule inhibitors of ATR such as VX970 and AZD6738 have recently entered Phase 1 clinical trials for the treatment of cancer (NCT02157792, NCT02223923), suggesting that this genetic dependency could be clinically actionable.

Figure 9:
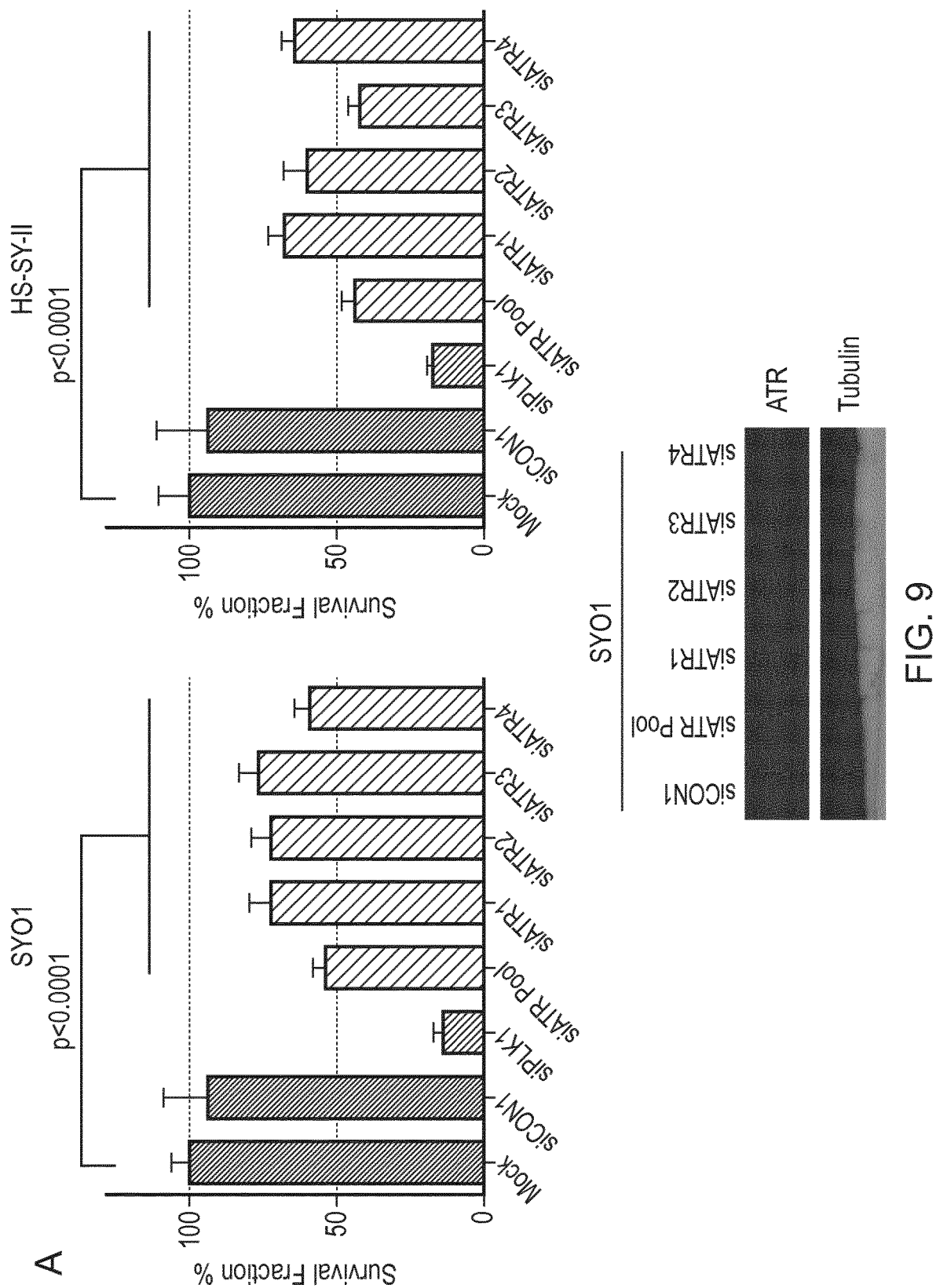
FIG. 9. ATR genetic dependency synovial sarcoma tumour cells—part 2. A. ATR siRNA causes cell inhibition in SS tumour cells. Cells were transfected with ATR siRNAs and cell viability estimated five days later by the use of Cell Titre Glo. Bar chart showing surviving fractions are shown left and middle. Western blot illustrating ATR protein silencing is shown right. Z scores from the siRNA screens described in FIG. 7, classified according to the cancer histology of tumour cell lines. B. Dose-response survival curves illustrating sensitivity of SS tumour cell lines to the ATR small molecule inhibitor (ATRi) VX970, compared to ATRi resistant HCT116 cells and non-tumour cells (HFF1, MCF10A). Cells were exposed to drugs for five days and cell viability estimated using CellTiter-Glo. For each SS tumour cell line, dose response ANOVA p<0.0001 vs. HCT116. C. VX970 surviving fraction 50 values in tumour cell lines exposed to VX970. ARID1A defective cells indicated as "ARID1A$^{-/-}$", Ewings sarcoma tumour cell lines shown as "EWS". D,E. Dose-response survival curves illustrating sensitivity of SS tumour cell lines to additional ATR small molecule inhibitors (ATRi) AZD6738, AZ20 and VE821, compared to ATRi resistant HCT116 cells. Cells were exposed to drugs for five days and cell viability estimated using CellTiter-Glo.
Figure 9:
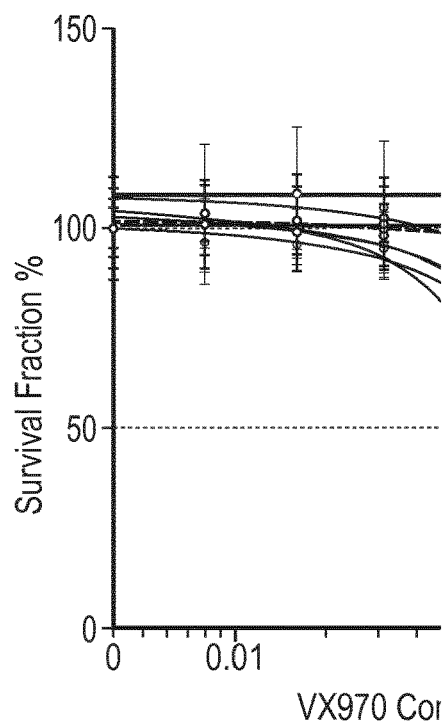
Figure 9:
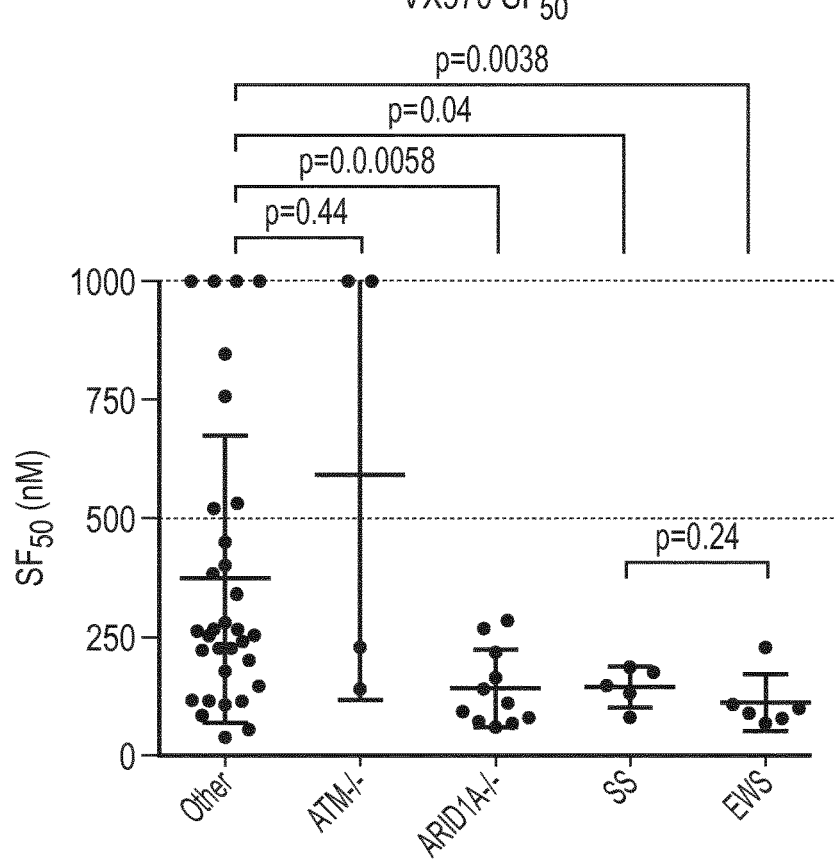
Figure 9:
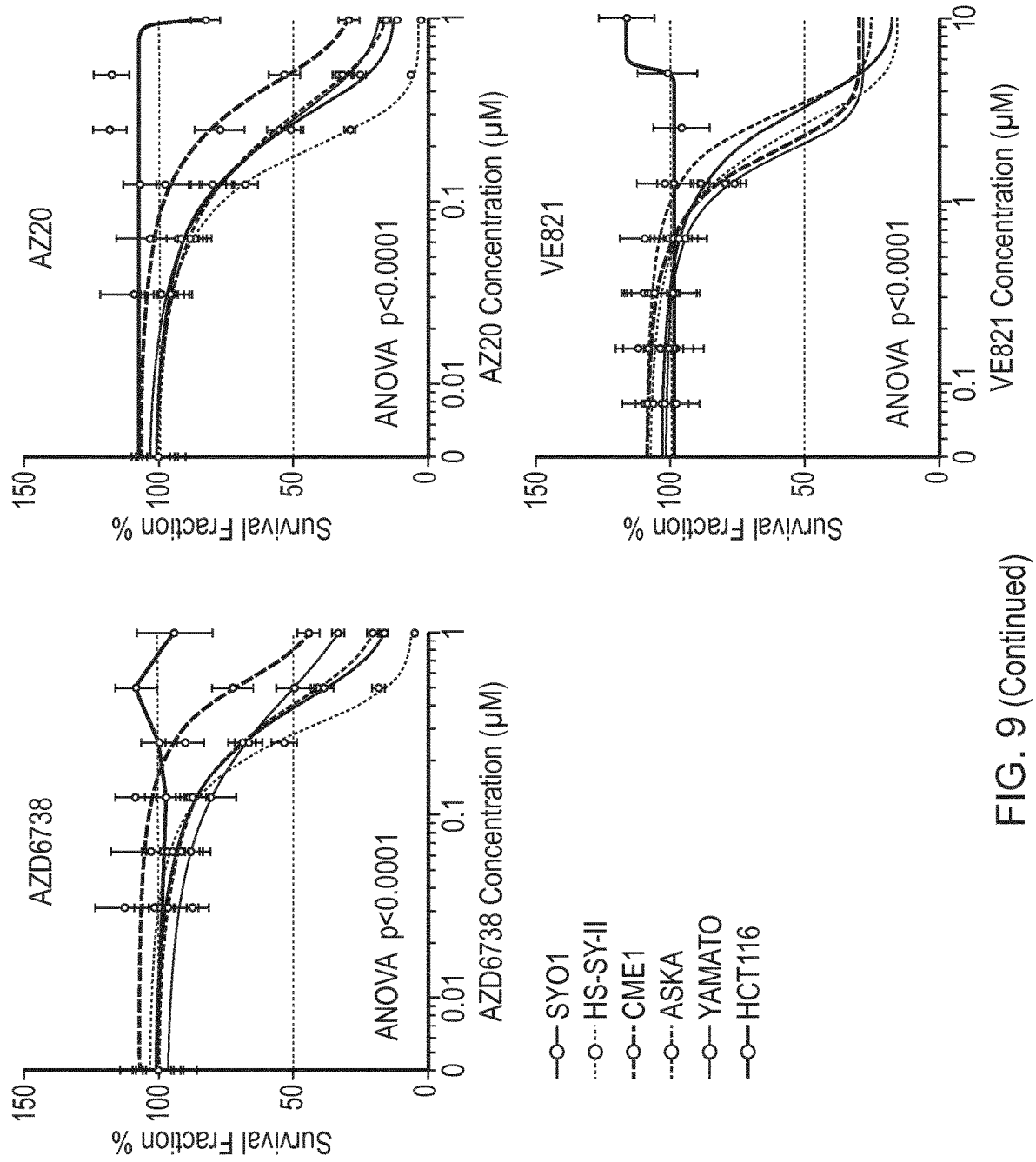
Figure 9:
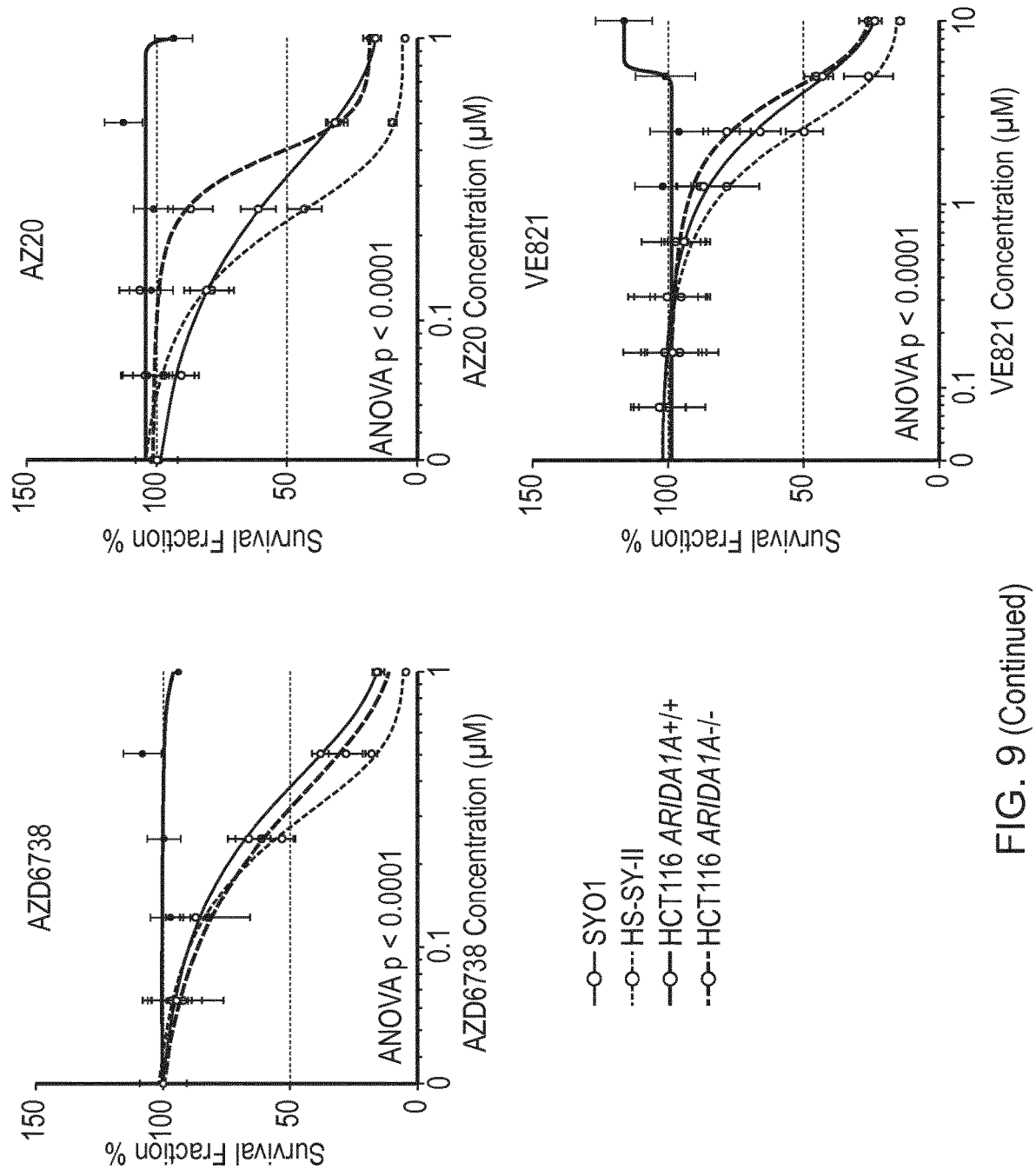

Having confirmed the sensitivity of SS tumour cell lines to siRNA in validation experiments (FIG. 9A), we assessed the sensitivity of the five SS tumour cell lines to the clinical ATR inhibitor (ATRi), VX970 (Vertex Pharmaceuticals). Compared to previously-validated ATRi resistant HCT116 cells PMID: 27958275, all five SS tumour cell lines were profoundly sensitive to VX970 (ANOVA p<0.0001), each exhibiting with SF50 values of ≈0.1 □M (concentration required to cause 50% reduction in cell survival) (FIG. 7B). This was also the case, when the sensitivity of SS tumour cell lines was compared to HFF1 fibroblasts and non-tumour epithelial MCF10A cells (FIG. 9B). Previously we demonstrated that defects in the tumour suppressor gene ARID1A, cause ATRi sensitivity (PMID: 27958275). We found SS tumour cell lines to be as sensitive to VX970 as HCT116 cells where both copies of ARID1A had been rendered dysfunctional by gene targeting (FIG. 7C). Furthermore, when comparing the VX970 sensitivity of SS tumour cell lines to those with other molecular defects associated with ATRi sensitivity, namely ATM gene defects, ARID1A alterations and Ewing's sarcoma tumour cells with EWS-FLI fusions (PMID: 27577084), the SS tumour cell lines showed VX970 sensitivity comparable with those in Ewing's sarcoma tumour cells and tumour cells with ARID1A defects (FIG. 7D, FIG. 9C). This consistent in vitro sensitivity to ATRi in SS tumour cell lines was not restricted to VX970 and was also observed with other ATRi including the clinical ATRi AZD6738 (AstraZeneca (Llona-Minguez, Hoglund et al. 2014)) and the toolbox inhibitors, AZ20 (AstraZeneca (Llona-Minguez, Hoglund et al. 2014)) and VE821(Vertex Pharmaceuticals (Charrier, Durrant et al. 2011)) (FIG. 9D,E). Furthermore, treatment of mice bearing established patient-derived synovial sarcoma xenografts (PDX SA13412) with VX970 caused inhibition of tumour growth (ANOVA p<0.0001, FIG. 8E) and an increase in survival time (log rank Mantel p=0.026, FIG. 8F), suggesting that this might be an effect worthy of further investigation.

Figure 10:
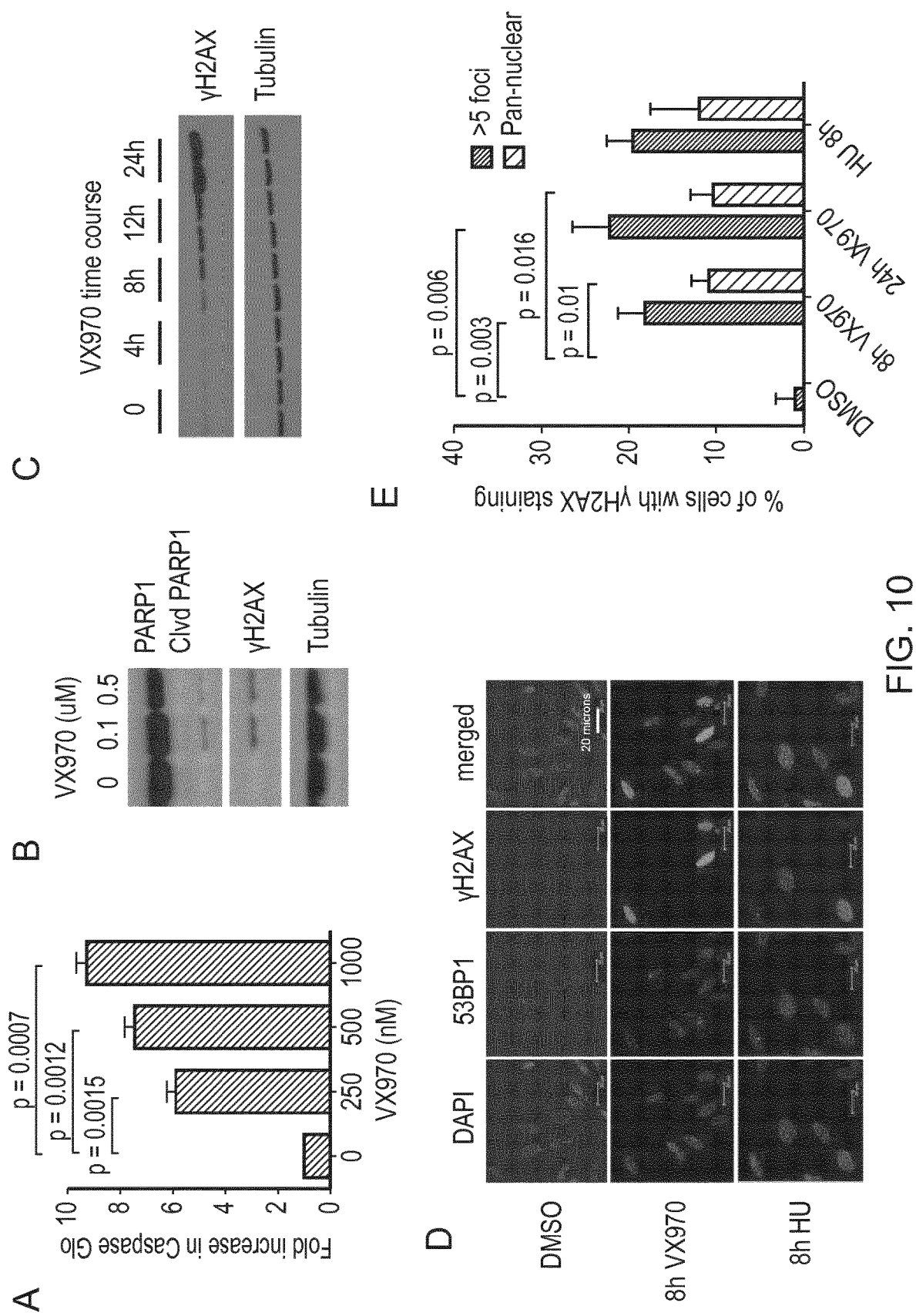
FIG. 10. ATR inhibitors elicit replication fork stress in SS tumour cells. A. Bar chart indicating apoptosis, estimated by Caspase Glo, caused by exposure of SYO1 cells to VX970. Error bars represent SEM from triplicate experiments. p values were derived from Student's t tests. B. Western blot illustrating PARP1 cleavage in SYO1 cells exposed to VX970 for 24 hours. C. Western blot illustrating H2AX phosphorylation (γH2AX) in SYO1 cells exposed to VX970 (0.1 µM). D. Confocal microspcopy images illustrating H2AX phosphorylation in SYO1 cells exposed to VX970 (0.1 µM, 24 hours). E. Bar chart depicting data from (D). Error bars represent SEM from 100 images. p values were derived from Student's t tests. F. Replication fork speeds in SYO1 cells exposed to 0.1 µM VX970 for two hours. p value was derived from a Student's t test. G. Replication fork speeds in HCT116 cells exposed to 0.1 µM VX970 for two hours in the presence and absence of ectopic expression of a SS18-SSX1 fusion protein. p values were derived from Student's t tests. Expression of SS18-SSX1 or exposure to VX970 reduced fork speed. Combined SS18-SSX1 expression and VX970 exposure enhanced the reduction in fork speed. H and I. FACS plots from SYO1 cells exposed to VX970. 0.1 µM VX970 exposure causes an increase in cells in S phase and an increase in the sub $G_1$ fraction.
Figure 10:
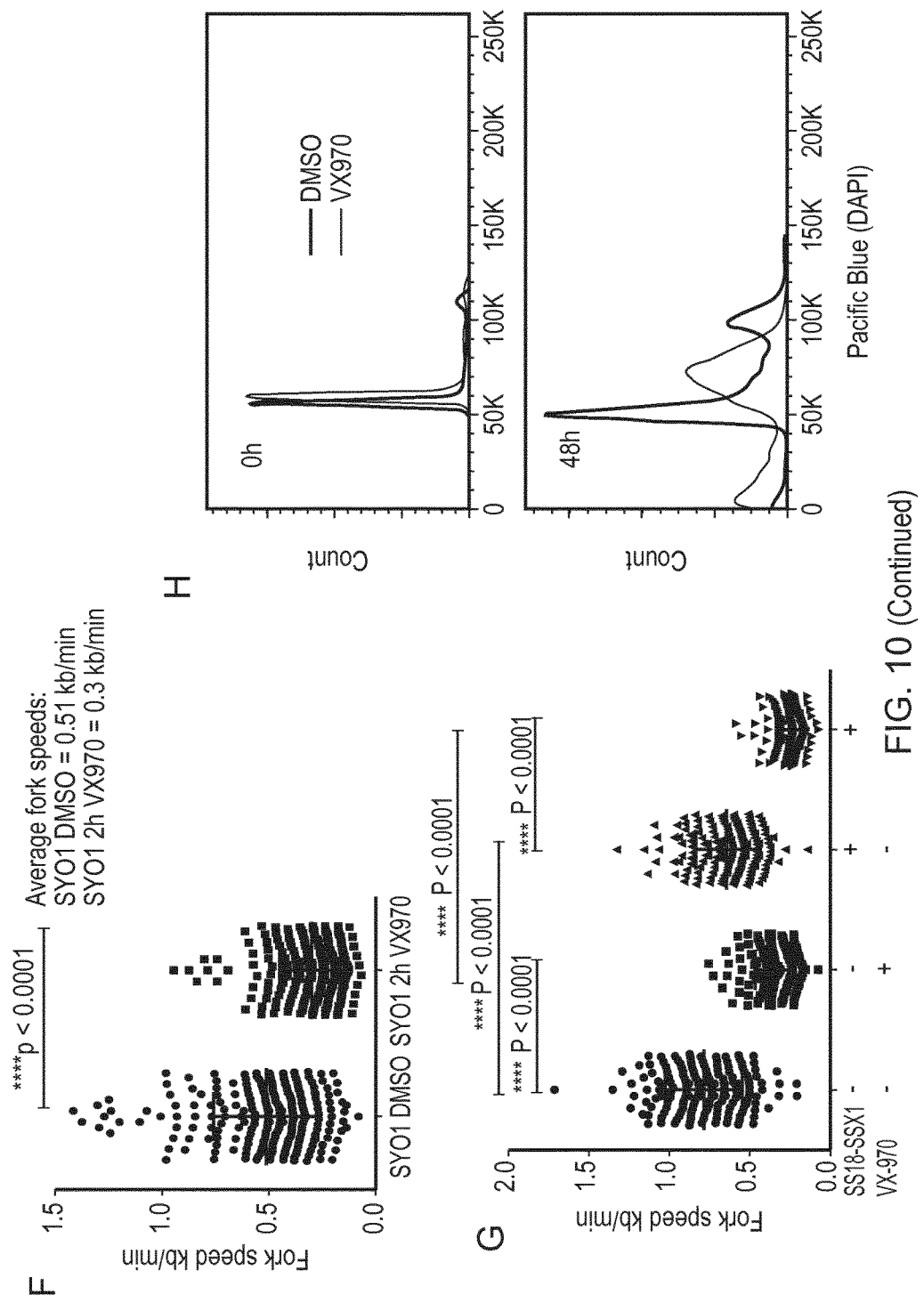

Although these experiments strongly suggested that SS tumor cells might be profoundly sensitive to ATR inhibition, we had not formally confirmed that these effects were associated with expression of a SS18-SSX family fusion protein. We found that unlike many cells, including HFF1 fibroblasts, HCT116 cells (ATRi resistant) were able to tolerate expression of an SS18-SSX1 or SS18-SSX2 cDNA from a lentiviral construct. Furthermore, expression of SS18-SSX1 or SS18-SSX2 in HCT116 cells recapitulated three features associated with SS fusion gene expression, namely modest reductions in the expression of endogenous SS18, a reduction in levels of the SWI/SNF component SMARCB1 (both likely caused by displacement of SS18 and SMARCB1 from SWI/SNF BAF complex (Kadoch and Crabtree 2013, Ito, Asano et al. 2015) and upregulation of a canonical Wnt pathway target gene AXIN2 (FIG. 8G,H). Kadoch and Crabtree recently established that residues at the C-terminus of the SS18-SSX1 fusion protein are critical for the displacement of SMARCB1 from SWI/SNF complexes (Kadoch and Crabtree 2013). In comparison to the expression of full-length SS18-SSX1 or SS18-SSX2 fusion proteins, expression of a SS18-SSX1 variant with the final eight residues of SSX1 deleted (Δ71-78) did not cause a reduction in SMARCB1 levels nor an increase in AXIN2 mRNA (FIG. 8G,H). When we assessed the ATRi sensitivity of HCT116 cells expressing either SS18-SSX1, SS18-SSX2 or Δ71-78, we found both SS18-SSX1 and SS18-SSX2 to cause a significant (ANOVA p<0.0001) enhancement in ATRi sensitivity, but not expression of Δ71-78 (FIG. 8I-K), effects also replicated in mesenchymal U20S osteosarcoma cells.
ATRi Causes Apoptosis and Replication Fork Stress in SS Tumour Cells and Synthetic Lethality in a Cyclin E Dependent Fashion ATRi induced cytotoxicity in tumour cells derived from carcinomas is often associated with an increase in replication fork stress. We found that SS tumour cells exposed to ATRi underwent apoptosis (γH2AX), a biomarker of replication fork stress (FIG. 10C-D). To formally assess replication fork stress, we used DNA fibre analysis (Schwab and Niedzwiedz 2011) and found that in SYO1 cells, VX970 caused a significant reduction in replication fork speed (p<0.0001, FIG. 10E), confirming the results of the γH2AX analysis. Furthermore, we found that expression of SS18-SSX1 in HCT116 cells alone caused a modest but significant decrease in replication fork speed (p<0.0001,) but this was enhanced by the addition of VX970 (FIG. 10F), suggesting that ATR inhibition might target replication fork stress caused by a synovial sarcoma fusion. Consistent with this hypothesis, we found SS tumour cells to arrest in S phase when exposed to VX970 (FIG. 10G).

REFERENCES

The documents disclosed herein are all expressly incorporated by reference in their entirety.
1. Shiloh, Y. & Ziv, Y. The ATM protein kinase: regulating the cellular response to genotoxic stress, and more. Nat Rev Mol Cell Biol 14, 197-210 (2013).
2. Zou, L. & Elledge, S. J. Sensing DNA damage through ATRIP recognition of RPA-ssDNA complexes. Science 300, 1542-1548 (2003).
3. Moynahan, M. E. & Jasin, M. Mitotic homologous recombination maintains genomic stability and suppresses tumorigenesis. Nat Rev Mol Cell Biol 11, 196-207 (2010).
4. Zeman, M. K. & Cimprich, K. A. Causes and consequences of replication stress. Nat Cell Biol 16, 2-9 (2014).
5. Karnitz, L. M. & Zou, L. Molecular Pathways: Targeting ATR in Cancer Therapy. Clin Cancer Res (2015).
6. Pires, I. M., et al. Targeting radiation-resistant hypoxic tumour cells through ATR inhibition. Br J Cancer 107, 291-299 (2012).
7. Reaper, P. M., et al. Selective killing of ATM- or p53-deficient cancer cells through inhibition of ATR. Nat Chem Biol 7, 428-430 (2011).
8. Josse, R., et al. ATR inhibitors VE-821 and VX-970 sensitize cancer cells to topoisomerase i inhibitors by disabling DNA replication initiation and fork elongation responses. Cancer Res 74, 6968-6979 (2014).
9. Huntoon, C. J., et al. ATR inhibition broadly sensitizes ovarian cancer cells to chemotherapy independent of BRCA status. Cancer Res 73, 3683-3691 (2013).
10. Mohni, K. N., Kavanaugh, G. M. & Cortez, D. ATR pathway inhibition is synthetically lethal in cancer cells with ERCC1 deficiency. Cancer Res 74, 2835-2845 (2014).
11. Sultana, R., et al. Ataxia telangiectasia mutated and Rad3 related (ATR) protein kinase inhibition is synthetically lethal in XRCC1 deficient ovarian cancer cells. PLoS One 8, e57098 (2013).
12. Kwok, M., et al. Synthetic lethality in chronic lymphocytic leukaemia with DNA damage response defects by targeting the ATR pathway. Lancet 385 Suppl 1, S58 (2015).
13. Kadoch, C., et al. Proteomic and bioinformatic analysis of mammalian SWI/SNF complexes identifies extensive roles in human malignancy. Nat Genet 45, 592-601 (2013).
14. Wang, X., et al. Two related ARID family proteins are alternative subunits of human SWI/SNF complexes. Biochem J 383, 319-325 (2004).
15. Reisman et al. The SWI/SNF complex and cancer. Oncogene 28: 1653-1668 (2009).
16. Kozmik Z, et al Characterization of mammalian orthologues of the Drosophila osa gene: cDNA cloning, expression, chromosomal localization, and direct physical interaction with Brahma chromatin-remodeling complex. Genomics 73: 140-148 (2001).
17. Huang J, et al. Genomic and functional evidence for an ARID1A tumor suppressor role. Genes Chromosomes Cancer 46: 745-750 (2007).
18. Wang X, et al. Expression of p270 (ARID1A), a component of human SWI/SNF complexes, in human tumors. Int J Cancer 112: 636 (2004a).

19. Lui S. et al. ATR autophosphorylation as a molecular switch for checkpoint activation, Mol. Cell 43: 192-202 (2011).
20. Shain & Pollack. The Spectrum of SWI/SNF Mutations, Ubiquitous in Human Cancers. PLoS One:8(1): e55119 (2013).
21. Lord, C. J., McDonald, S., Swift, S., Turner, N. C. & Ashworth, A. A highthroughput RNA interference screen for DNA repair determinants of PARP inhibitor sensitivity. DNA Repair (Amst) 7, 2010-2019 (2008).
22. Remington's Pharmaceutical Sciences, 20th Edition, 2000, pub. Lippincott, Williams & Wilkins Amary, M. F., F. Berisha, C. Bernardi Fdel, A. Herbert, M. James, J. S. Reis-Filho, C. Fisher, A. G. Nicholson, R. Tirabosco, T. C. Diss and A. M. Flanagan (2007). "Detection of SS18-SSX fusion transcripts in formalin-fixed paraffin-embedded neoplasms: analysis of conventional RT-PCR, qRT-PCR and dual color FISH as diagnostic tools for synovial sarcoma." Mod Pathol 20(4): 482-496.

Baird, K., S. Davis, C. R. Antonescu, U. L. Harper, R. L. Walker, Y. Chen, A. A. Glatfelter, P. H. Duray and P. S. Meltzer (2005). "Gene expression profiling of human sarcomas: insights into sarcoma biology." Cancer Res 65(20): 9226-9235.

Barham, W., A. L. Frump, T. P. Sherrill, C. B. Garcia, K. Saito-Diaz, M. N. Vansaun, B. Fingleton, L. Gleaves, D. Orton, M. R. Capecchi, T. S. Blackwell, E. Lee, F. Yull and J. E. Eid (2013). "Targeting the Wnt Pathway in Synovial Sarcoma Models." Cancer Discov.

Bartkova, J., N. Rezaei, M. Liontos, P. Karakaidos, D. Kletsas, N. Issaeva, L. V. Vassiliou, E. Kolettas, K. Niforou, V. C. Zoumpourlis, M. Takaoka, H. Nakagawa, F. Tort, K. Fugger, F. Johansson, M. Sehested, C. L. Andersen, L. Dyrskjot, T. Orntoft, J. Lukas, C. Kittas, T. Helleday, T. D. Halazonetis, J. Bartek and V. G. Gorgoulis (2006). "Oncogene-induced senescence is part of the tumorigenesis barrier imposed by DNA damage checkpoints." Nature 444(7119): 633-637.

Brough, R., J. R. Frankum, D. Sims, A. Mackay, A. M. Mendes-Pereira, I. Bajrami, S. Costa-Cabral, R. Rafig, A. S. Ahmad, M. A. Cerone, R. Natrajan, R. Sharpe, K. K. Shiu, D. Wetterskog, K. J. Dedes, M. B. Lambros, T. Rawjee, S. Linardopoulos, J. S. Reis-Filho, N. C. Turner, C. J. Lord and A. Ashworth (2011). "Functional viability profiles of breast cancer." Cancer Discov 1(3): 260-273.

Campbell, J., C. J. Ryan, R. Brough, I. Bajrami, H. N. Pemberton, I. Y. Chong, S. Costa-Cabral, J. Frankum, A. Gulati, H. Holme, R. Miller, S. Postel-Vinay, R. Rafig, W. Wei, C. T. Williamson, D. A. Quigley, J. Tym, B. Al-Lazikani, T. Fenton, R. Natrajan, S. J. Strauss, A. Ashworth and C. J. Lord (2016). "Large-Scale Profiling of Kinase Dependencies in Cancer Cell Lines." Cell Rep.

Charrier, J. D., S. J. Durrant, J. M. Golec, D. P. Kay, R. M. Knegtel, S. MacCormick, M. Mortimore, M. E. O'Donnell, J. L. Pinder, P. M. Reaper, A. P. Rutherford, P. S. Wang, S. C. Young and J. R. Pollard (2011). "Discovery of potent and selective inhibitors of ataxia telangiectasia mutated and Rad3 related (ATR) protein kinase as potential anticancer agents." J Med Chem 54(7): 2320-2330.

Chen, T., F. K. Middleton, S. Falcon, P. M. Reaper, J. R. Pollard and N. J. Curtin (2015). "Development of pharmacodynamic biomarkers for ATR inhibitors." Mol Oncol 9(2): 463-472.

Clark, J., P. J. Rocques, A. J. Crew, S. Gill, J. Shipley, A. M. Chan, B. A. Gusterson and C. S. Cooper (1994). "Identification of novel genes, SYT and SSX, involved in the t (X; 18) (p11.2; q11.2) translocation found in human synovial sarcoma." Nat Genet 7(4): 502-508.

D'Arcy, P., W. Maruwge, B. A. Ryan and B. Brodin (2008). "The oncoprotein SS18-SSX1 promotes p53 ubiquitination and degradation by enhancing HDM2 stability." Mol Cancer Res 6(1): 127-138.

de Bruijn, D. R., S. V. Allander, A. H. van Dijk, M. P. Willemse, J. Thijssen, J. J. van Groningen, P. S. Meltzer and A. G. van Kessel (2006). "The synovial-sarcoma-associated SS18-SSX2 fusion protein induces epigenetic gene (de)regulation." Cancer Res 66(19): 9474-9482.

Fokas, E., R. Prevo, J. R. Pollard, P. M. Reaper, P. A. Charlton, B. Cornelissen, K. A. Vallis, E. M. Hammond, M. M. Olcina, W. Gillies McKenna, R. J. Muschel and T. B. Brunner (2012). "Targeting ATR in vivo using the novel inhibitor VE-822 results in selective sensitization of pancreatic tumors to radiation." Cell Death Dis 3: e441.

Gaillard, H., T. Garcia-Muse and A. Aguilera (2015). "Replication stress and cancer." Nat Rev Cancer 15(5): 276-289.

Garcia, C. B., C. M. Shaffer, M. P. Alfaro, A. L. Smith, J. Sun, Z. Zhao, P. P. Young, M. N. VanSaun and J. E. Eid (2012). "Reprogramming of mesenchymal stem cells by the synovial sarcoma-associated oncogene SYT-SSX2." Oncogene 31(18): 2323-2334.

Garcia, C. B., C. M. Shaffer and J. E. Eid (2012). "Genome-wide recruitment to Polycomb-modified chromatin and activity regulation of the synovial sarcoma oncogene SYT-SSX2." BMC Genomics 13: 189.

Haldar, M., J. D. Hancock, C. M. Coffin, S. L. Lessnick and M. R. Capecchi (2007). "A conditional mouse model of synovial sarcoma: insights into a myogenic origin." Cancer Cell 11(4): 375-388.

Hayakawa, K., M. Ikeya, M. Fukuta, K. Woltjen, S. Tamaki, N. Takahara, T. Kato, Jr., S. Sato, T. Otsuka and J. Toguchida (2013). "Identification of target genes of synovial sarcoma-associated fusion oncoprotein using human pluripotent stem cells." Biochem Biophys Res Commun 432(4): 713-719.

Huntoon, C. J., K. S. Flatten, A. E. Wahner Hendrickson, A. M. Huehls, S. L. Sutor, S. H. Kaufmann and L. M. Karnitz (2013). "ATR inhibition broadly sensitizes ovarian cancer cells to chemotherapy independent of BRCA status." Cancer Res 73(12): 3683-3691.

Ito, J., N. Asano, A. Kawai and A. Yoshida (2015). "The diagnostic utility of reduced immunohistochemical expression of SMARCB1 in synovial sarcomas: a validation study." Hum Pathol.

Jones, K. B., J. J. Barrott, M. Xie, M. Haldar, H. Jin, J. F. Zhu, M. J. Monument, T. L. Mosbruger, E. M. Langer, R. L. Randall, R. K. Wilson, B. R. Cairns, L. Ding and M. R. Capecchi (2016). "The impact of chromosomal translocation locus and fusion oncogene coding sequence in synovial sarcomagenesis." Oncogene.

Jones, R. M., O. Mortusewicz, I. Afzal, M. Lorvellec, P. Garcia, T. Helleday and E. Petermann (2013). "Increased replication initiation and conflicts with transcription underlie Cyclin E-induced replication stress." Oncogene 32(32): 3744-3753.

Josse, R., S. E. Martin, R. Guha, P. Ormanoglu, T. D. Pfister, P. M. Reaper, C. S. Barnes, J. Jones, P. Charlton, J. R. Pollard, J. Morris, J. H. Doroshow and Y. Pommier (2014). "ATR inhibitors VE-821 and VX-970 sensitize cancer cells to topoisomerase i inhibitors by disabling DNA replication initiation and fork elongation responses." Cancer Res 74(23): 6968-6979.

Kadoch, C. and G. R. Crabtree (2013). "Reversible disruption of mSWI/SNF (BAF) complexes by the SS18-SSX oncogenic fusion in synovial sarcoma." Cell 153(1): 71-85.

Kadoch, C., D. C. Hargreaves, C. Hodges, L. Elias, L. Ho, J. Ranish and G. R. Crabtree (2013). "Proteomic and bioinformatic analysis of mammalian SWI/SNF complexes identifies extensive roles in human malignancy." Nat Genet 45(6): 592-601.

Koh, J. L., K. R. Brown, A. Sayad, D. Kasimer, T. Ketela and J. Moffat (2012). "COLT-Cancer: functional genetic screening resource for essential genes in human cancer cell lines." Nucleic Acids Res 40(Database issue): D957-963.

Kwok, M., N. Davies, A. Agathanggelou, E. Smith, C. Oldreive, E. Petermann, G. Stewart, J. Brown, A. Lau, G. Pratt, H. Parry, M. Taylor, P. Moss, P. Hillmen and T. Stankovic (2015). "ATR inhibition induces synthetic lethality and overcomes chemoresistance in TP53 or ATM defective chronic lymphocytic leukemia cells." Blood.

Kwok, M., N. Davies, A. Agathanggelou, E. Smith, C. Oldreive, E. Petermann, G. Stewart, J. Brown, A. Lau, G. Pratt, H. Parry, M. Taylor, P. Moss, P. Hillmen and T. Stankovic (2016). "ATR inhibition induces synthetic lethality and overcomes chemoresistance in TP53- or ATM-defective chronic lymphocytic leukemia cells." Blood 127(5): 582-595.

Kwok, M., N. Davies, A. Agathanggelou, E. Smith, E. Petermann, E. Yates, J. Brown, A. Lau and T. Stankovic (2015). "Synthetic lethality in chronic lymphocytic leukaemia with DNA damage response defects by targeting the ATR pathway." Lancet 385 Suppl 1: S58.

Llona-Minguez, S., A. Hoglund, S. A. Jacques, T. Koolmeister and T. Helleday (2014). "Chemical strategies for development of ATR inhibitors." Expert Rev Mol Med 16: e10.

Lord, C. J. and A. Ashworth (2016). "BRCAness revisited." Nat Rev Cancer 16(2): 110-120.

Lord, C. J., A. N. Tutt and A. Ashworth (2015). "Synthetic lethality and cancer therapy: lessons learned from the development of PARP inhibitors." Annu Rev Med 66: 455-470.

Mateo, J., S. Carreira, S. Sandhu, S. Miranda, H. Mossop, R. Perez-Lopez, D. Nava Rodrigues, D. Robinson, A. Omlin, N. Tunariu, G. Boysen, N. Porta, P. Flohr, A. Gillman, I. Figueiredo, C. Paulding, G. Seed, S. Jain, C. Ralph, A. Protheroe, S. Hussain, R. Jones, T. Elliott, U. McGovern, D. Bianchini, J. Goodall, Z. Zafeiriou, C. T. Williamson, R. Ferraldeschi, R. Riisnaes, B. Ebbs, G. Fowler, D. Roda, W. Yuan, Y. M. Wu, X. Cao, R. Brough, H. Pemberton, R. A'Hern, A. Swain, L. P. Kunju, R. Eeles, G. Attard, C. J. Lord, A. Ashworth, M. A. Rubin, K. E. Knudsen, F. Y. Feng, A. M. Chinnaiyan, E. Hall and J. S. de Bono (2015). "DNA-Repair Defects and Olaparib in Metastatic Prostate Cancer." N Engl J Med 373(18): 1697-1708.

McKenna, E. S., C. G. Sansam, Y. J. Cho, H. Greulich, J. A. Evans, C. S. Thom, L. A. Moreau, J. A. Biegel, S. L. Pomeroy and C. W. Roberts (2008). "Loss of the epigenetic tumor suppressor SNF5 leads to cancer without genomic instability." Mol Cell Biol 28(20): 6223-6233.

Middeljans, E., X. Wan, P. W. Jansen, V. Sharma, H. G. Stunnenberg and C. Logie (2012). "SS18 together with animal-specific factors defines human BAF-type SWI/SNF complexes." PLoS One 7(3): e33834.

Mohni, K. N., G. M. Kavanaugh and D. Cortez (2014). "ATR pathway inhibition is synthetically lethal in cancer cells with ERCC1 deficiency." Cancer Res 74(10): 2835-2845.

Murga, M., S. Campaner, A. J. Lopez-Contreras, L. I. Toledo, R. Soria, M. F. Montana, L. D'Artista, T. Schleker, C. Guerra, E. Garcia, M. Barbacid, M. Hidalgo, B. Amati and O. Fernandez-Capetillo (2011). "Exploiting oncogene-induced replicative stress for the selective killing of Myc-driven tumors." Nat Struct Mol Biol 18(12): 1331-1335.

Nagai, M., S. Tanaka, M. Tsuda, S. Endo, H. Kato, H. Sonobe, A. Minami, H. Hiraga, H. Nishihara, H. Sawa and K. Nagashima (2001). "Analysis of transforming activity of human synovial sarcoma-associated chimeric protein SYT-SSX1 bound to chromatin remodeling factor hBRM/hSNF2 alpha." Proc Natl Acad Sci USA 98(7): 3843-3848.

Nam, E. A. and D. Cortez (2011). "ATR signalling: more than meeting at the fork." Biochem J 436(3): 527-536.

Nielsen, T. O., N. M. Poulin and M. Ladanyi (2015). "Synovial Sarcoma: Recent Discoveries as a Roadmap to New Avenues for Therapy." Cancer Discov.

Pires, I. M., M. M. Olcina, S. Anbalagan, J. R. Pollard, P. M. Reaper, P. A. Charlton, W. G. McKenna and E. M. Hammond (2012). "Targeting radiation-resistant hypoxic tumour cells through ATR inhibition." Br J Cancer 107 (2): 291-299.

Prichard, M. N. and C. Shipman, Jr. (1990). "A three-dimensional model to analyze drug-drug interactions." Antiviral Res 14(4-5): 181-205.

Reaper, P. M., M. R. Griffiths, J. M. Long, J. D. Charrier, S. Maccormick, P. A. Charlton, J. M. Golec and J. R. Pollard (2011). "Selective killing of ATM- or p53-deficient cancer cells through inhibition of ATR." Nat Chem Biol 7(7): 428-430.

Schoppy, D. W., R. L. Ragland, O. Gilad, N. Shastri, A. A. Peters, M. Murga, O. Fernandez-Capetillo, J. A. Diehl and E. J. Brown (2012). "Oncogenic stress sensitizes murine cancers to hypomorphic suppression of ATR." J Clin Invest 122(1): 241-252.

Schwab, R. A. and W. Niedzwiedz (2011). "Visualization of DNA replication in the vertebrate model system DT40 using the DNA fiber technique." J Vis Exp(56): e3255.

Shen, J., Y. Peng, L. Wei, W. Zhang, L. Yang, L. Lan, P. Kapoor, Z. Ju, Q. Mo, M. Shih Ie, I. P. Uray, X. Wu, P. H. Brown, X. Shen, G. B. Mills and G. Peng (2015). "ARID1A Deficiency Impairs the DNA Damage Checkpoint and Sensitizes Cells to PARP Inhibitors." Cancer Discov 5(7): 752-767.

Smith-Roe, S. L., J. Nakamura, D. Holley, P. D. Chastain, 2nd, G. B. Rosson, D. A. Simpson, J. R. Ridpath, D. G. Kaufman, W. K. Kaufmann and S. J. Bultman (2015). "SWI/SNF complexes are required for full activation of the DNA-damage response." Oncotarget 6(2): 732-745.

Spurrell, E. L., C. Fisher, J. M. Thomas and I. R. Judson (2005). "Prognostic factors in advanced synovial sarcoma: an analysis of 104 patients treated at the Royal Marsden Hospital." Ann Oncol 16(3): 437-444.

Sultan, I., C. Rodriguez-Galindo, R. Saab, S. Yasir, M. Casanova and A. Ferrari (2009). "Comparing children and adults with synovial sarcoma in the Surveillance, Epidemiology, and End Results program, 1983 to 2005: an analysis of 1268 patients." Cancer 115(15): 3537-3547.

Sultana, R., T. Abdel-Fatah, C. Perry, P. Moseley, N. Albarakti, V. Mohan, C. Seedhouse, S. Chan and S. Madhusudan (2013). "Ataxia telangiectasia mutated and Rad3 related (ATR) protein kinase inhibition is synthetically lethal in XRCC1 deficient ovarian cancer cells." PLoS One 8(2): e57098.

Thaete, C., D. Brett, P. Monaghan, S. Whitehouse, G. Rennie, E. Rayner, C. S. Cooper and G. Goodwin (1999). "Functional domains of the SYT and SYT-SSX synovial sarcoma translocation proteins and co-localization with the SNF protein BRM in the nucleus." Hum Mol Genet 8(4): 585-591.

Toledo, L. I., M. Murga, R. Zur, R. Soria, A. Rodriguez, S. Martinez, J. Oyarzabal, J. Pastor, J. R. Bischoff and O. Fernandez-Capetillo (2011). "A cell-based screen identifies ATR inhibitors with synthetic lethal properties for cancer-associated mutations." Nat Struct Mol Biol 18(6): 721-727.

Trautmann, M., E. Sievers, S. Aretz, D. Kindler, S. Michels, N. Friedrichs, M. Renner, J. Kirfel, S. Steiner, S. Huss, A. Koch, R. Penzel, O. Larsson, A. Kawai, S. Tanaka, H. Sonobe, A. Waha, P. Schirmacher, G. Mechtersheimer, E. Wardelmann, R. Buttner and W. Hartmann (2013). "SS18-SSX fusion protein-induced Wnt/beta-catenin signaling is a therapeutic target in synovial sarcoma." Oncogene.

Versteege, I., N. Sevenet, J. Lange, M. F. Rousseau-Merck, P. Ambros, R. Handgretinger, A. Aurias and O. Delattre (1998). "Truncating mutations of hSNF5/INI1 in aggressive paediatric cancer." Nature 394(6689): 203-206.

Vijayakumar, S., G. Liu, I. A. Rus, S. Yao, Y. Chen, G. Akiri, L. Grumolato and S. A. Aaronson (2011). "High-frequency canonical Wnt activation in multiple sarcoma subtypes drives proliferation through a TCF/beta-catenin target gene, CDC25A." Cancer Cell 19(5): 601-612.

Wilson, B. G. and C. W. Roberts (2011). "SWI/SNF nucleosome remodellers and cancer." Nat Rev Cancer 11(7): 481-492.

The invention claimed is:

1. A method for treating an individual having cancer with an Ataxia-Telangiectasia Mutated and Rad3-related protein kinase inhibitor (ATRi), the method comprising:
   (a) determining in a sample obtained from the individual whether the cancer is mutated or deficient in one or more BAF-complex genes, and
   (b) selecting the individual for treatment with the ATRi where the cancer has one or more BAF-complex gene mutations or deficiencies; and
   (c) administering a therapeutically effective amount of the ATRi to the individual, said ATRi eliciting one or more of premature mitotic entry, genomic instability and apoptosis in said cancer cells,
   wherein said ATRi is VE-821, VE-822 (VX-970), AZ20, or AZD6738
   wherein the cancer is mutated or deficient in one or more BAF-complex genes selected from ARID1A, ARID1B, SMARCA4, SMARCB1, and PBRM1,
   wherein the cancer is synovial sarcoma, ovarian clear cell carcinoma, colorectal cancers, melanoma, lung cancer, hepatocellular carcinoma, gastric cancer, bladder cancer, hematologic malignancies, squamous cell carcinoma, serous ovarian cancer, breast cancer, pancreatic cancer, medulloblastoma, renal cancer or glioma,
   and wherein for a cancer mutated in one or more BAF-complex genes, the mutation reduces or abolishes the expression or function of the one or more BAF-complex genes.

2. The method of claim 1, wherein the mutated or deficient BAF-complex gene is selected from one or more of ARID1A, ARID1B, SMARCA4, and SMARCB1.

3. The method of claim 1, wherein the one or more BAF-complex genes is ARID1A.

4. The method according to claim 1, wherein step (a) further comprises identifying gene loss resulting from chromosomal instability through karyotype analysis of a sample obtained from the individual.

5. The method according to claim 4, wherein the BAF-complex gene is ARID1A and loss of ARID1A is indicated by the loss of at least 1p36.11 from chromosome 1.

6. The method according to claim 1, wherein treatment with an ATR inhibitor is combined with one or more further anti-cancer therapies.

7. The method according to claim 6, wherein treatment with ATR inhibitor is used in conjunction with one or more further chemotherapeutic agent(s) and/or in conjunction with radiotherapy.

8. A method for treating an individual having cancer with a mutation or deficiency in one or more BAF-complex genes with an Ataxia-Telangiectasia Mutated and Rad3-related protein kinase inhibitor (ATRi), the method comprising:
   administering a therapeutically effective amount of the ATRi to the individual having cancer with a mutation or deficiency in one or more BAF-complex genes, said ATRi eliciting one or more of premature mitotic entry, genomic instability and apoptosis in said cancer cells, wherein said ATRi is VE-821, VE-822 (VX-970), AZ20, or AZD6738,
   wherein the cancer is mutated or deficient in one or more BAF-complex genes selected from ARID1A, ARID1B, SMARCA4, SMARCB1, and PBRM1,
   wherein the cancer is synovial sarcoma, ovarian clear cell carcinoma, colorectal cancers, melanoma, lung cancer, hepatocellular carcinoma, gastric cancer, bladder cancer, hematologic malignancies, squamous cell carcinoma, serous ovarian cancer, breast cancer, pancreatic cancer, medulloblastoma, renal cancer or glioma,
   and wherein for a cancer with a mutation in one or more BAF-complex genes, the mutation reduces or abolishes the expression or function of the one or more BAF-complex genes.

9. The method of claim 8, wherein treatment with said inhibitor is combined with one or more further anti-cancer therapies.

* * * * *